(12) United States Patent
Blatter

(10) Patent No.: US 7,118,546 B2
(45) Date of Patent: *Oct. 10, 2006

(54) APPARATUS AND METHODS FOR FACILITATING REPEATED VASCULAR ACCESS

(75) Inventor: Duane D. Blatter, Salt Lake City, UT (US)

(73) Assignee: Integrated Vascular Interventional Technologies, L.C., Salt Lake City, UT (US)

( * ) Notice: Subject to any disclaimer, the term of this patent is extended or adjusted under 35 U.S.C. 154(b) by 364 days.

This patent is subject to a terminal disclaimer.

(21) Appl. No.: 10/624,315

(22) Filed: Jul. 21, 2003

(65) Prior Publication Data

US 2004/0019315 A1 Jan. 29, 2004

Related U.S. Application Data

(63) Continuation-in-part of application No. 10/351,172, filed on Jan. 23, 2003, and a continuation-in-part of application No. 09/760,322, filed on Jan. 11, 2001, now Pat. No. 6,663,590, and a continuation-in-part of application No. 09/481,283, filed on Jan. 11, 2000, now Pat. No. 6,595,941, which is a continuation-in-part of application No. 09/480,964, filed on Jan. 11, 2000, now Pat. No. 6,656,151.

(51) Int. Cl.
*A61M 37/00* (2006.01)
*C02F 1/44* (2006.01)
*A61B 17/08* (2006.01)

(52) U.S. Cl. .................. 604/6.16; 604/4.01; 210/645; 606/153

(58) Field of Classification Search ............... 604/4.01, 604/5.01, 5.04, 6.05, 6.06, 6.1, 7–10, 28, 604/6.16, 96.01, 101.04, 103.07, 508, 509, 604/21, 288.1, 891.1, 103.01, 30, 93.01, 604/264; 623/1.25, 1.36, 1.24, 1.42; 128/898; 210/600, 645, 646; 606/139, 153
See application file for complete search history.

(56) References Cited

U.S. PATENT DOCUMENTS

| 3,392,722 A | 7/1968 | Jorgensen |
| 3,395,710 A | 8/1968 | Stratton et al. |

(Continued)

FOREIGN PATENT DOCUMENTS

WO    WO 98/19629    5/1998

(Continued)

OTHER PUBLICATIONS

Lycos, Your Personal Internet Guide, APHERESIS, located at http://infoplease.lycos.com/ipd/A0321273.html, 1 pg, printed Jun. 12, 2003.

(Continued)

*Primary Examiner*—Tatyana Zalukaeva
*Assistant Examiner*—Leslie R. Deak
(74) *Attorney, Agent, or Firm*—Stoel Rives LLP

(57) ABSTRACT

The invention provides vascular access methods, systems and devices facilitating long-term, repeated access to any of a patient's anatomical vessels and the body fluid therein, such as a patient's bloodstream. This is provided by an access tube apparatus adapted for anastomosis to a target anatomical vessel. The access tube has an occluder that fits within the conduit of the access tube when vascular access is not needed. The occluder can be selectively moved or removed to allow for access to the body fluid in the anatomical vessel by way of the access tube.

31 Claims, 34 Drawing Sheets

U.S. PATENT DOCUMENTS

| | | | |
|---|---|---|---|
| 3,713,441 A | 1/1973 | Thomas | |
| 3,826,257 A | 7/1974 | Buselmeier | |
| 3,853,126 A | 12/1974 | Schulte | |
| 3,991,756 A | 11/1976 | Snyder | |
| 4,122,858 A | 10/1978 | Schiff | |
| 4,301,797 A | 11/1981 | Pollack | |
| 4,318,401 A | 3/1982 | Zimmerman | |
| 4,366,810 A | 1/1983 | Kaster | |
| 4,370,983 A | 2/1983 | Lichtenstein | |
| 4,421,507 A * | 12/1983 | Bokros | 604/539 |
| 4,623,348 A | 11/1986 | Feit | |
| 4,655,771 A | 4/1987 | Wallsten | |
| 4,819,637 A | 4/1989 | Dormandy, Jr. et al. | |
| 4,822,341 A * | 4/1989 | Colone | 604/175 |
| 4,846,186 A | 7/1989 | Box et al. | |
| 5,092,841 A | 3/1992 | Spears | |
| 5,102,402 A | 4/1992 | Dror et al. | |
| 5,290,306 A | 3/1994 | Trotta et al. | |
| 5,304,220 A | 4/1994 | Maginot | |
| 5,411,475 A | 5/1995 | Atala et al. | |
| 5,417,657 A | 5/1995 | Hauer | |
| 5,443,497 A | 8/1995 | Venbrux | |
| 5,456,712 A | 10/1995 | Maginot | |
| 5,458,568 A | 10/1995 | Racchini et al. | |
| 5,478,320 A | 12/1995 | Trotta | |
| 5,613,979 A | 3/1997 | Trotta et al. | |
| 5,616,114 A | 4/1997 | Thornton et al. | |
| 5,617,878 A | 4/1997 | Taheri | |
| 5,620,649 A | 4/1997 | Trotta | |
| 5,634,936 A | 6/1997 | Linden et al. | |
| 5,662,580 A | 9/1997 | Bradshaw et al. | |
| 5,662,700 A | 9/1997 | Lazarus | |
| 5,693,088 A | 12/1997 | Lazarus | |
| 5,695,504 A | 12/1997 | Gifford, III et al. | |
| 5,702,412 A | 12/1997 | Popov et al. | |
| 5,755,775 A | 5/1998 | Trerotola et al. | |
| 5,766,158 A | 6/1998 | Opolski | |
| 5,779,731 A | 7/1998 | Leavitt | |
| 5,792,095 A | 8/1998 | Kissinger et al. | |
| 5,795,325 A | 8/1998 | Valley et al. | |
| 5,797,879 A * | 8/1998 | DeCampli | 604/93.01 |
| 5,797,934 A | 8/1998 | Rygaard | |
| 5,817,113 A | 10/1998 | Gifford, III et al. | |
| 5,830,222 A | 11/1998 | Makower | |
| 5,830,228 A | 11/1998 | Knapp et al. | |
| 5,843,027 A | 12/1998 | Stone et al. | |
| 5,868,770 A | 2/1999 | Rygaard | |
| 5,893,369 A | 4/1999 | LeMole | |
| 5,925,060 A | 7/1999 | Forber | |
| 5,954,706 A | 9/1999 | Sahatjian | |
| 5,961,536 A | 10/1999 | Mickley et al. | |
| 5,976,178 A | 11/1999 | Goldsteen et al. | |
| 6,007,576 A | 12/1999 | McClellan | |
| 6,030,392 A | 2/2000 | Dakov | |
| 6,042,569 A | 3/2000 | Finch, Jr. et al. | |
| 6,063,114 A | 5/2000 | Nash et al. | |
| 6,068,637 A | 5/2000 | Popov et al. | |
| 6,086,553 A | 7/2000 | Akbik | |
| 6,102,884 A | 8/2000 | Squitieri | |
| 6,113,612 A | 9/2000 | Swanson et al. | |
| 6,171,319 B1 | 1/2001 | Nobles et al. | |
| 6,214,022 B1 | 1/2001 | Taylor et al. | |
| 6,200,257 B1 | 3/2001 | Winkler | |
| 6,210,365 B1 | 4/2001 | Afzal | |
| 6,248,117 B1 | 6/2001 | Blatter | |
| 6,254,563 B1 | 7/2001 | Macoviak et al. | |
| 6,261,257 B1 | 7/2001 | Uffacker et al. | |
| 6,264,633 B1 | 7/2001 | Knorig | |
| 6,280,460 B1 | 8/2001 | Bolduc et al. | |
| 6,293,965 B1 | 9/2001 | Berg et al. | |
| 6,319,226 B1 | 11/2001 | Sherry | |
| 6,401,721 B1 | 6/2002 | Maginot | |
| 6,595,941 B1 * | 7/2003 | Blatter | 604/4.01 |
| 6,656,151 B1 * | 12/2003 | Blatter | 604/96.01 |
| 6,663,590 B1 * | 12/2003 | Blatter | 604/103.01 |
| 6,746,459 B1 | 6/2004 | Kato | |
| 2002/0049459 A1 | 4/2002 | Kato | |

FOREIGN PATENT DOCUMENTS

WO  WO 98/19634  5/1998

OTHER PUBLICATIONS

Clark Biocompatible Hemoperfusion System and Block Cutter, *Some Other Products from Clark Research, Clark® Biocompatible Hemoperfusion*, located at http://www.clarkrd.com/crd_other2.htm, 10 pgs., printed Jun. 24, 2003.

HGSA, *Medicare Medical Policy Bulletin, Policy S-107: Hemoperfusion, Bulletin, Freedom of Information*, located at http://www.hgsa.com/professionals/policy/s107.html, 1 pg., printed Jun. 24, 2003.

Facts about Plasmapheresis, *Plasmapheresis and Autoimmune Disease*, MDA Publications, located at http://www.mdausa.org/publications/fa-plasmaph.html, 4 pgs., printed Apr. 16, 2003.

Publications, *Hemodialysis*, located at http://www.rein.ca/hem-e.htm, 4 pgs., printed Apr. 16, 2003.

Tennessee Kidney Clinics and Affiliates, *What is Hemodialysis?* located at http://www.dialysisclinics.com/hemo.htlm, 2 pgs., printed Jun. 24, 2003.

*Good Nutrition & Hemodialysis*, located at http://www.nyu.edu/classes/compnutrfood/Cecilia%20Fong/index.html 1 pg., printed Jun. 24, 2003.

Mulzer, S.R. and Brash, J.L., *Identification of Plasma Proteins Adsorbed to Hemodialyzers During Clinical Use*, Journal of Biomedical Materials Research, vol. 23, 1483-1504 (1989).

Ljungberg, B., et al., *Effective Anticoagulation by a Low Molecular Weight Heparin (Fragmin®) in Hemodialysis with a Highly Permeable Polysulfone Membrane*, Clinical Nephrology, vol. 38, No. 2-1992 (97-100).

Jen Ming Yang, et al., *Preparation of Heparin Containing SBS-g-VP Copolymer Membrane for Biomaterial Usage*, Journal of Membrane Science 138 (1998) 19-27.

Office Action dated Sep. 20, 2005 in U.S. Appl. No. 10/624,315, 7 pgs.

Interview Summary from Oct. 18, 2005 in U.S. Appl. No. 10/624,315, 1 pg.

Office Action Response dated Dec. 16, 2005 in U.S. Appl. No. 10/624,315, 19 pgs.

Office Action dated Sep. 29, 2005 in U.S. Appl. No. 10/624,711, 7 pgs.

Interview Summary from Oct. 18, 2005 in U.S. Appl. No. 10/624,711, 1 pg.

Office Action Response dated Dec. 15, 2005 in U.S. Appl. No. 10/624,711, 16 pgs.

Office Action dated Jan. 12, 2006 in U.S. Appl. No. 10/351,172, 2 pgs.

Office Action Response dated Feb. 10, 2006 in U.S. Appl. No. 10/351,172, 12 pgs.

Office Action dated Aug. 18, 2005 in U.S. Appl. No. 10/351,172, 5 pgs.

Interview Summary from Oct. 18, 2005 in U.S. Appl. No. 10/351/172, 1 pg.

Office Action Response dated Dec. 16, 2005 in U.S. Appl. No. 10/351,172, 21 pgs.

Office Action dated Jan. 29, 2002 in U.S. Appl. No. 09/481,283 (Patent No. 6,595,941), 7 pgs.

Interview Summary from Jun. 13, 2002 in U.S. Appl. No. 09/481,283 (Patent No. 6,595,941), 1 pg.

Office Action Response dated Jul. 1, 2002 in U.S. Appl. No. 09/481,283 (Patent No. 6,595,941), 13 pgs.

Office Action dated Sep. 25, 2002 in U.S. Appl. No. 09/760,322 (Patent No. 6,663,590), 9 pgs.

Interview Summary from Nov. 21, 2002 in U.S. Appl. No. 09/760,322 (Patent No. 6,663,590), 1 pg.

Office Action Response dated Mar. 25, 2003 in U.S. Appl. No. 09/760,322 (Patent No. 6,663,590), 31 pgs.
Office Action dated Jun. 18, 2003 in U.S. Appl. No. 09/760,322 (Patent No. 6,663,590), 4 pgs.
Office Action Response dated Jun. 26, 2003 in U.S. Appl. No. 09/760,322 (Patent No. 6,663,590), 2 pgs.
Office Action (Election/Restrictions) dated Apr.10, 2001 in U.S. Appl. No. 09/480,964 (Patent No. 6,656,151), 4 pgs.
Response to Restriction Requirement dated Jul. 10, 2001 in U.S. Appl. No. 09/480,964, (Patent No. 6,656,151) 2 pgs.
Office Action dated Sep. 13, 2001 in U.S. Appl. No. 09/480,964 (Patent No. 6,656,151), 6 pgs.
Office Action Response dated Mar. 13, 2002 in U.S. Appl. No. 09/480,964 (Patent No. 6,656,151), 8 pgs.
Interview Summary from Mar. 13, 2002 in U.S. Appl. No. 09/480,964 (Patent No. 6,656,151), 1 pg.
Final Office Action dated Apr. 9, 2002 in U.S. Appl. No. 09/480,964 (Patent No. 6,656,151), 7 pgs.
Final Office Action dated Oct. 1, 2002 in U.S. Appl. No. 09/480,964 (Patent No. 6,656,151), 7 pgs.
Interview Summary from Nov. 21, 2002 in U.S. Appl. No. 09/480,964 (Patent No. 6,656,151), 1 pg.
Office Action Response dated Apr. 1, 2003 in U.S. Appl. No. 09/480,964 (Patent No. 6,656,151), 36 pgs.
Interview Summary from May 6, 2003 in U.S. Appl. No. 09/480,964 (Patent No. 6,656,151), 1 pg.

* cited by examiner

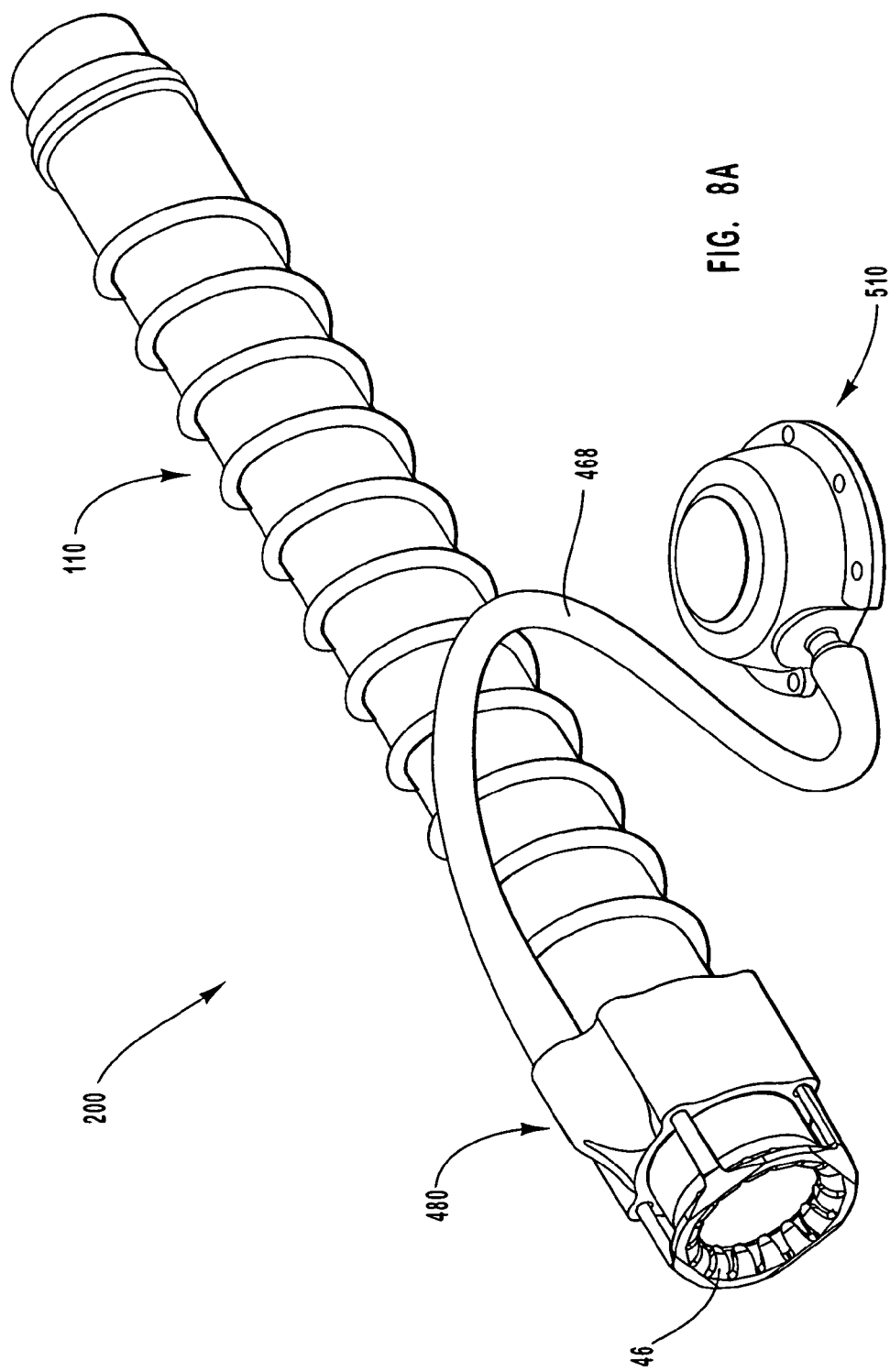

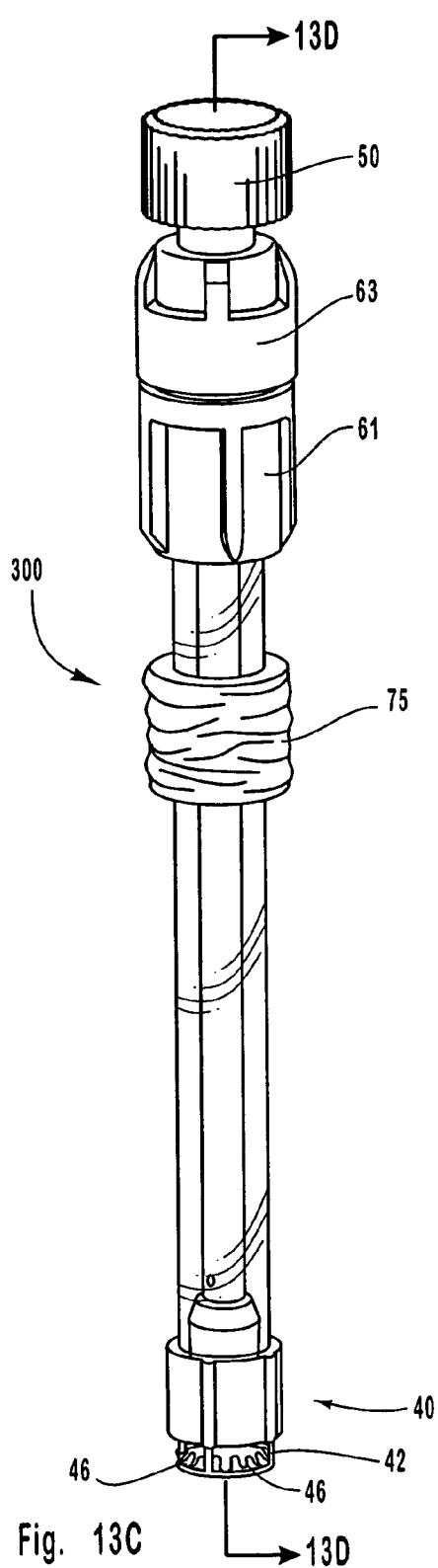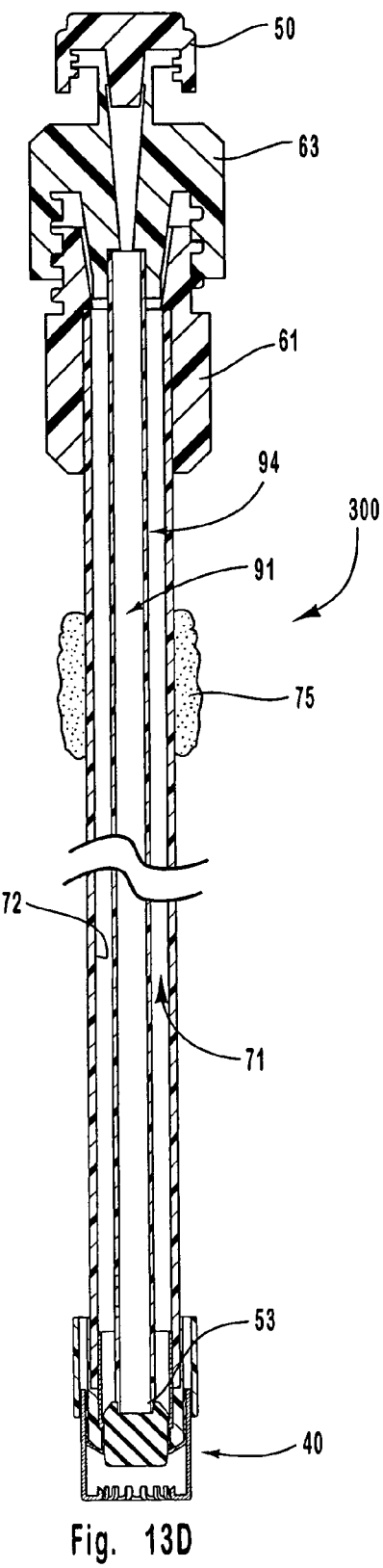
Fig. 13C
Fig. 13D

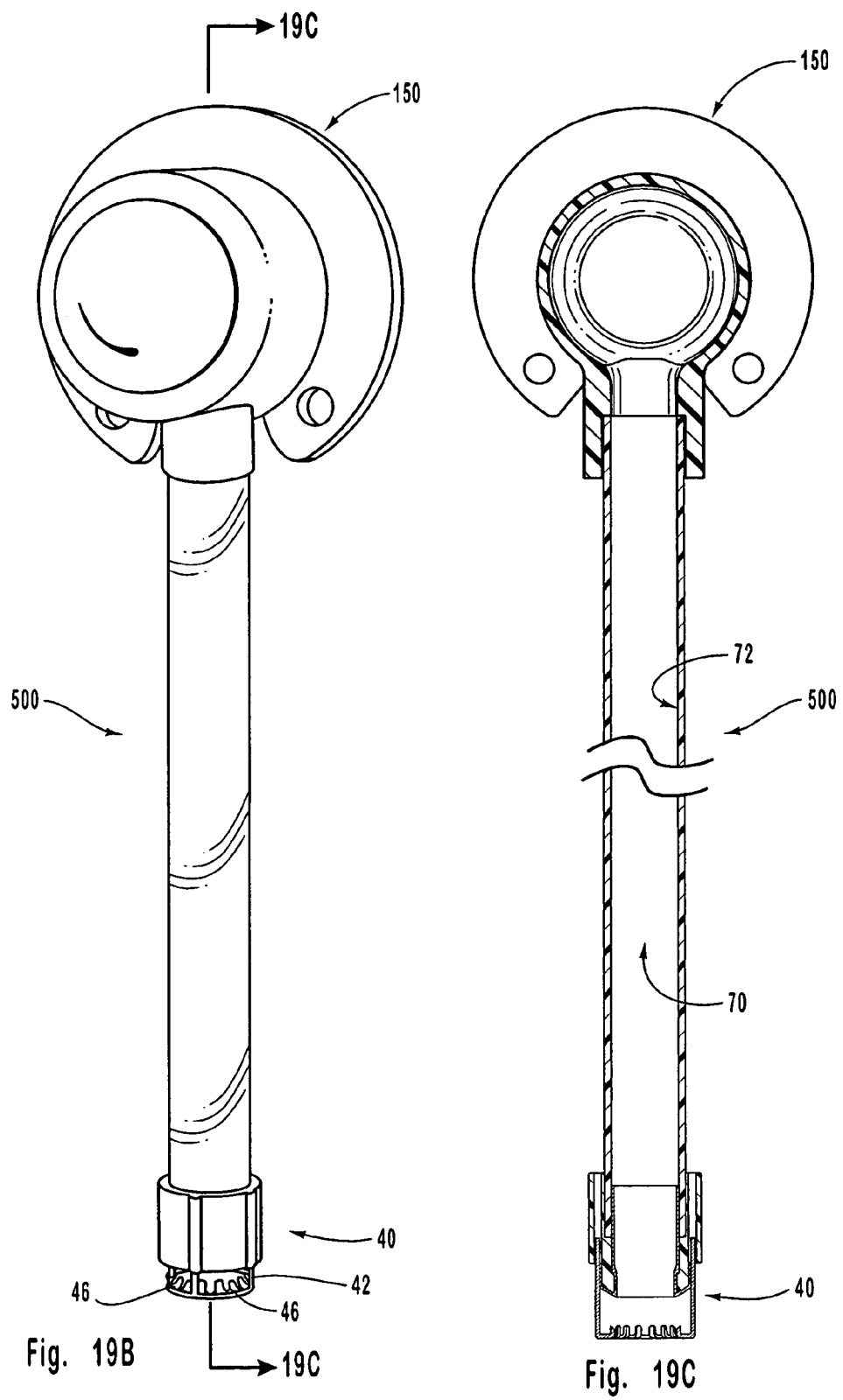

APPARATUS AND METHODS FOR FACILITATING REPEATED VASCULAR ACCESS

RELATED APPLICATIONS

This is a continuation-in-part of U.S. patent application Ser. No. 09/481,283, which was filed on Jan. 11, 2000 and issued on Jul. 22, 2003 as U.S. Pat. No. 6,595,941. This is also a continuation-in-part of U.S. patent application Ser. No. 09/760,322, filed on Jan. 11, 2001, now U.S. Pat. No. 6,663,590, which is a continuation-in-part of application Ser. No. 09/480,964, filed on Jan. 11, 2000, now U.S. Pat. No. 6,656,151. This is additionally a continuation-in-part of U.S. patent application Ser. No. 10/351,172, which was filed on Jan. 23, 2003. Each of these Applications is hereby incorporated by specific reference.

SUMMARY OF THE INVENTION

The present invention provides methods and apparatus for facilitating long-term, repeated access to a body fluid such as blood.

This is achieved by providing one or more occludable access tubes that are adapted for anastomosis to an anatomical vessel. After a hole is formed in the sidewall of the target vessel, the access tube can be anastomosed to the vessel using any desired method, including suturing, stapling, clamping, welding, adhesives, etc. Optionally, an anastomosis component or device can be used to assist in the anastomosis procedure.

Once anastomosed to the vessel sidewall, the access tube is occluded with any of various occluders as disclosed herein. The occluder prevents body fluid from the vessel from entering the conduit until access to the body fluid in the vessel is desired. After fluid communication is enabled via the access tube, the occluder may then be moved or replaced to reocclude the access tube.

One method of the invention utilizes two of the access tubes discussed, one being used for extracting a body fluid from the vessel and the other used for inserting the body fluid back into the vascular system. The second access tube used to insert the body fluid can be anastomosed to the same vessel at a separate location or, alternatively, it can be anastomosed to a separate vessel.

While two access tubes are typically used, it is also possible to use a single access tube. A single access tube could also be used to both withdraw and insert a fluid. For example, only one access tube would be necessary for withdrawing particularized amounts of blood for testing, etc., or for inserting medications or other pharmacological agents into a patient's bloodstream or other vascular system.

Additional aspects and advantages of this invention will be apparent from the following detailed description of preferred embodiments, which proceeds with reference to the accompanying drawings.

BRIEF DESCRIPTIONS OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 is a partial cross-sectional view of an embodiment of a vascular access system with a balloon occluder.

FIG. 2A is a partial cross-sectional view of a balloon occluder in an access tube that is coupled to a port device. The balloon has a semipermeable membrane at its delivery end and is coupled to a port device at its other end. The balloon is inflated.

FIG. 2B is a partial cross-sectional view of the system shown in FIG. 2A with the balloon deflated to allow for vascular access.

FIGS. 3A–3D schematically illustrate different configurations of a semipermeable membrane at the delivery end of a balloon occluder.

Figure 6:
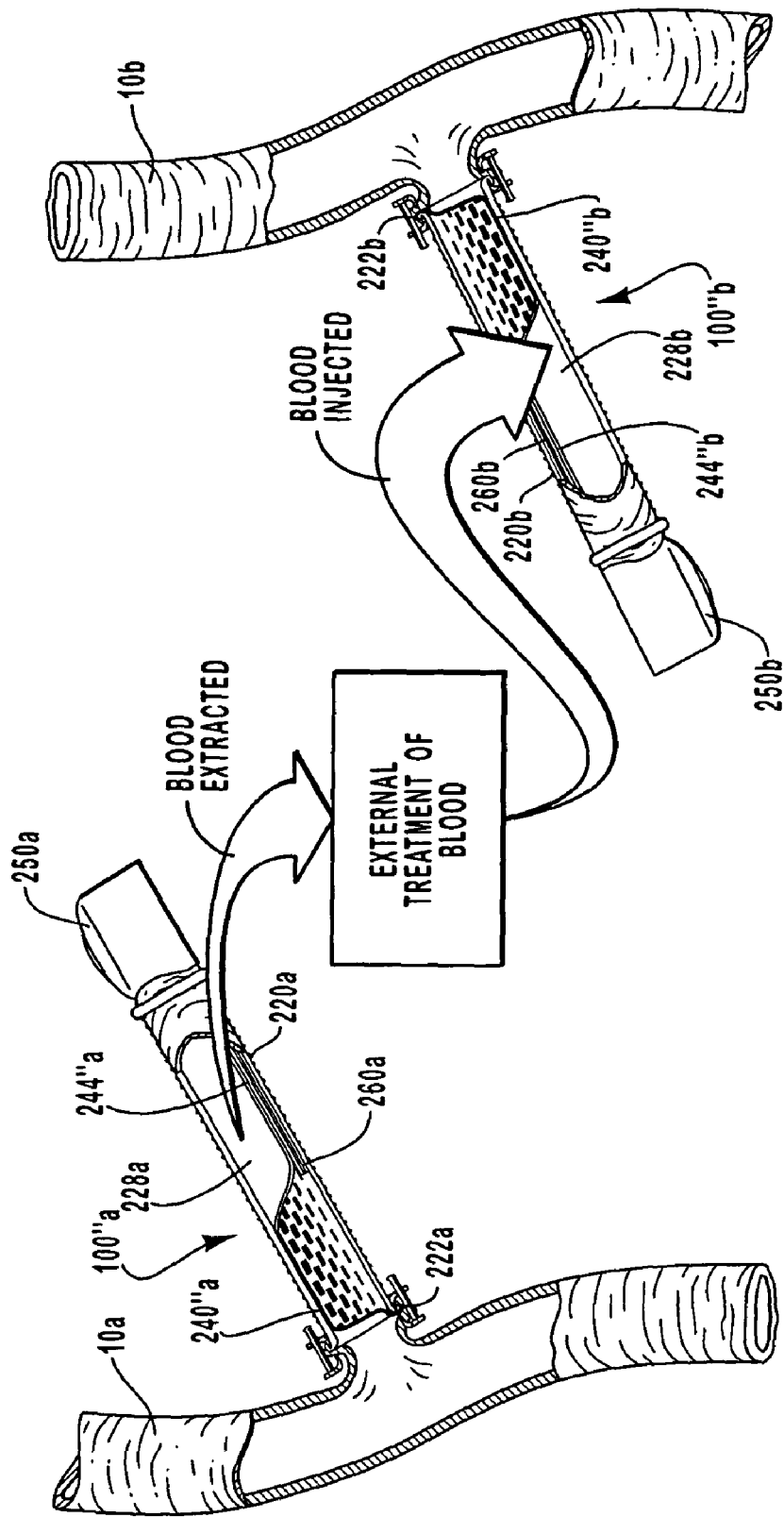

FIG. 6 schematically shows the practice of hemodialysis with a balloon occluder in an access tube.

Figure 7A:
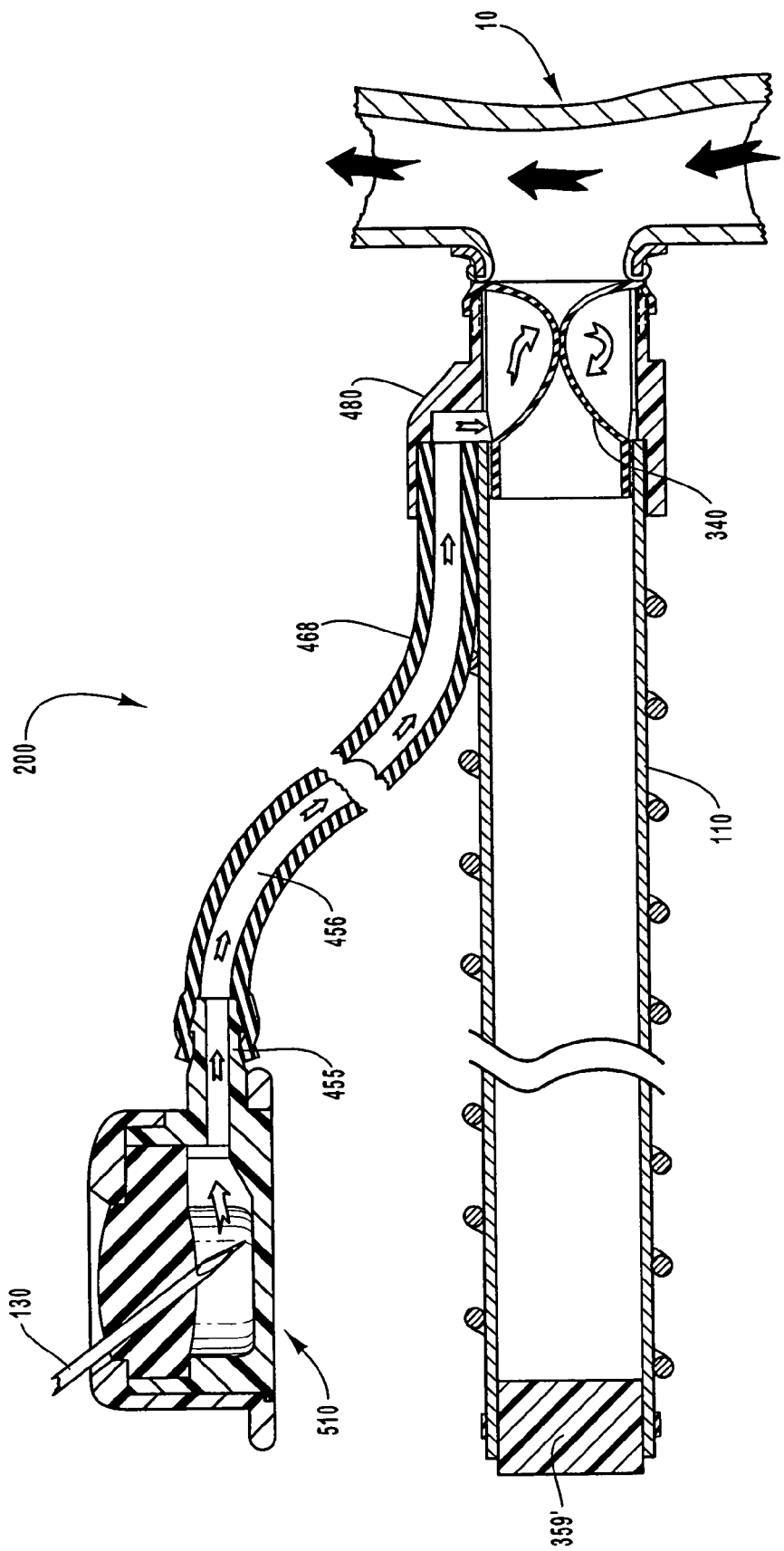

FIG. 7A is a partial cross-sectional view of an embodiment of a vascular access system with a toroidal-shaped balloon occluder coupled to a port device by way of a port tube connected to the access tube.

Figure 7B:
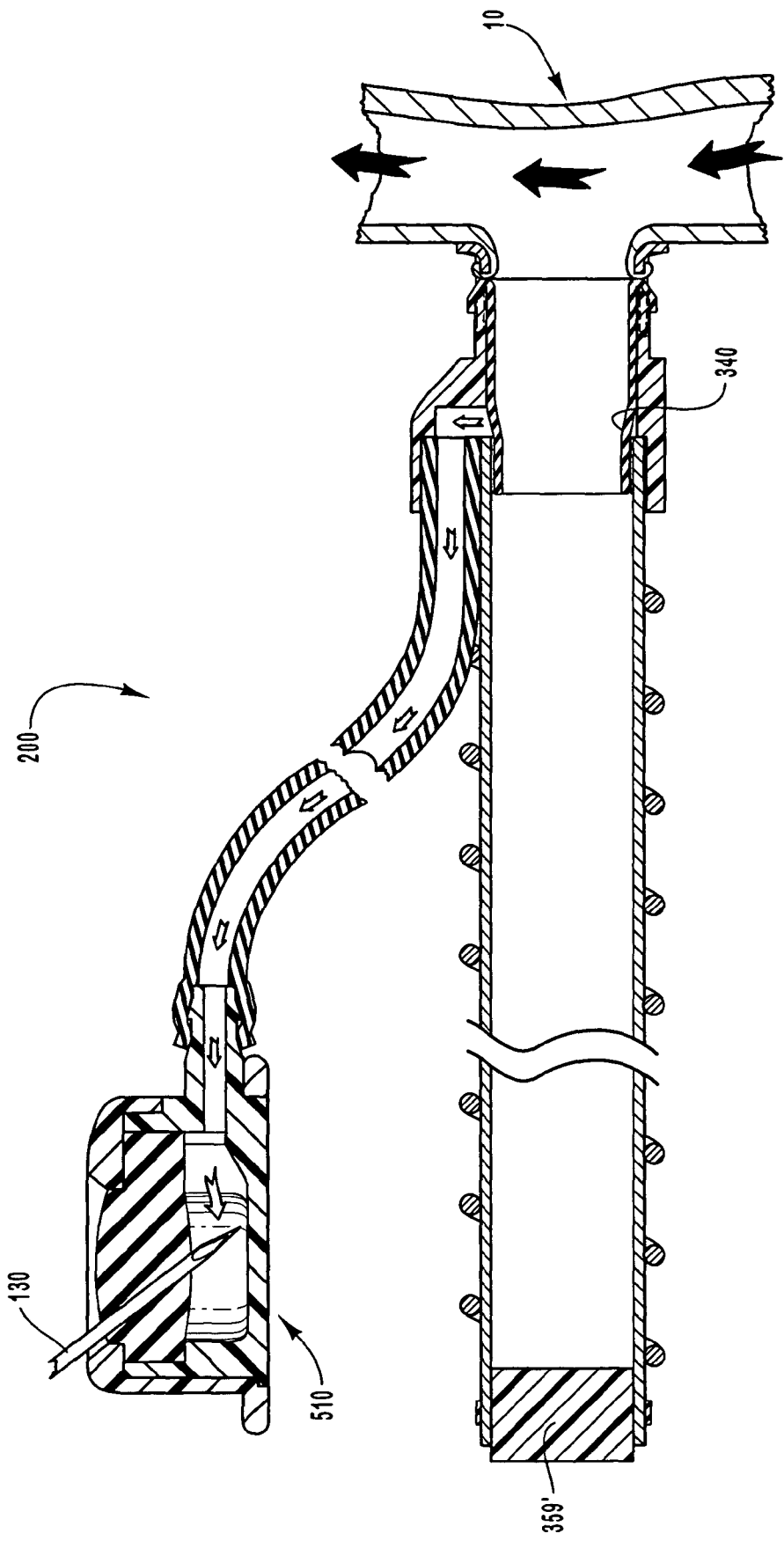

FIG. 7B is a partial cross-sectional view of the embodiment shown in FIG. 7A with the balloon deflated to allow for vascular access.

Figure 7C:
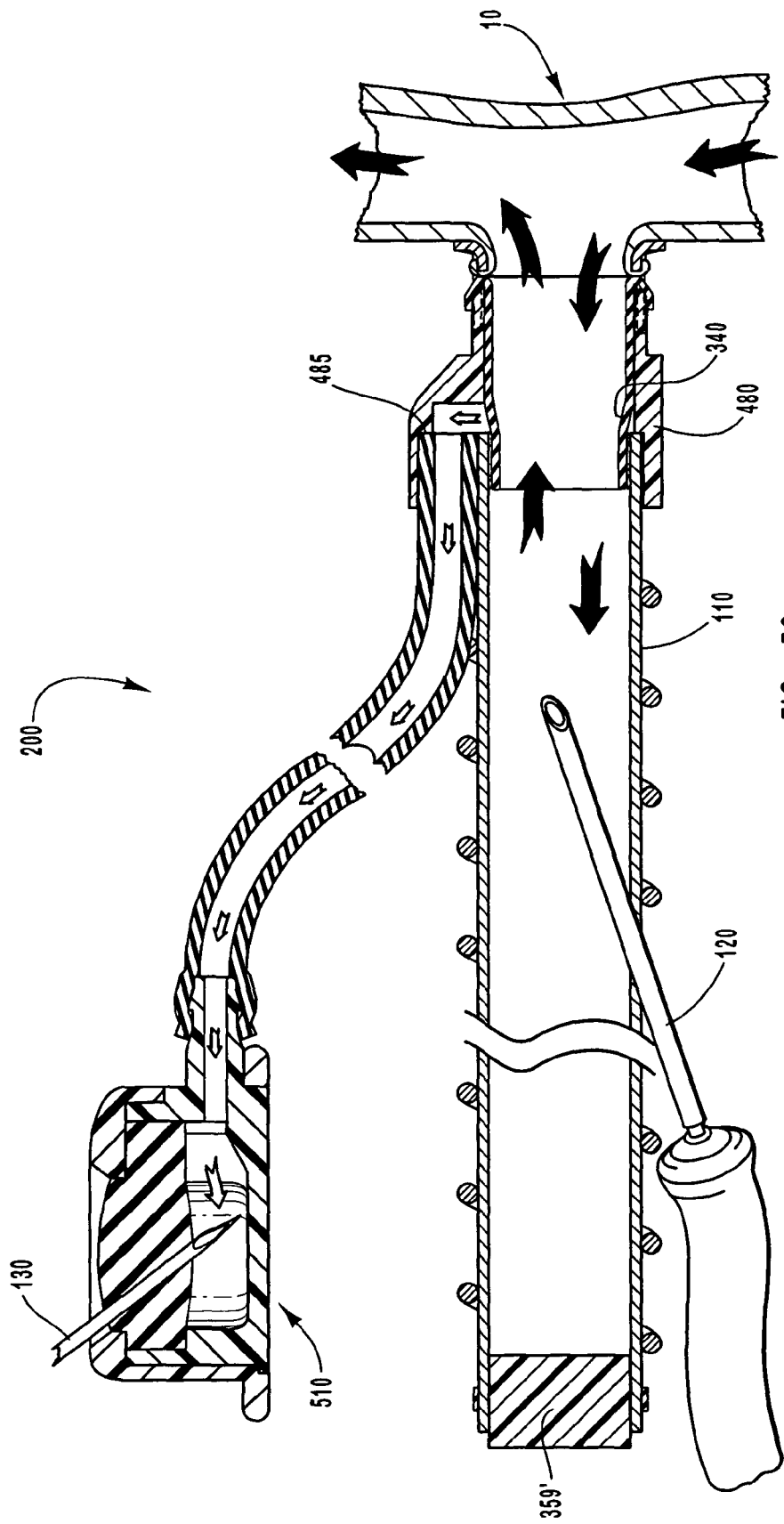

FIG. 7C is a partial cross-sectional view of the embodiment shown in FIG. 7B with a needle inserted into the access tube to obtain access to the body fluid in the vessel.

FIG. 8A is a perspective view of the access tube device shown in FIGS. 7A–7C.

Figure 8B:
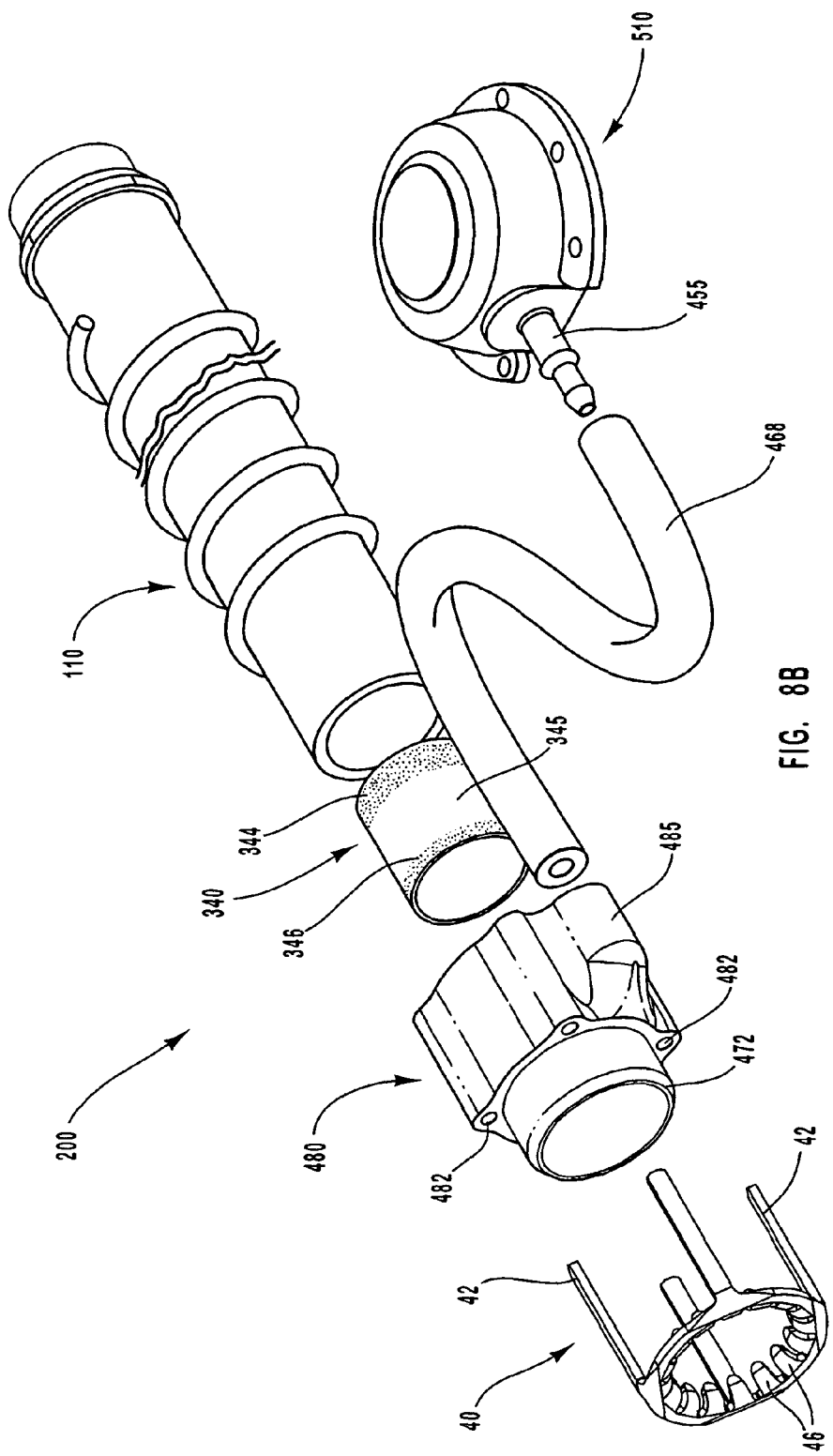

FIG. 8B is an exploded perspective view of the access tube device shown in FIG. 8A.

Figure 9:
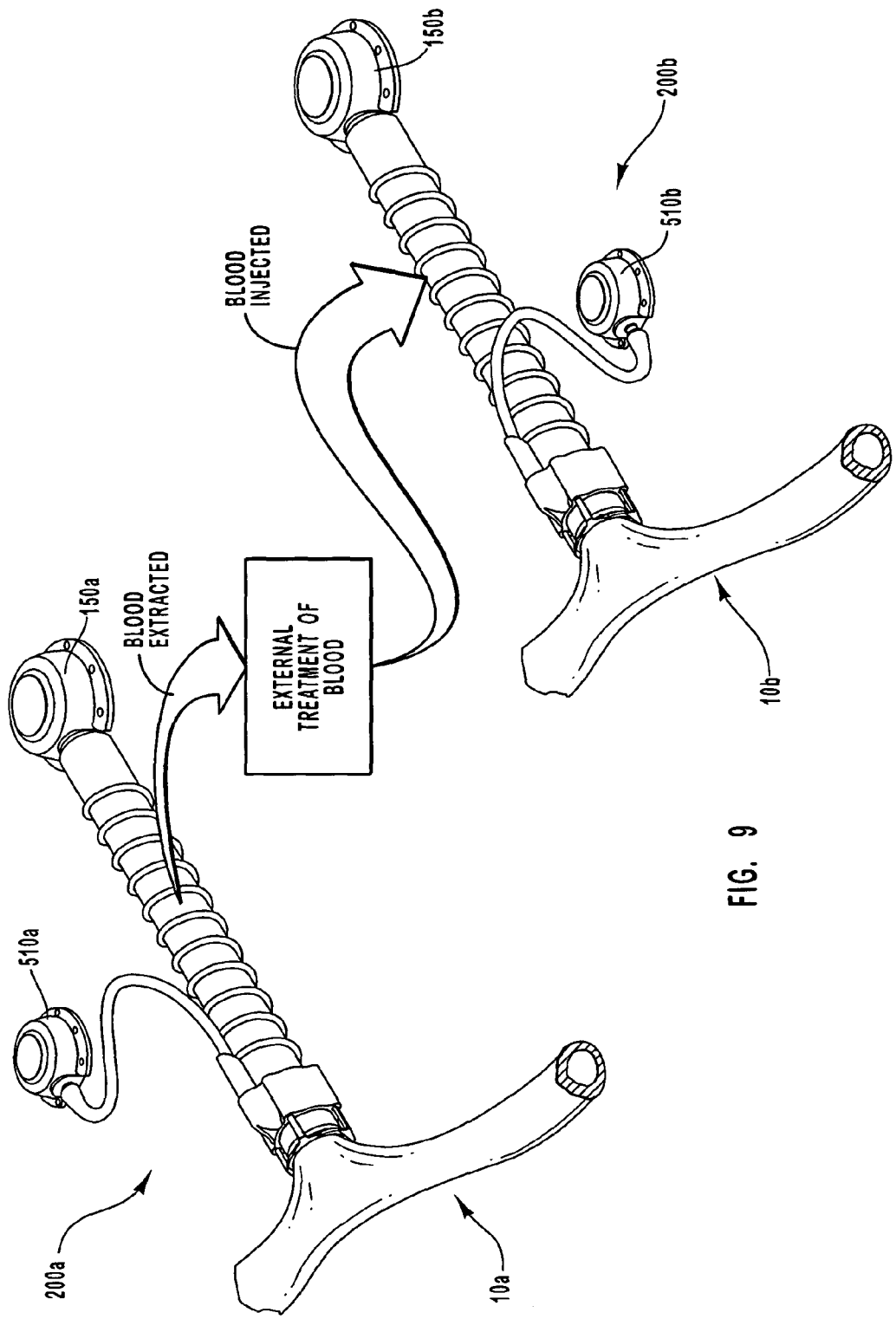

FIG. 9 schematically shows the practice of hemodialysis with the access tube device depicted in FIGS. 8A–8B.

Figure 10:
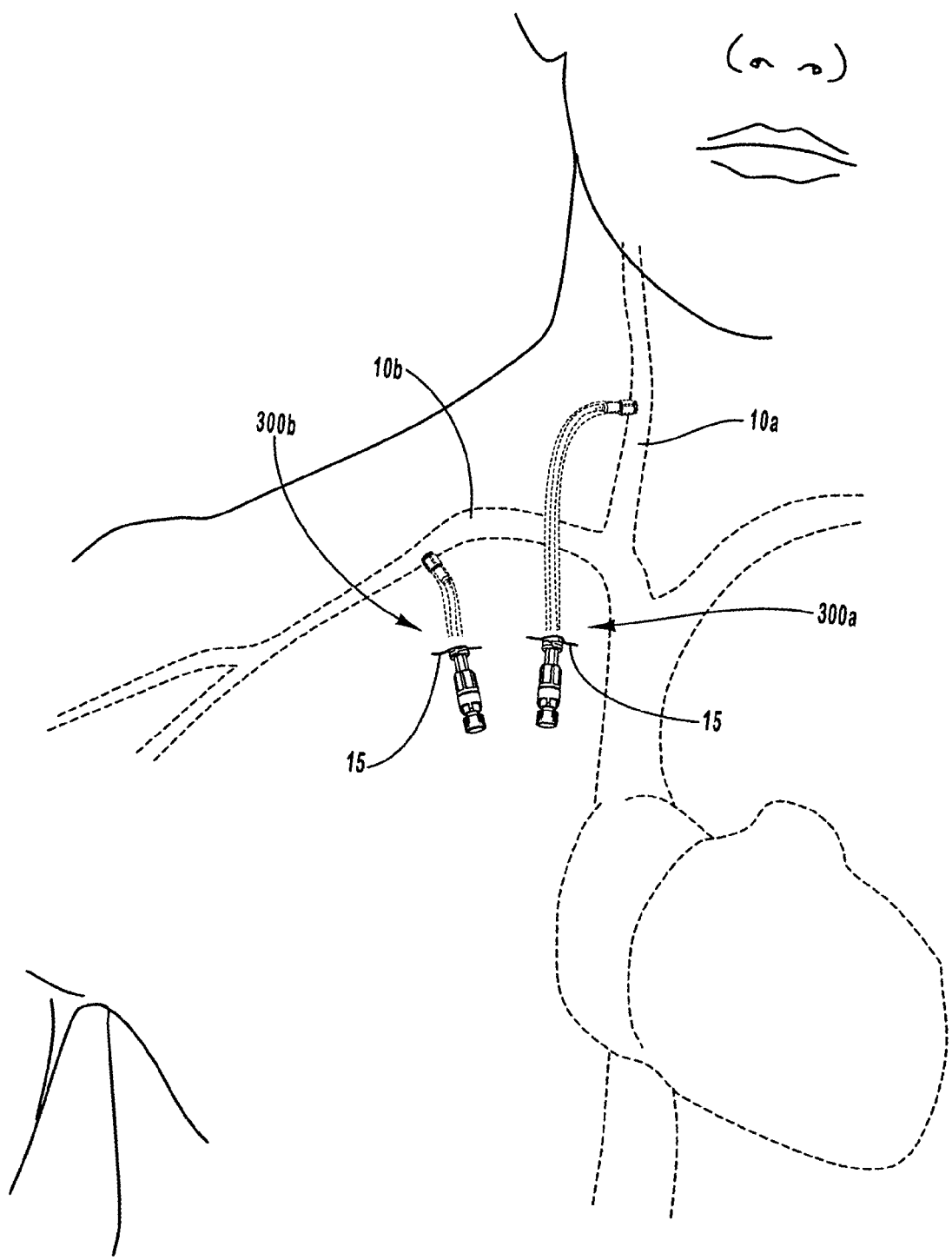

FIG. 10 is a perspective view of an embodiment of two access tube devices attached to a patient's blood vessels and protruding from the patient's skin.

Figure 11A:
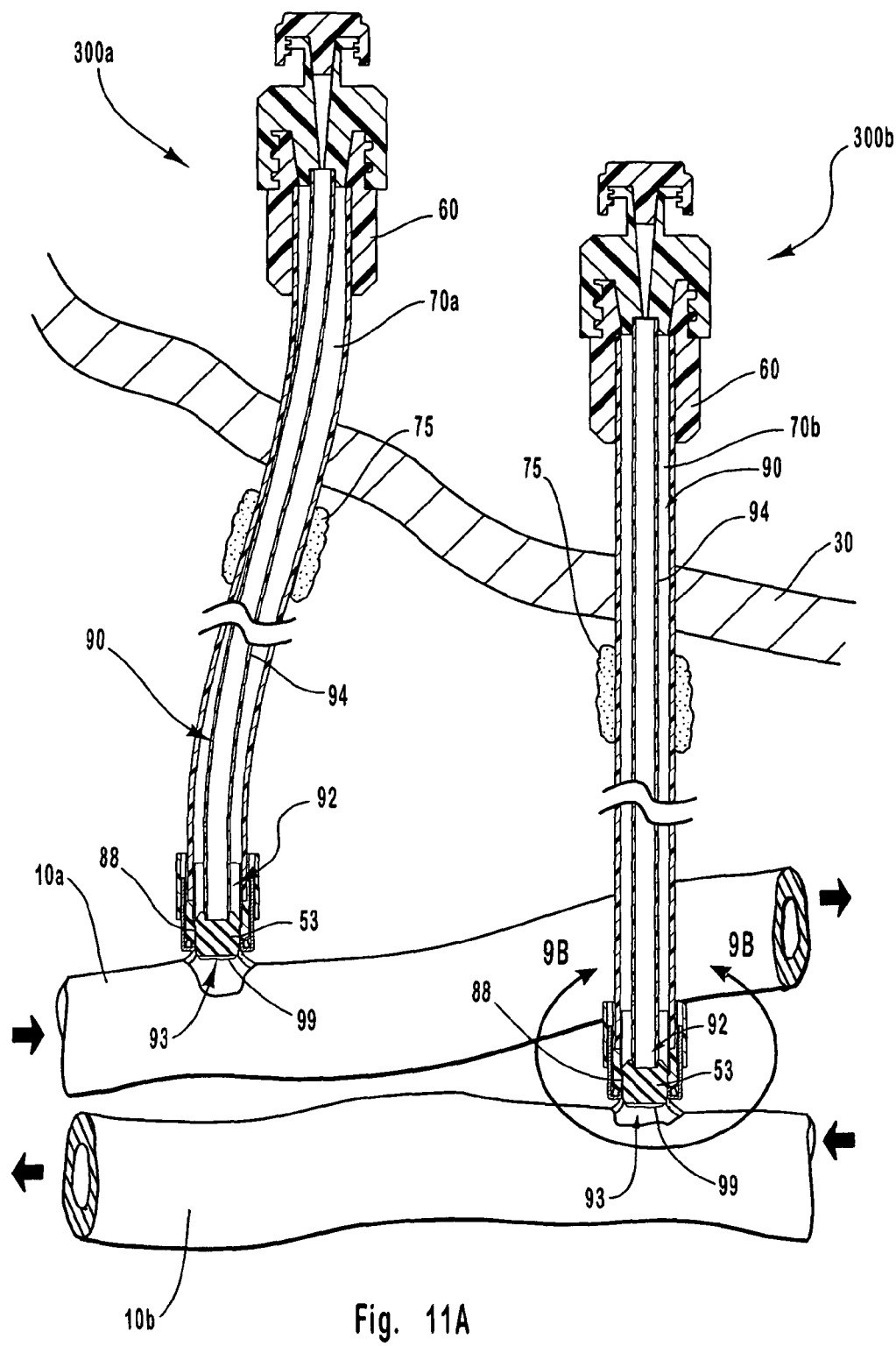

FIG. 11A is a partial cross-sectional view of two of the access tube devices shown in FIG. 10 with their occluders fully positioned inside their respective access tubes, attached to separate blood vessels, and extending through the skin.

Figure 11B:
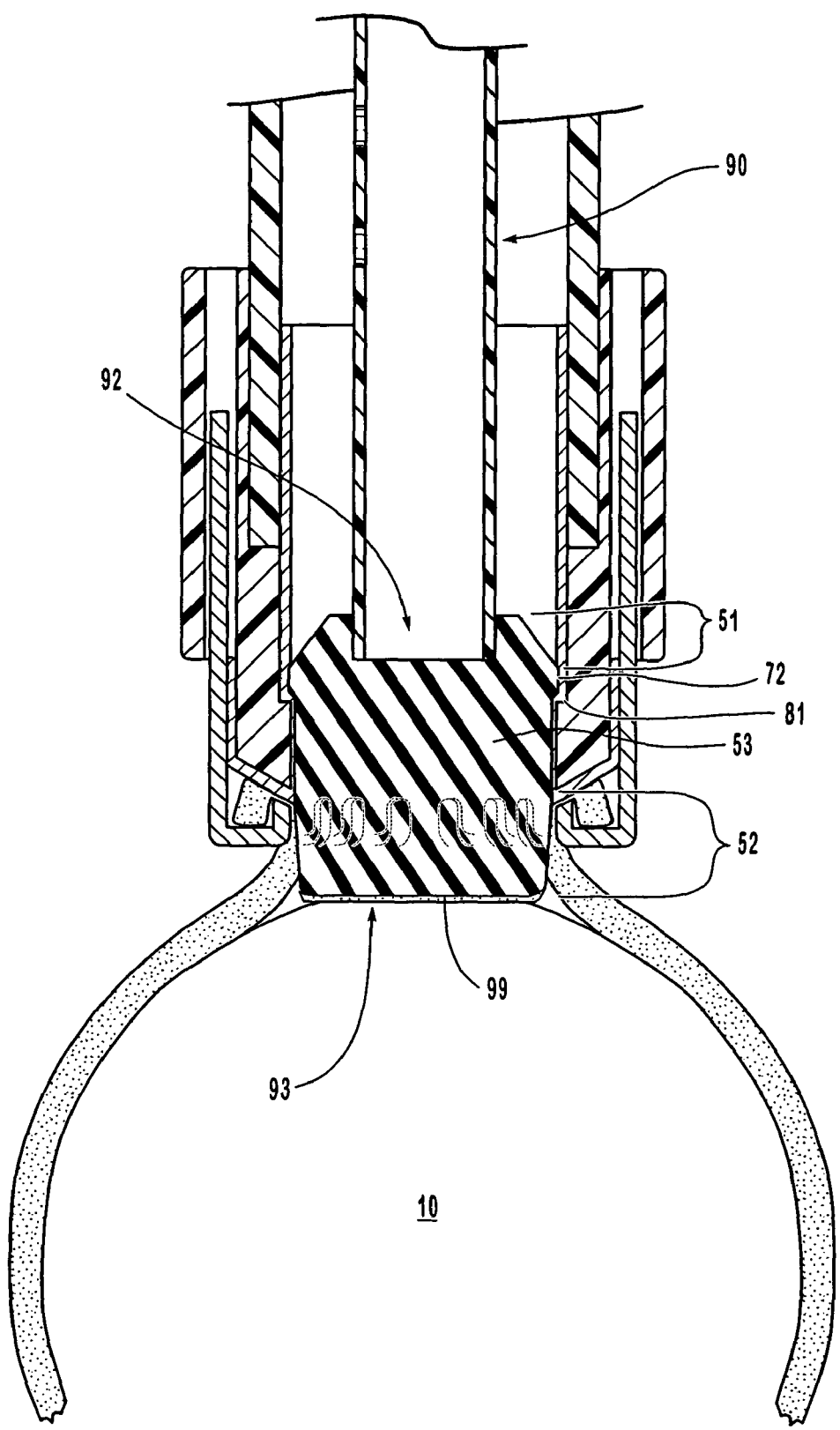

FIG. 11B is an enlarged cross-sectional view of the interface between the occlusion end of an access tube device with the occluder positioned therein and the target vessel wall.

Figure 11C:
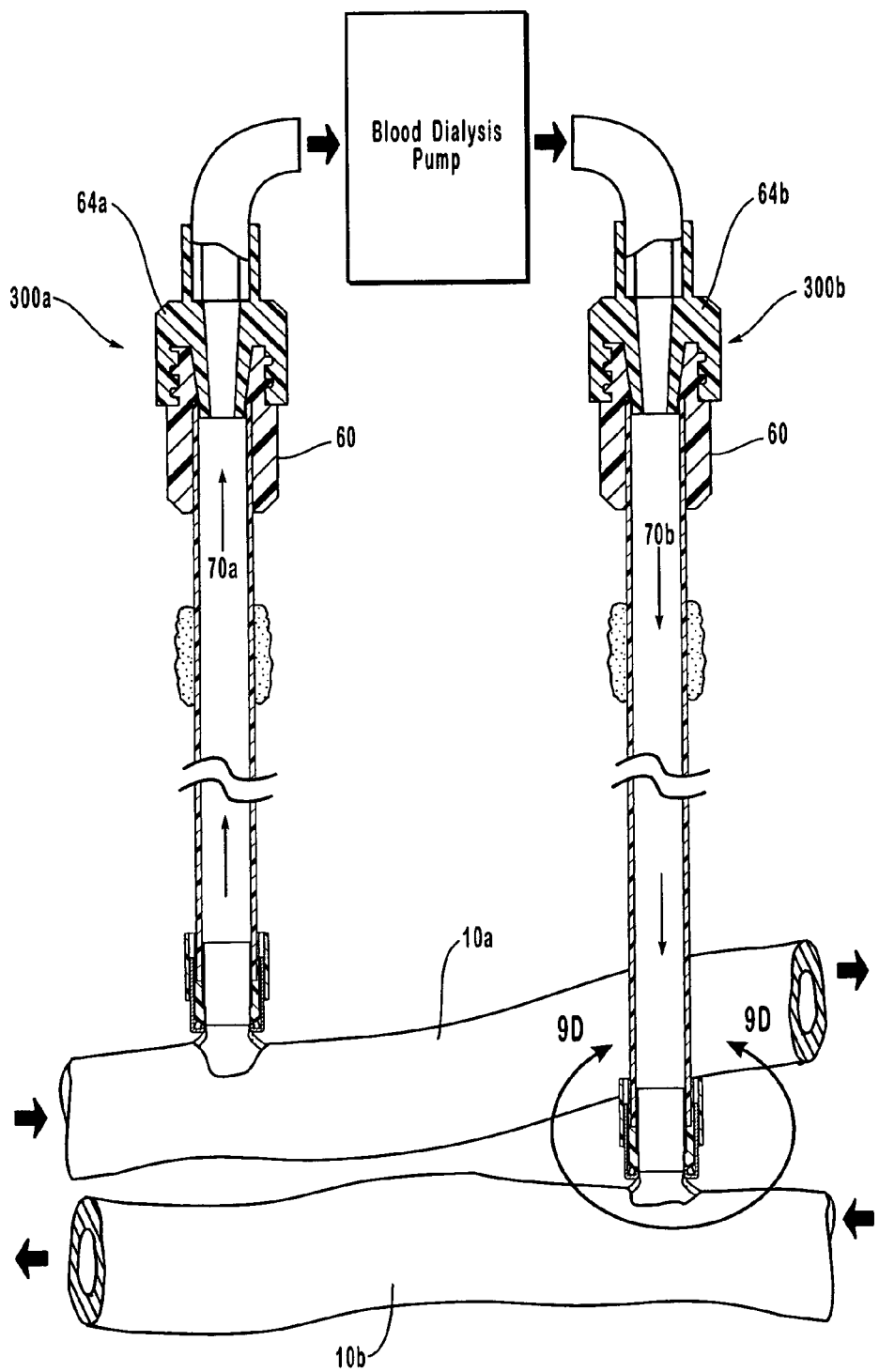

FIG. 11C is a partial cross-sectional view like that of FIG. 11A, but with the occluders withdrawn for blood treatment.

Figure 11D:
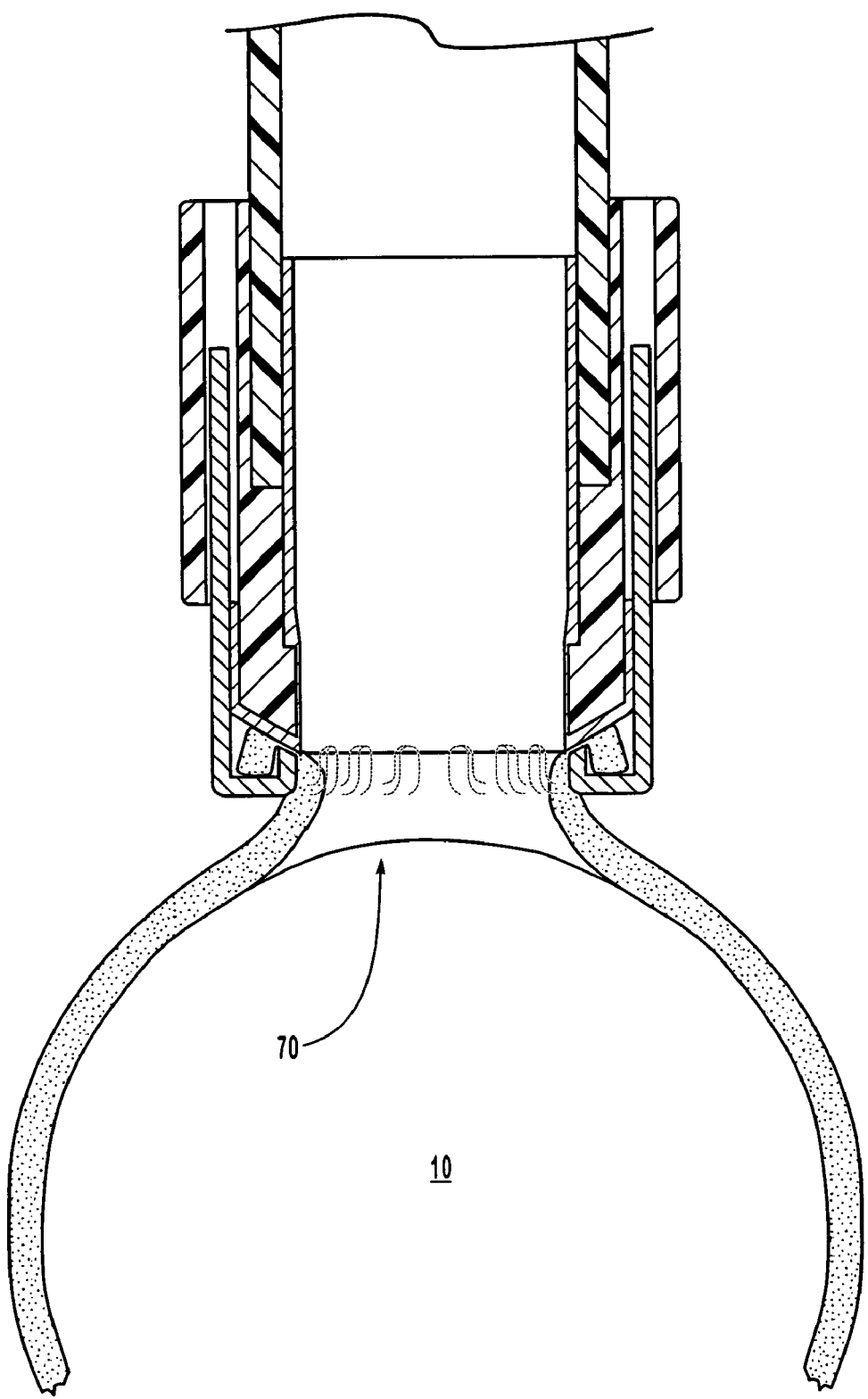

FIG. 11D is an enlarged cross-sectional view like that of FIG. 11B, but with the occluder withdrawn.

Figure 12:
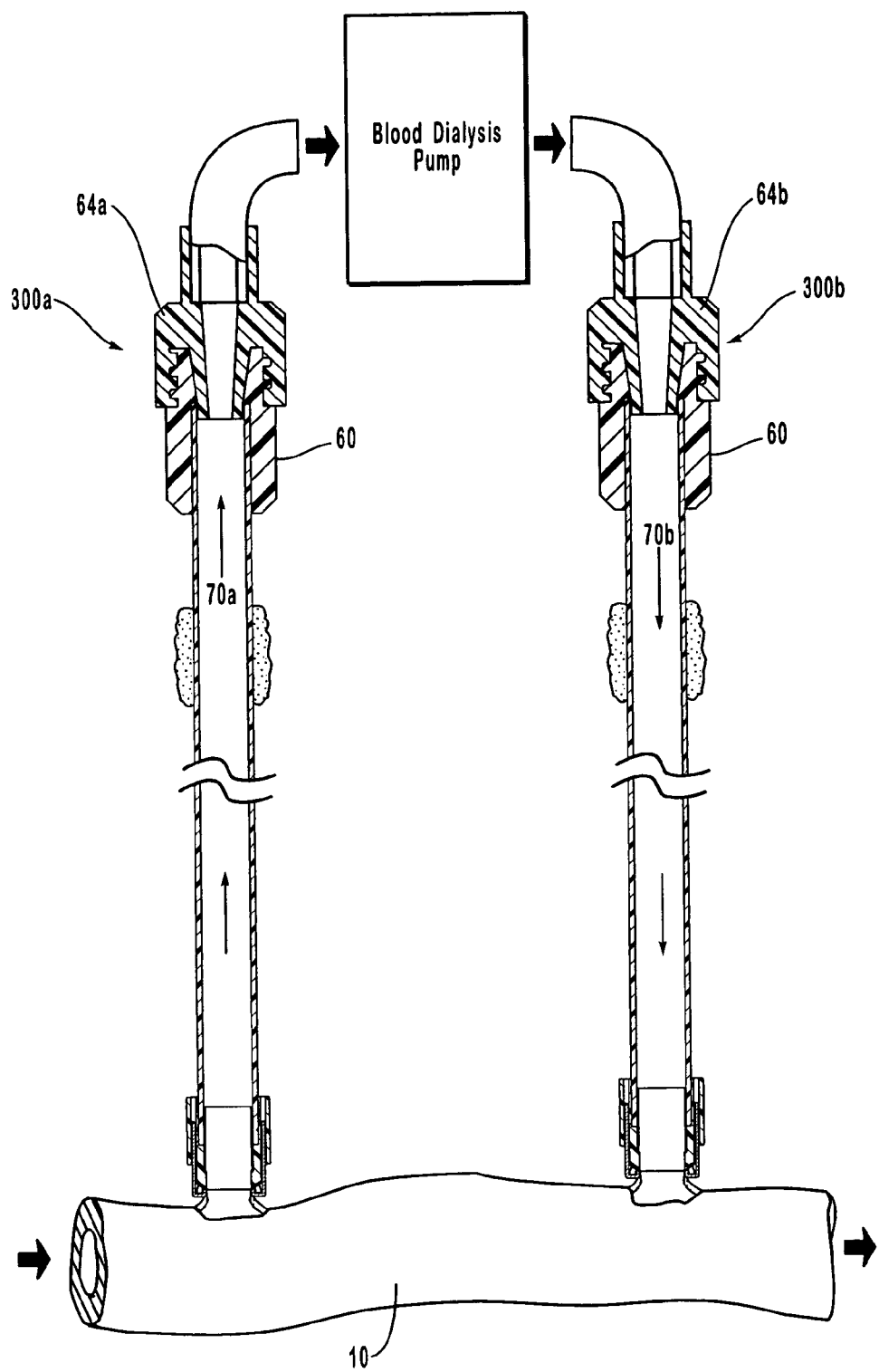

FIG. 12 is a partial cross-sectional view of the access tube devices attached to the same target vessel at two separate locations, again with their occluders withdrawn for blood treatment.

Figure 13A:
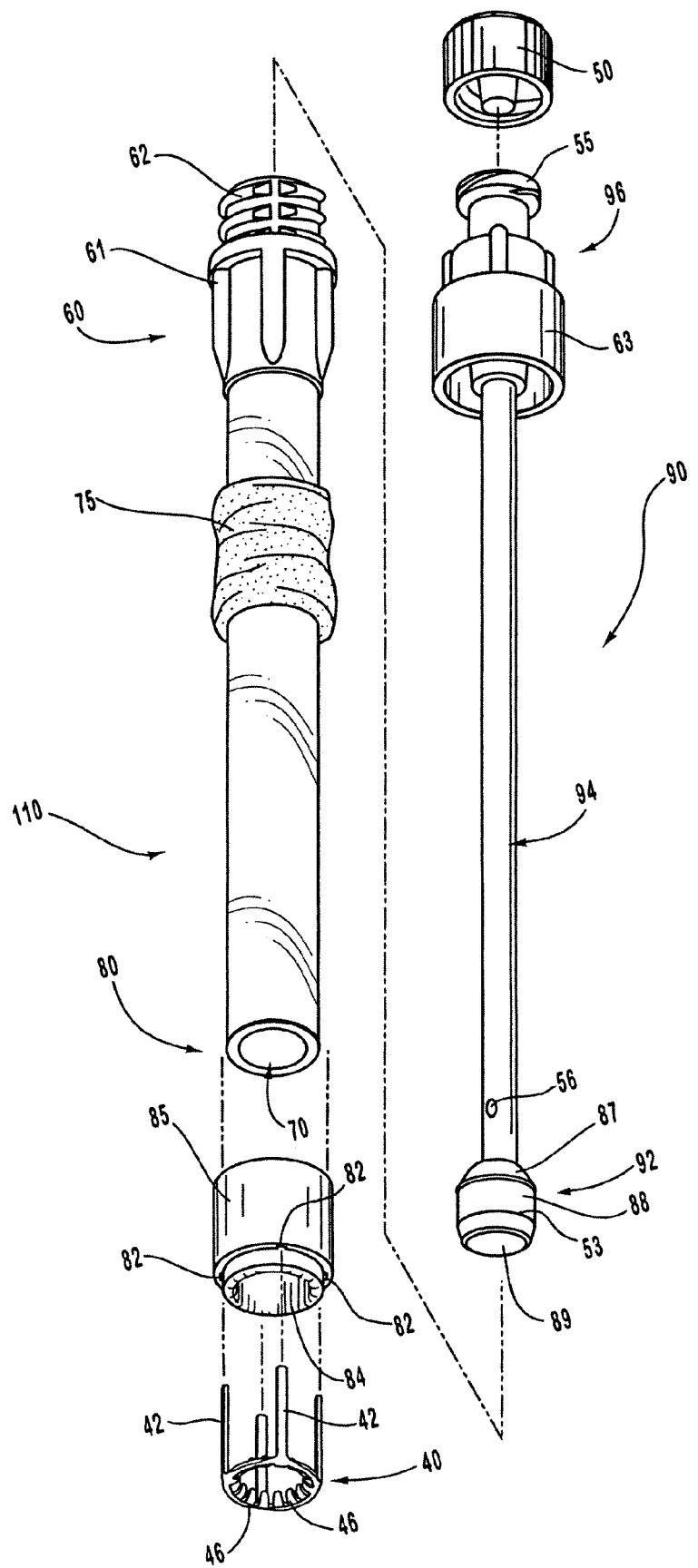

FIG. 13A is an exploded perspective view of the embodiment of an access tube device shown in FIG. 12.

Figure 13B:
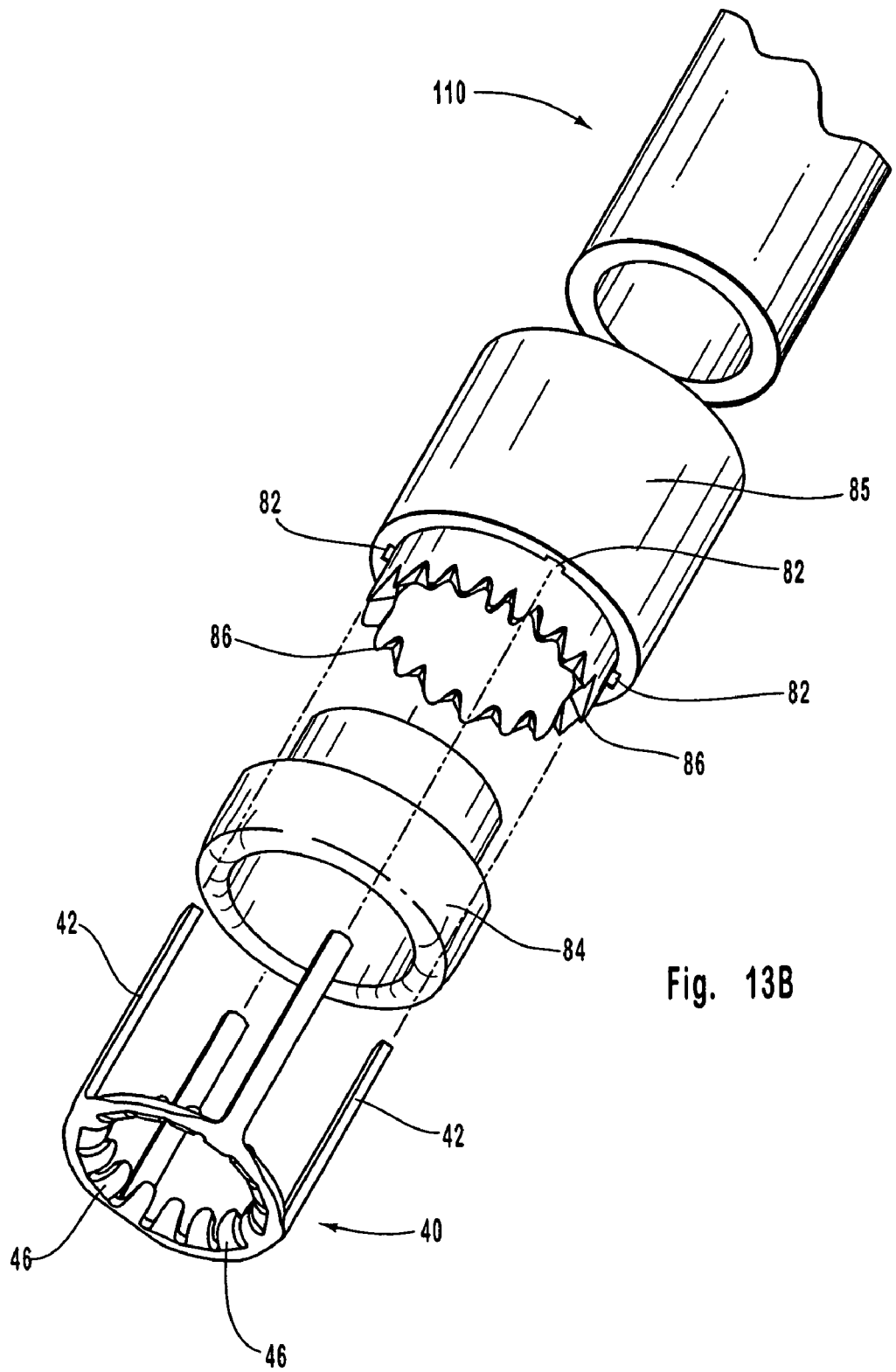

FIG. 13B is an enlarged, exploded perspective view of the anastomosis end of the device shown in FIG. 5B, but with the covering shown removed from the access tube anastomosis ring and exposing the access tube holding tabs.

FIG. 13C is a perspective view of the embodiment of an access tube device shown in FIGS. 13A–13B.

FIG. 13D is a cross-sectional view of the access tube device shown in FIG. 13C.

Figure 13E:
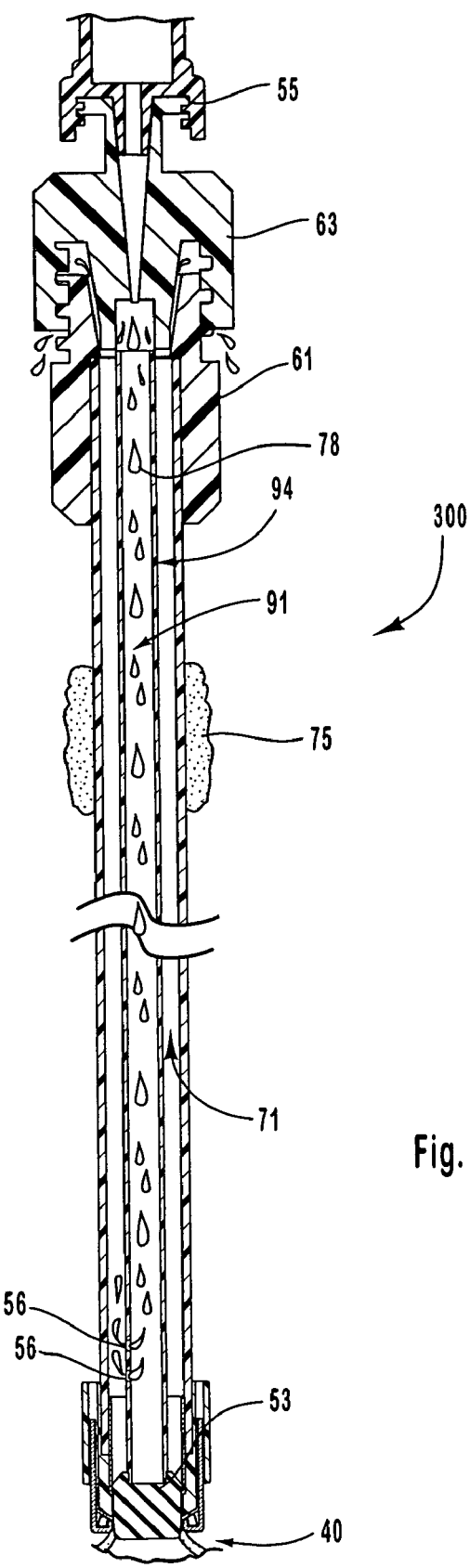

FIG. 13E is a cross-sectional view showing the flushing cap removed and flushing fluid introduced through the flushing conduit and into the chamber.

Figure 14:
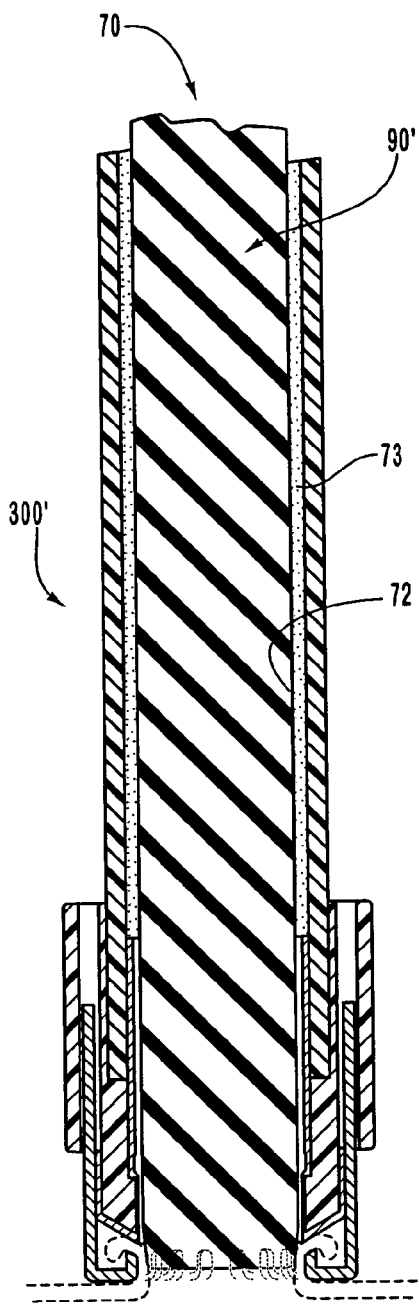

FIG. 14 is a cross-sectional view of an embodiment of the device employing a uniformly-shaped occluder with a coating.

Figure 15:
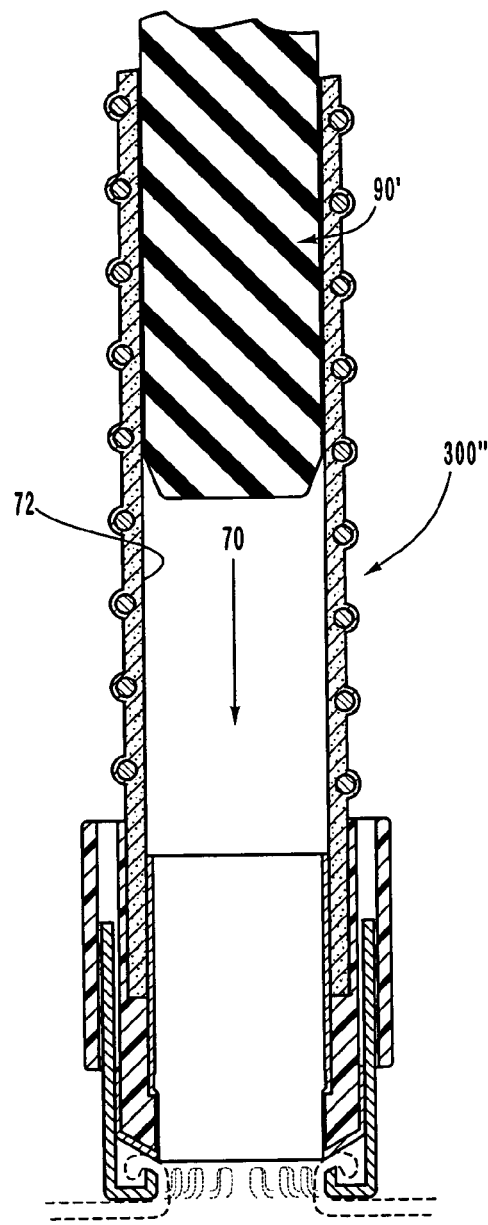

FIG. 15 is a cross-sectional view of an embodiment of the device wherein the access tube is a graft vessel and employing a uniformly-shaped occluder without a coating.

Figure 16A:
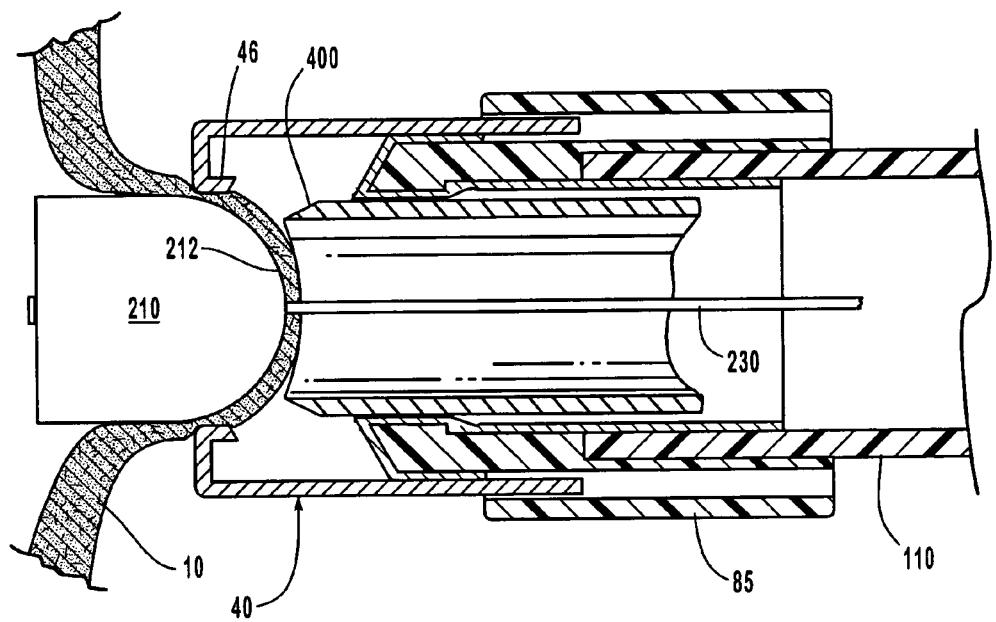

FIG. 16A is an enlarged cross-sectional view of an anvil apparatus distending the target vessel wall and the cutter of an external anastomosis operator being drawn towards the anvil apparatus.

Figure 16B:
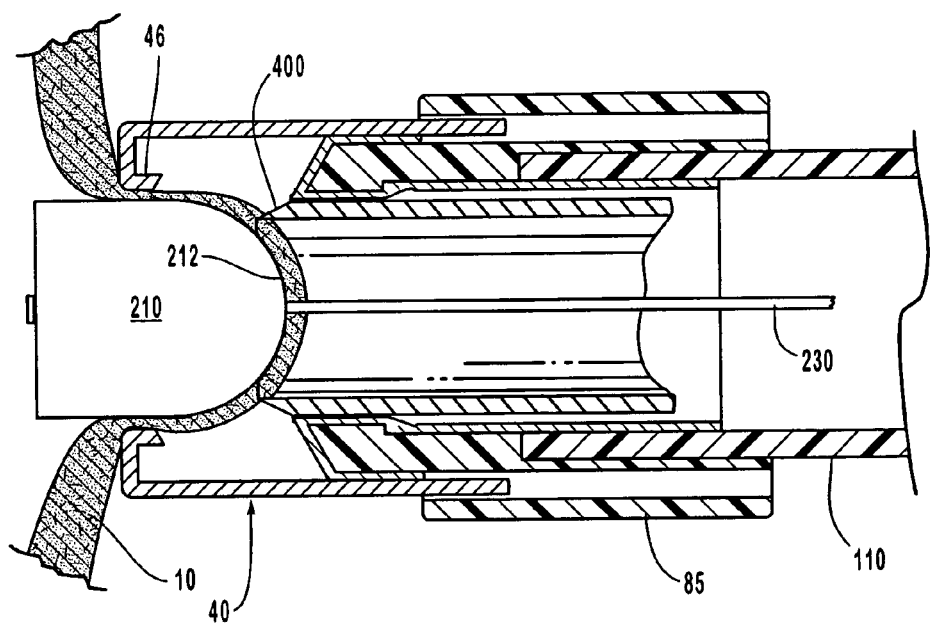

FIG. 16B is an enlarged cross-sectional view like that of FIG. 16A after the cutter has engaged the anvil apparatus to cut the target vessel wall and evert the target vessel tissue over the holding tabs.

Figure 16C:
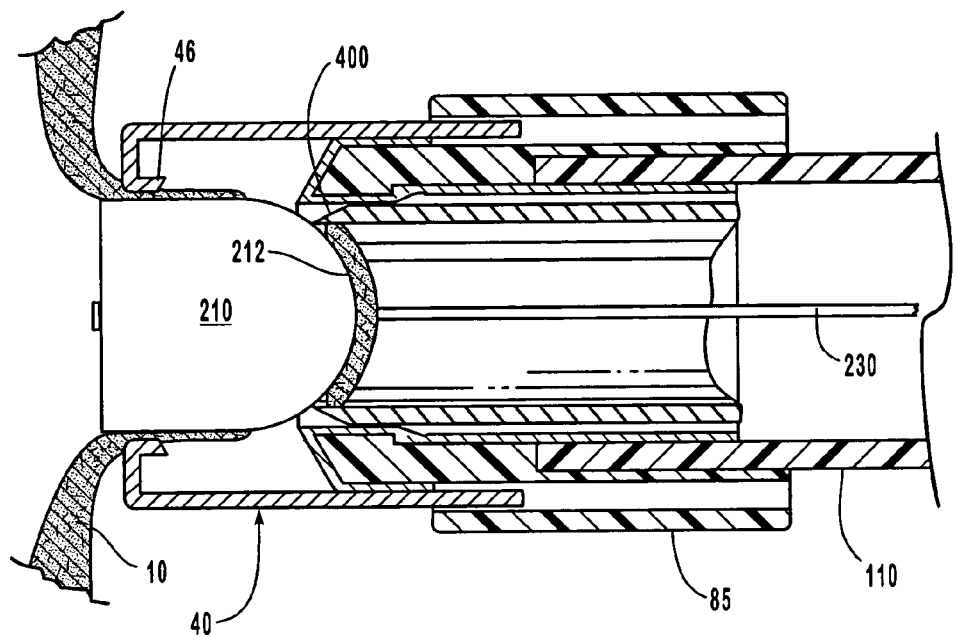

FIG. 16C is an enlarged cross-sectional view like that of FIG. 16B after the cutter has cut the target vessel wall, showing the target vessel tissue in a position to be everted over the holding tabs.

Figure 16D:
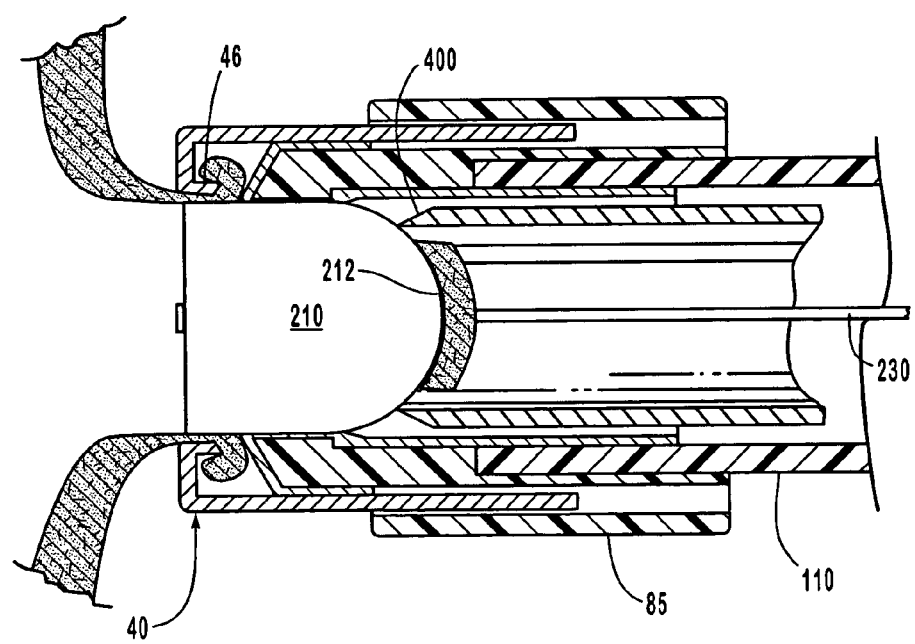

FIG. 16D is an enlarged cross-sectional view like that of FIG. 16C after the target vessel anastomosis ring has been drawn towards the access tube anastomosis ring to complete the anastomosis procedure.

Figure 16E:
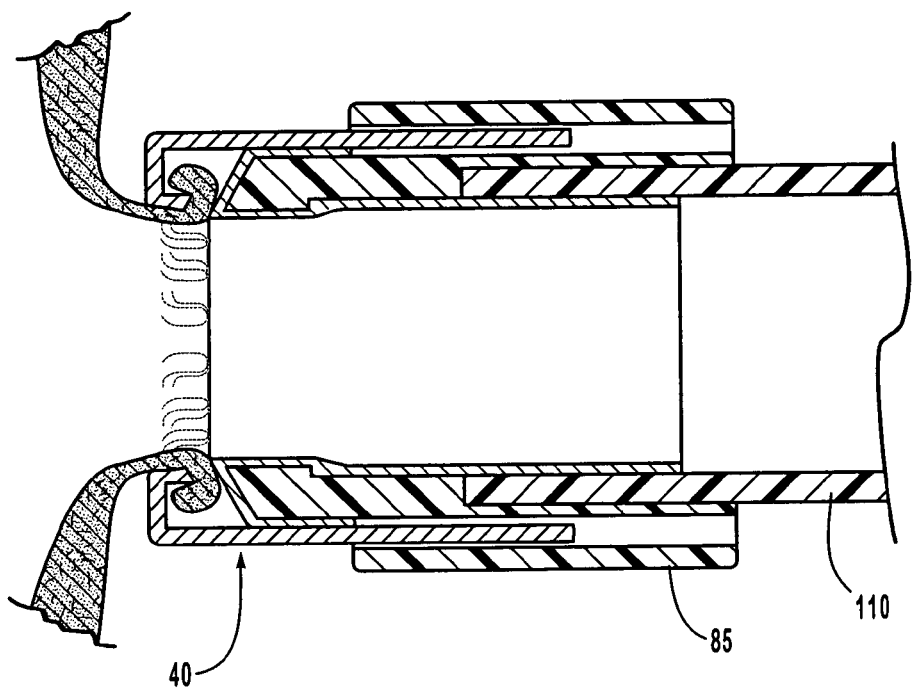

FIG. 16E is an enlarged cross-sectional view like that of FIG. 16D after the cutter and anvil apparatus have been withdrawn through the access tube conduit and the anastomosis procedure has been completed.

Figure 16F:
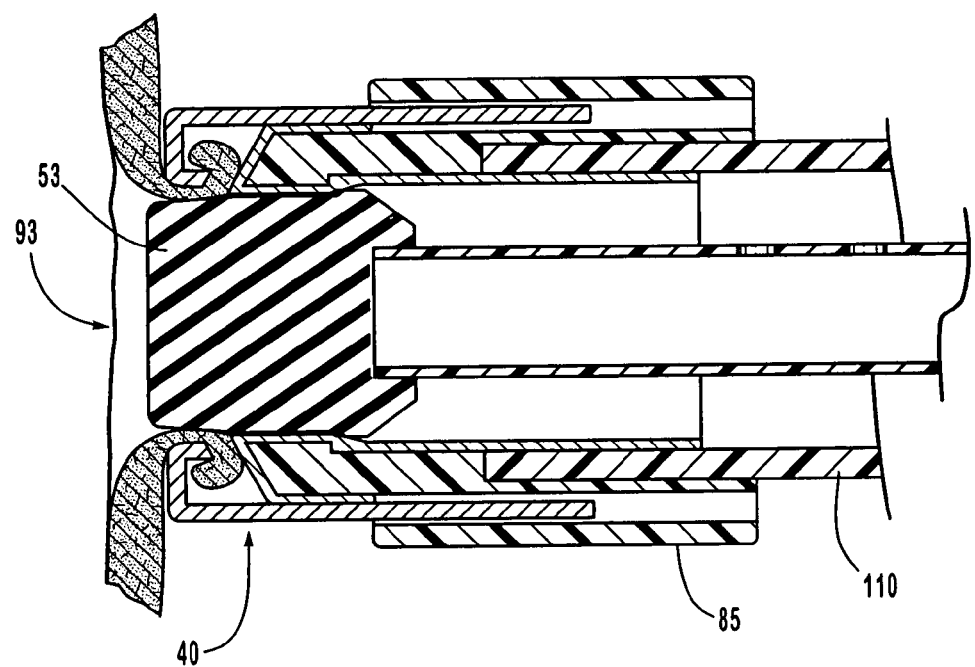

FIG. 16F is an enlarged cross-sectional view like that of FIG. 16E after the occluder has been fully positioned inside the access tube.

Figure 17:
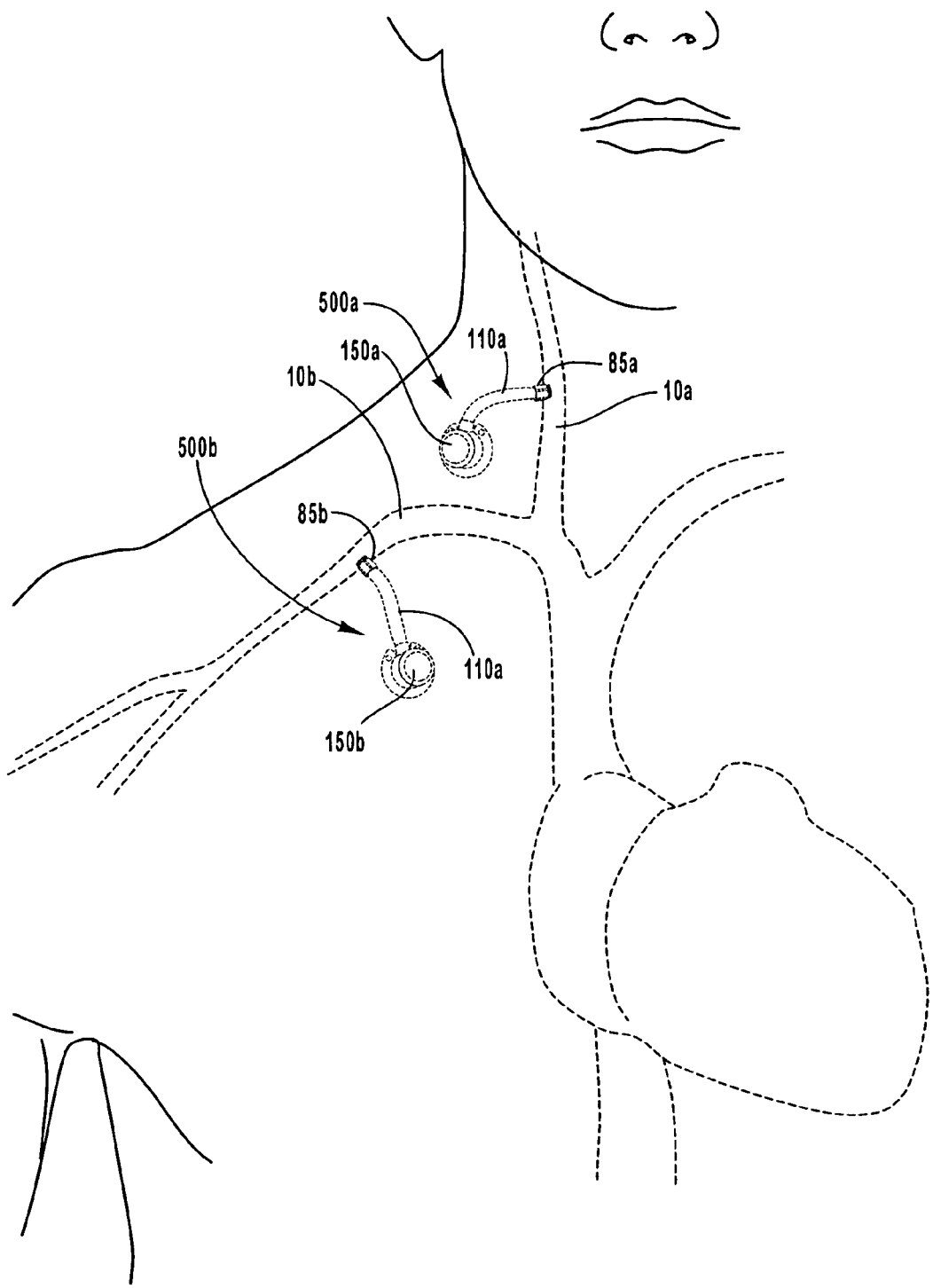

FIG. 17 is a perspective view of a subcutaneous fluid-occluder embodiment of two access tube devices attached to a patient's blood vessels.

Figure 18A:
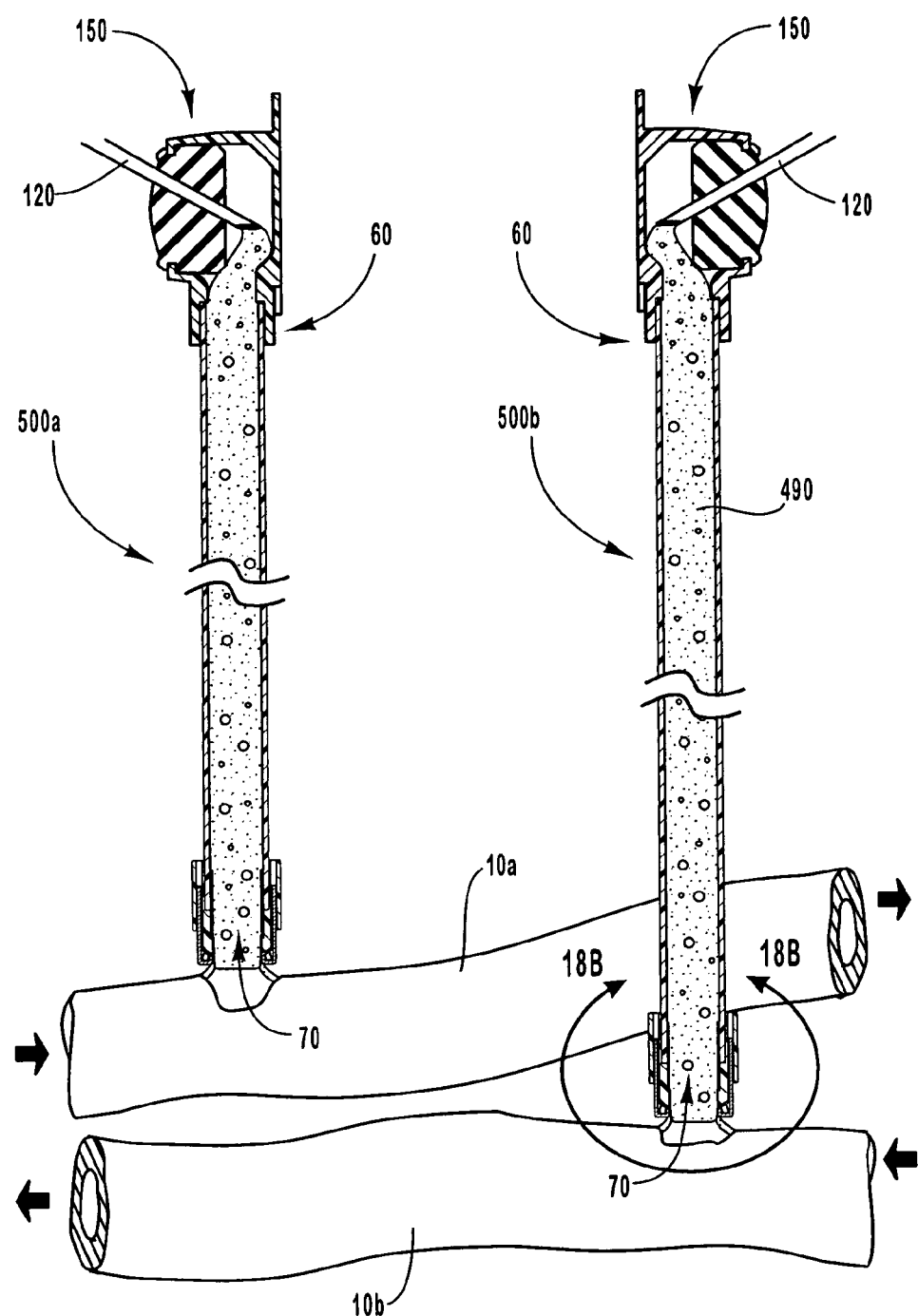

FIG. 18A is a partial cross-sectional view of the access tube devices shown in FIG. 17. The access tube devices are shown with needles penetrating their respective ports to insert the fluid occluder.

Figure 18B:
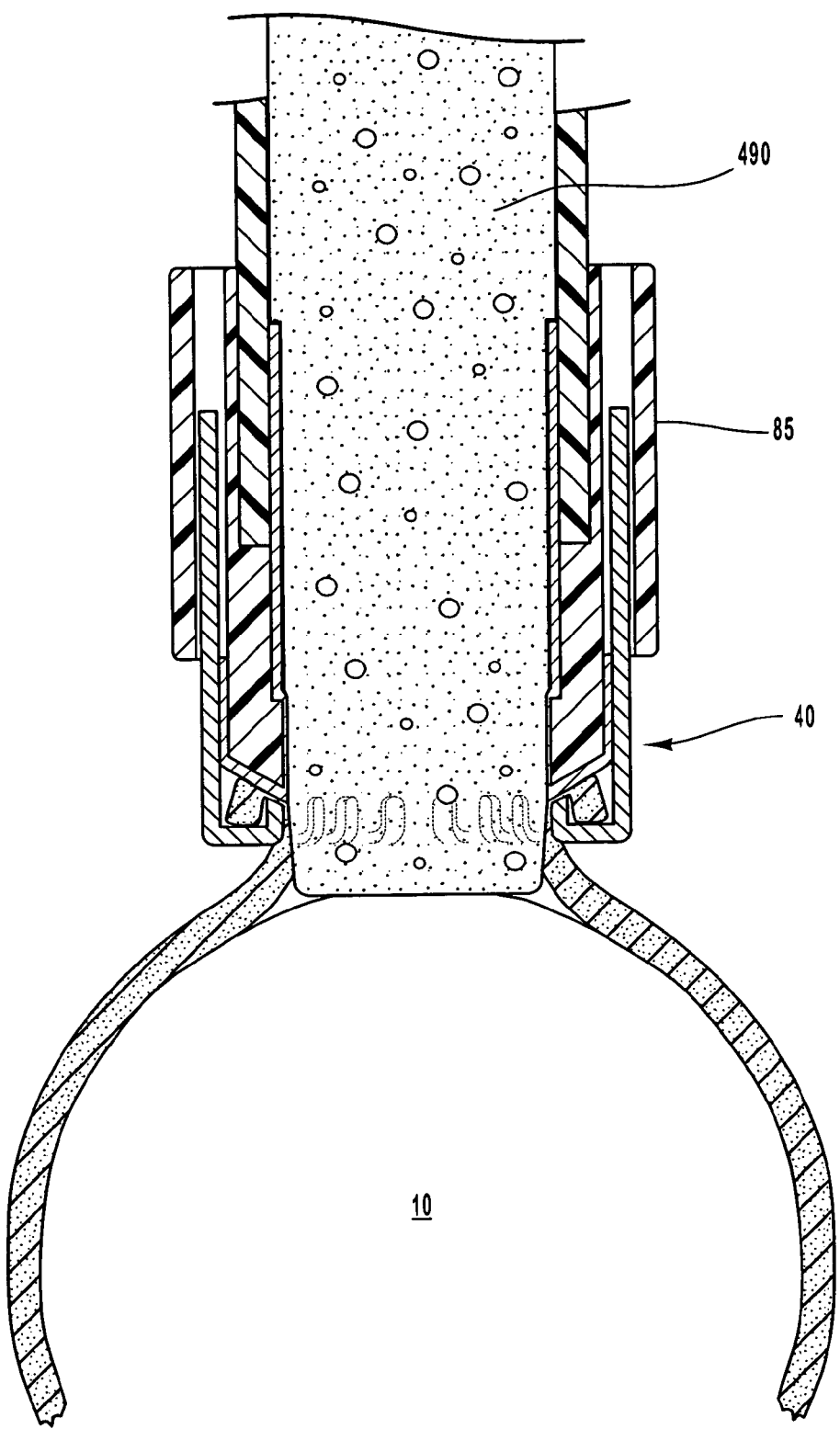

FIG. 18B is an enlarged cross-sectional view of the interface between the occlusion end of an occluded access tube device as shown in FIG. 18A and the target vessel wall.

Figure 18C:
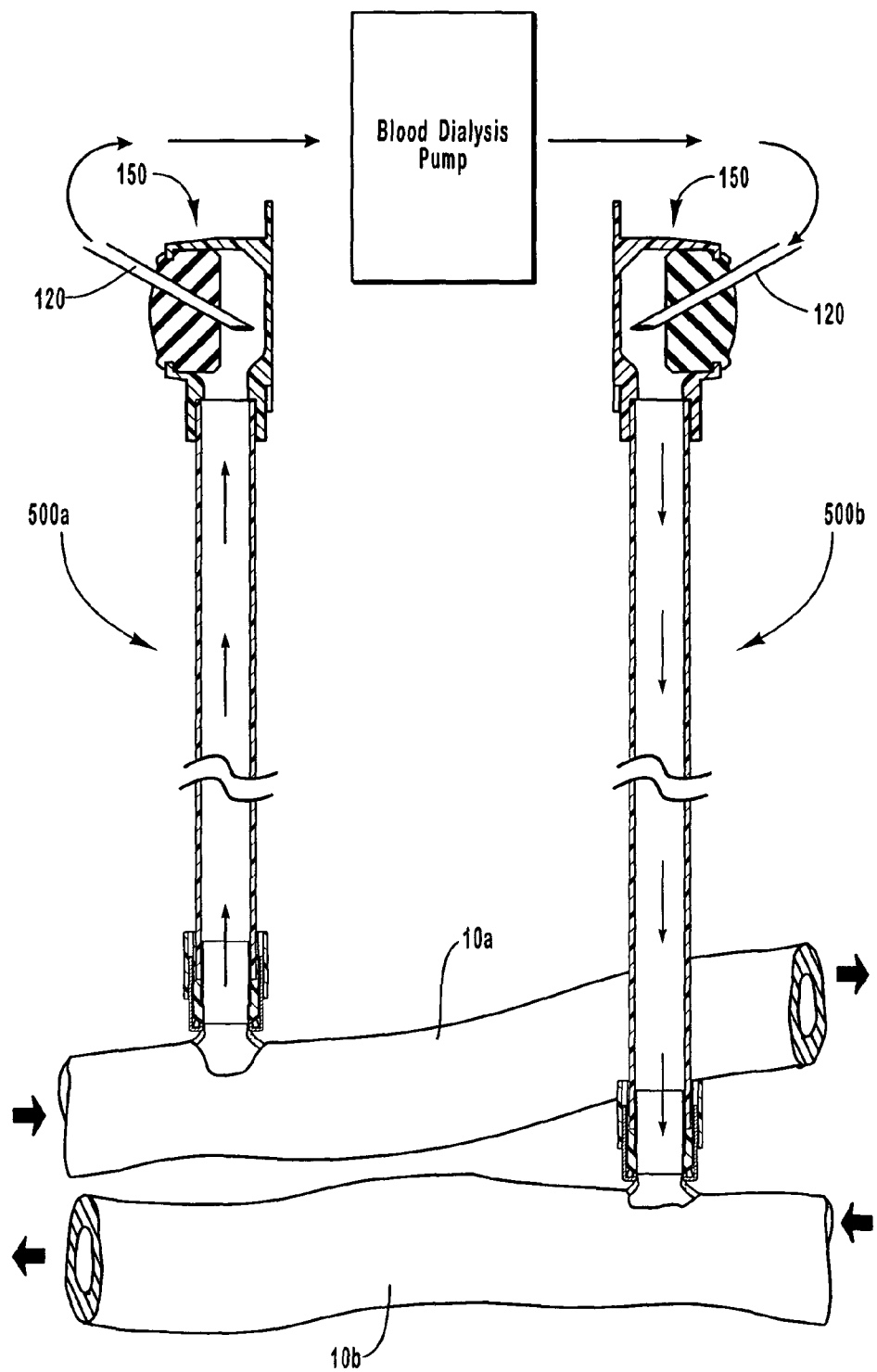

FIG. 18C is a partial cross-sectional view of the access tube devices shown in FIG. 18B after the fluid occluder has been removed to allow for access to the body fluid.

Figure 19A:
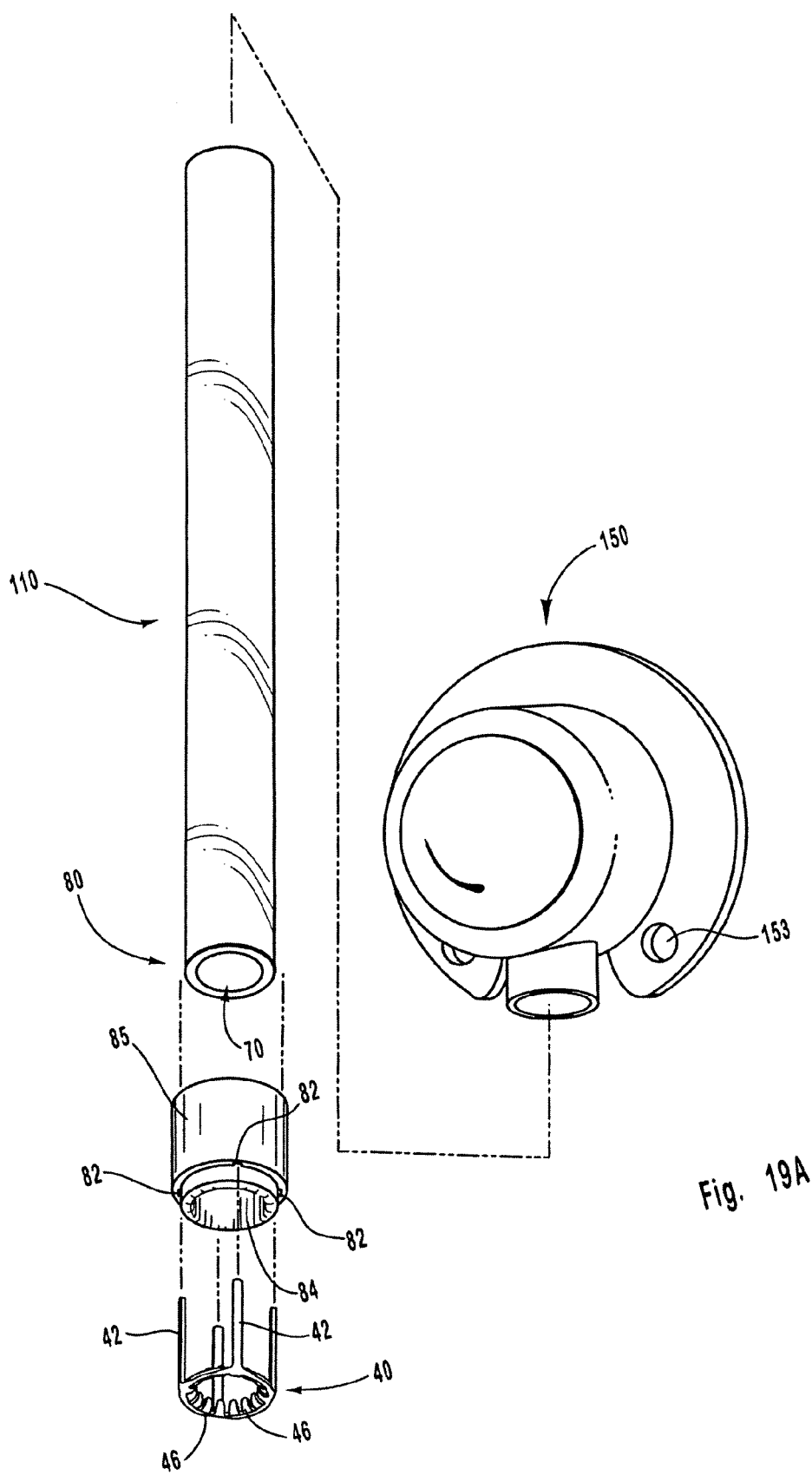
Figure 11B:
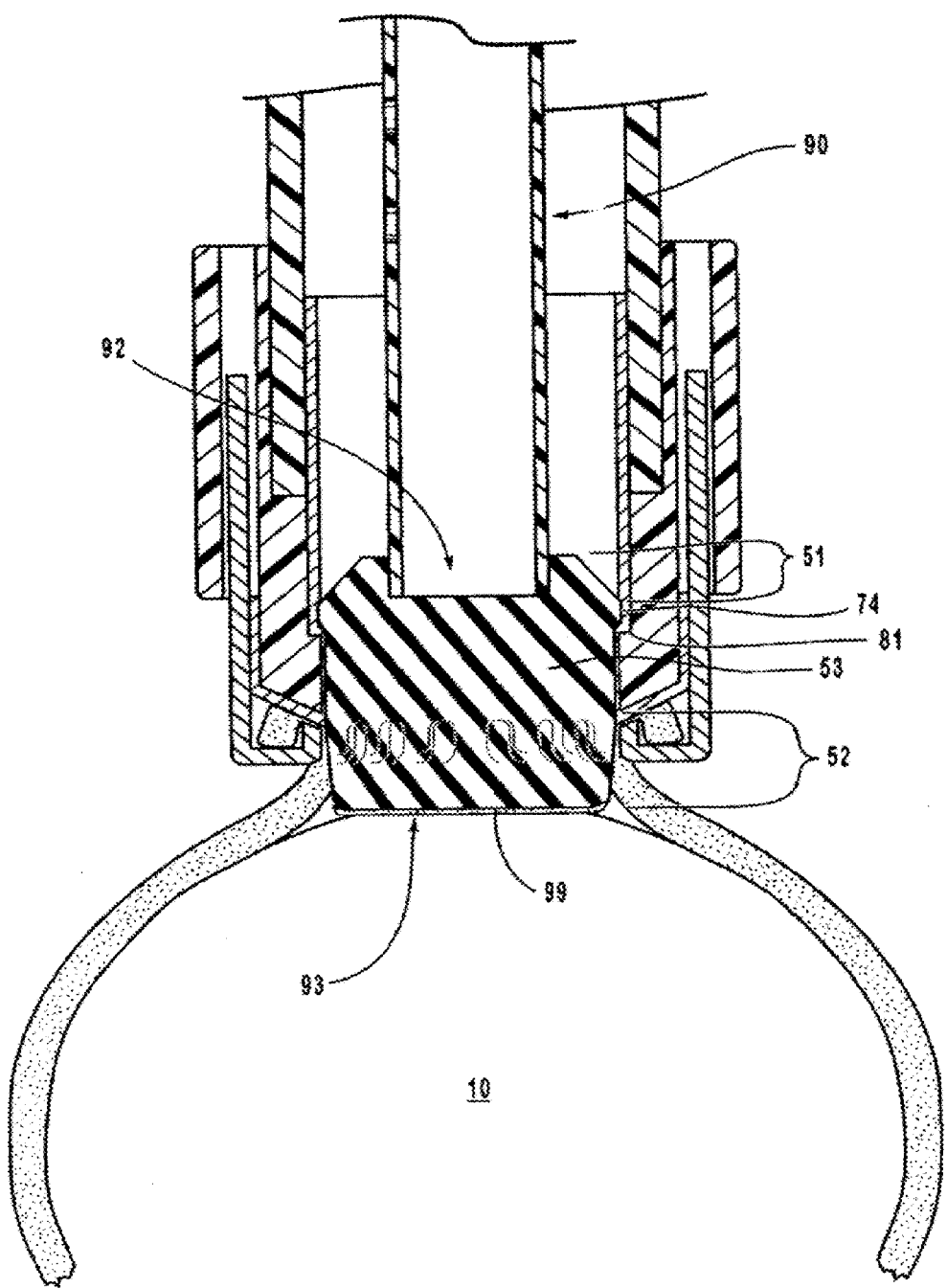
Figure 16C:
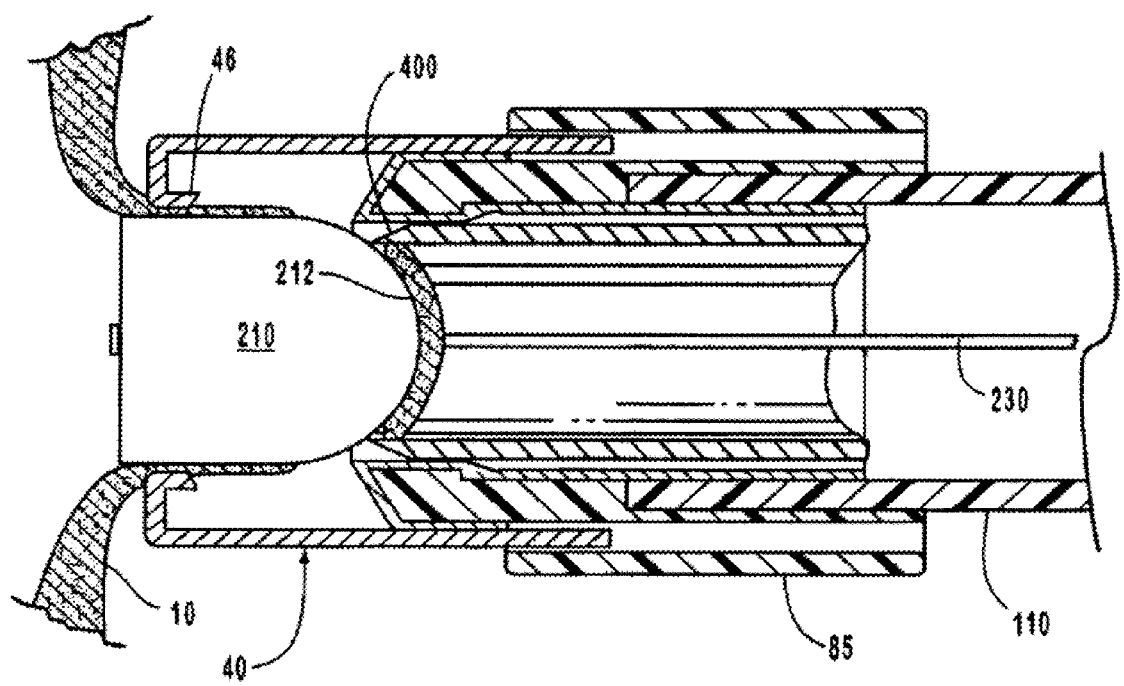
Figure 16D:
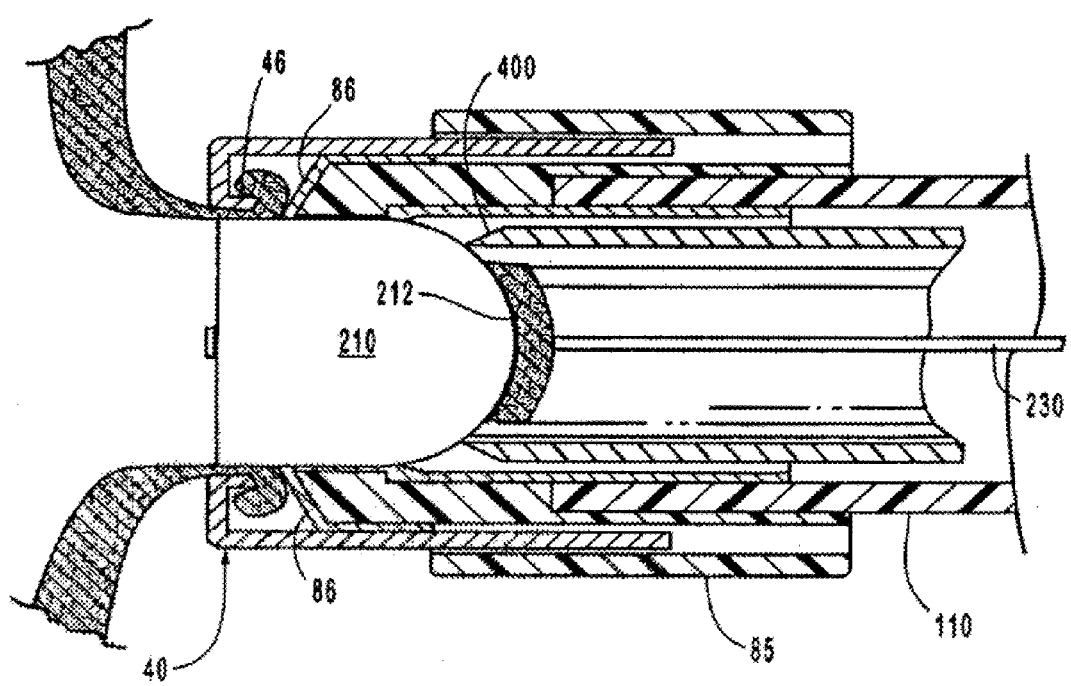

FIG. 19A is an exploded perspective view of a fluid occluder embodiment with the access port removed and the target vessel anastomosis ring withdrawn from the slots in the access tube anastomosis ring.

FIG. 19B is a perspective view of a fluid occluder embodiment with an access port attached thereto.

FIG. 19C is a cross-sectional view of the embodiment shown in FIG. 19B.

DETAILED DESCRIPTION OF PREFERRED EMBODIMENTS

Several different embodiments of the invention are disclosed herein. One embodiment of the apparatus of the present invention is identified in FIG. 1 at 100. Variations of this embodiment are identified at 100', 100", and 100'" respectively in FIGS. 2A–2B, 4A–4B, and 5. Another embodiment is identified in FIGS. 7A–9 at 200. Still another embodiment is identified in FIGS. 10–13E at 300. Variations of this embodiment are shown in FIGS. 14 and 15 at 300' and 300", respectively. Yet another embodiment is identified at 500 in FIGS. 17–19C.

The primary components of the device include an access tube and an occluder. An access tube is provided, identified generally at 110, which is adapted for anastomosis to an anatomical vessel at an anastomosis end. Embodiments of the invention can be used in connection with any anatomical vessel. To illustrate, the devices, methods, and systems disclosed herein may be used in connection with ureters, urethras, intestines, or any other vessel in the body. Thus, these embodiments of the present invention can also provide access to body fluids other than blood. In fact, any body fluid within any anatomical vessel can be accessed by the herein disclosed apparatus, methods, and systems.

The access tube may comprise any suitable device or structure, such as a catheter, graft vessel, or other such tube or generally tubular structure. Some embodiments of the access tube are closed at a terminal end opposite from the anastomosis end. Embodiments of the access tube with a terminal or closed end may be integrally sealed at that end. Alternatively, they may have an attached or otherwise affixed component at the end opposite from the anastomosis end to close or seal that end. Embodiments of the access tube with a closed end opposite from the anastomosis end are depicted in FIGS. 1–2B, 4A–9, and 17–19C. As seen in the referenced figures, an access tube may be considered "closed" at the end opposite from its anastomosis end even if access to the tube may be obtained via an access port or other port device located at that end. Other access tube embodiments have ends opposite from their anastomosis ends which are openable and reclosable. Such embodiments have a removable cap or other component that attaches, locks, screws, mates, or otherwise links with the end opposite from the anastomosis end. The anastomosis procedure may be facilitated by the use of one or more anastomosis components, several of which are identified herein.

Fitting within the access tube is an occluder. The occluder is adapted to allow for selective occlusion of the conduit of the access tube and thereby allow for selective access to the body fluid in the anatomical vessel. Anything serving these purposes is considered to be an occluder within the scope of the term as used herein. Several examples of occluders are disclosed herein. For instance, FIGS. 1–9 show various balloon occluders; FIGS. 10–15 show various plug occluders; and FIGS. 17–19C show various fluid occluders.

Some of the embodiments disclosed herein also utilize port devices and/or access ports. Such devices can be used to add, remove, inflate, or deflate the occluder. They can also be used to access the body fluid in the vessel once the occluder has been disengaged.

It is with reference to the accompanying figures, beginning with FIG. 1, that several embodiments of the present invention will now be discussed in greater detail. The embodiments disclosed in the first several figures employ balloon occluders. Several different embodiments of the balloon occluder are disclosed herein. These embodiments are respectively shown at 240 in FIG. 1, at 240' in FIGS. 2A–2B, at 240" in FIGS. 4A–4B, at 240'" in FIG. 5, and at 340 in FIGS. 7A–7C. The balloon occluder may be an impermeable balloon or it may have a permeable or semipermeable region at its delivery end, which is referenced at 242 in the embodiment in FIG. 1. The benefits of a permeable or semipermeable region are discussed in detail below. The embodiment of balloon occluder 240' in FIGS. 2A–2B has a membrane 243' at its delivery end 242' that is semipermeable.

Figure 4A:
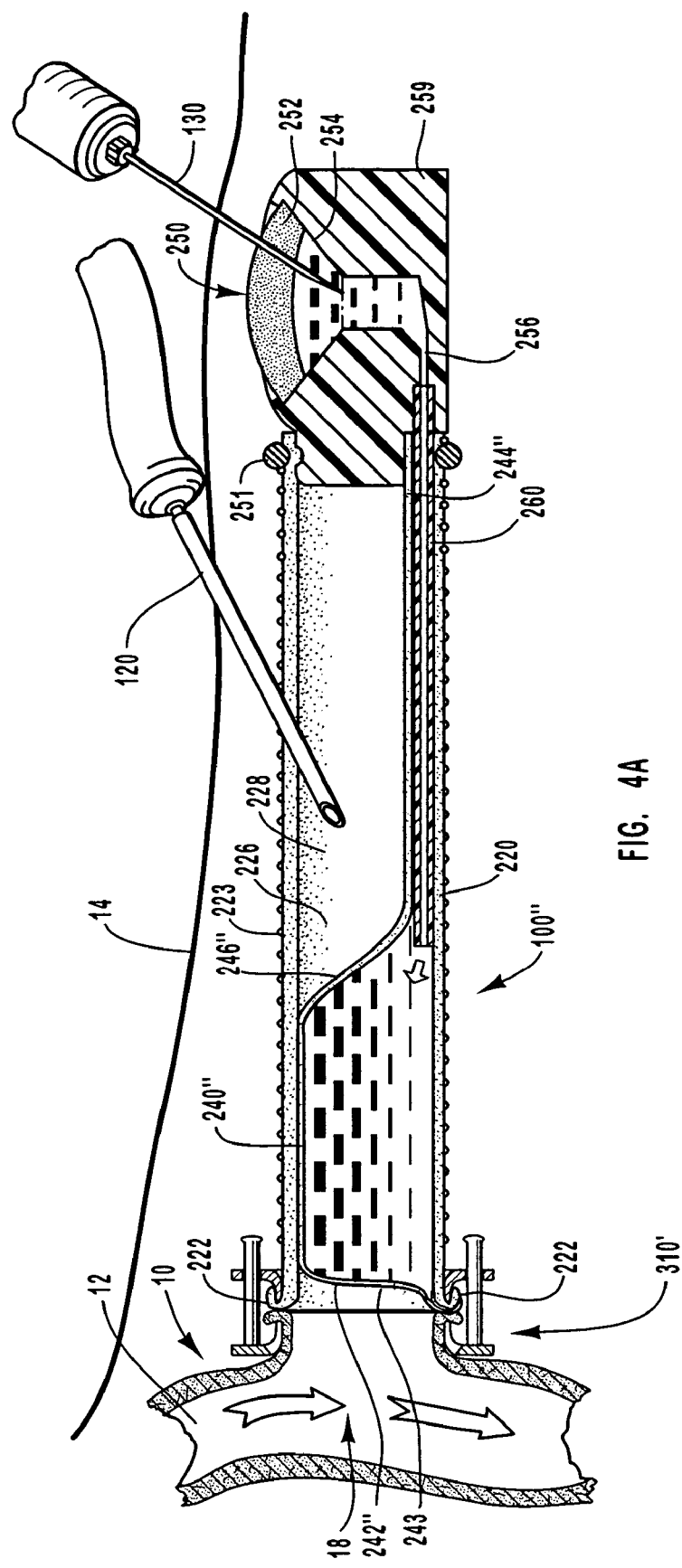
FIG. 4A is a partial cross-sectional view of an embodiment of a vascular access system with a balloon occluder that extends integrally from the access tube. The access tube of the system is attached to the blood vessel by a compression plate assembly and the balloon has been filled.
Figure 4B:
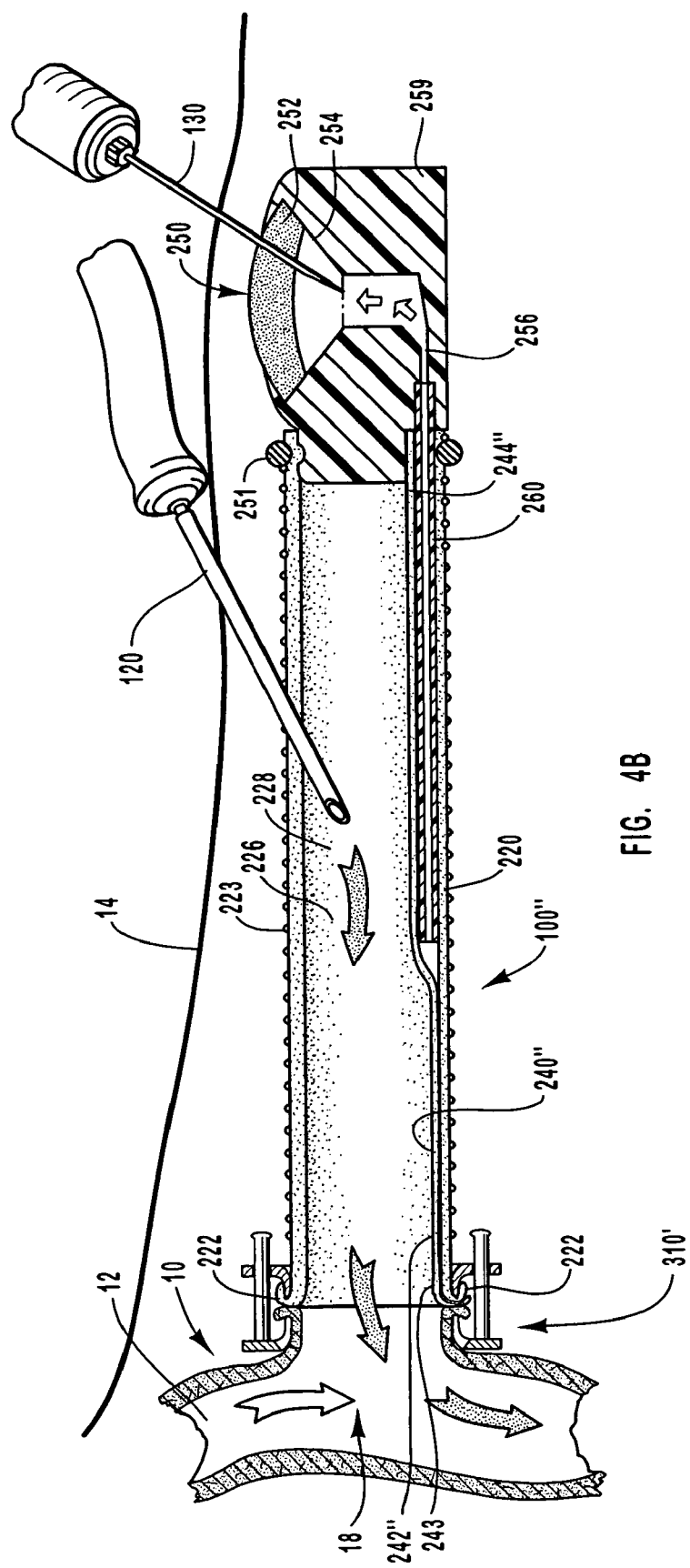
FIG. 4B is a partial cross-sectional view of the embodiment shown in FIG. 4A with the balloon deflated to allow for vascular access.

Balloon 240" shown in FIGS. 4A–4B is integral with the access tube, which is depicted in the accompanying figures as a graft vessel. Finally, the balloon embodiment shown in FIGS. 7A–7C has a toroidal shape. Each of these embodiments is discussed in detail below.

A common feature of the balloon occluders is that they are adapted for distension and contraction within an access tube at an anastomosis site after the access tube has been anastomosed to an anatomical vessel. When expanded in a distended position the balloon blocks fluid communication between the access tube and the vessel, as shown in FIGS. 1, 2A, 4A, 5, and 7A. When deflated to a contracted position, the balloon permits fluid communication between the access tube and the vessel, as shown in FIGS. 2B, 4B, 7B, and 7C. The benefit of this arrangement is that the access tube can be repeatedly accessed for treatment of the body fluid or for any other purpose necessitating access to an anatomical vessel. This provides a significant improvement over conventional techniques that require repeated puncturing of a blood vessel.

Figure 1:
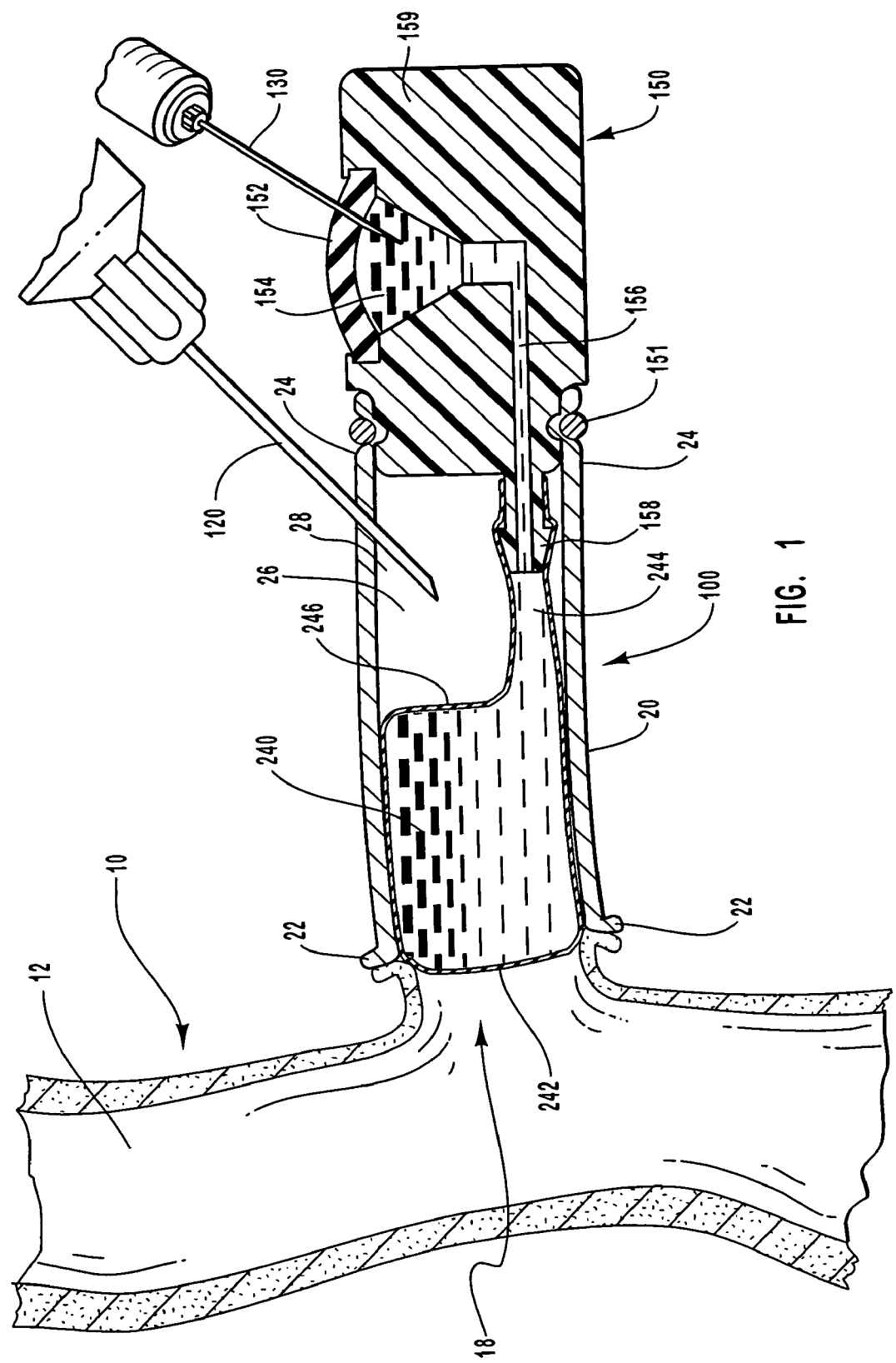

FIG. 1 schematically and generally shows in a cross-sectional view relevant features of this invention as illustrated by an exemplary embodiment. In this depicted embodiment, the anatomical vessel being accessed is blood vessel 10. Blood vessel 10 in this exemplary embodiment is accessed with the aid of an access tube—shown in the figure as a graft vessel 20—that is anastomosed to the blood vessel 10 at an anastomosis site 18 by any suitable methodology. Graft vessel 20 houses, in this particular embodiment, balloon occluder 240 with a delivery end 242 and an access conduit or end 244.

Graft vessel 20 is shown in FIG. 1 after its anastomosis end 22 has been anastomosed to blood vessel 10 at anastomosis site 18. As illustrated by the embodiment shown in FIG. 1, delivery end 242 of balloon 240 generally corresponds with anastomosis end 22 of graft vessel 20 in the sense that both ends are generally located in the region of the anastomosis site 18.

In this embodiment, once graft vessel 20 has been anastomosed to blood vessel 10, then graft vessel 20 remains subcutaneously located along with a port device 150 which is attached to port end 24 of graft vessel 20 opposite from anastomosis end 22. This arrangement enables a hypodermic needle 120 or a similar medical device to be inserted from outside of the patient's body, and to then inject fluids into or draw them from lumen 26 of graft vessel 20 once balloon 240 has been deflated. This arrangement also enables a hypodermic needle 120 to flush lumen 26 by repeatedly injecting and withdrawing fluids, such as a saline solution, from the lumen 26 of graft vessel after balloon 240 has been sufficiently inflated to occlude graft vessel 20. Note that graft vessel 20 is made of a biocompatible material such as polytetrafluoroethylene (PTFE). The biocompatible material may also be adapted to allow for repeated punctures and may also be self sealing.

Port device 150 provides access to balloon 240 and enables a hypodermic needle 130 to inject fluids into balloon 240 and to draw fluids from balloon 240. Port device 150 has a self-sealing cover 152 that is adapted to receive a hypodermic needle 130 or any other medical instrument that is typically used to inject fluid into or to draw fluid from a cavity. Embodiments of the self-sealing cover according to this invention are preferably made of silicone rubber. Port device 150 preferably has a chamber 154 that is in fluid communication with a conduit 156. Chamber 154 is preferably funnel shaped as shown in order to guide the needle 130. Conduit 156 is preferably oriented perpendicularly relative to funnel shaped chamber 154. Conduit 156 extends through a coupler 158 and is in fluid communication with balloon 240. Balloon 240 is coupled to port device 150 by inserting coupler 158 into access end 244 of balloon 240. Coupler 158 may be flared as shown and access end 244 is sized to ensure a secure frictional engagement. Port device 150 is preferably located in housing 159.

As shown in the example depicted in FIG. 1, port end 24 of graft vessel 20 is detachably connected to port device 150 by a pressure device 151 that exerts sufficient pressure to maintain the leak-proof attachment of graft vessel 20 to port device 150. Pressure device 151 can in particular be embodied by an O-ring or by any other device that exerts sufficient pressure to maintain the leak-proof attachment of graft vessel 20 to port device 150. This leak-proof attachment can be accomplished in other embodiments of this invention by a threaded engagement, a snap joint engagement, a bound engagement, an adhesive bound engagement, combinations of these features, or by any type of leak-proof engagement that is well-known in the art. Graft vessel 20, or any other access tube disclosed herein, may be an integral extension of housing 159. Embodiments of the port device are preferably made of stainless steel or titanium, although other biocompatible materials can also be used, particularly other biocompatible materials that are preferably resistant to the abrasion of sharp needle tips.

Port devices such as port device 150 are common medical devices. Commercially available port devices for vascular access include devices that are marketed by Horizon Medical Products of Atlanta, Ga., under the trademarks Omega-Port7, TitanPort7, and Vortex7; by SIMS Deltec, Inc. of Saint Paul, Minn. under the trademarks P.A.S. Port7 and P.A.S. Port7 II; and also by Smiths Industries Medical Systems. Port devices according to this invention can also be embodied by port devices that have additional ports for conventional uses, such as ports that are configured to operate probes, sampling devices, imaging devices and imaging device elements, or medical intervention assisting devices.

As indicated above, occlusal balloon 240 can be inflated with a fluid provided thereto through port device 150, in which case occlusal balloon 240 prevents the flow of blood into graft vessel 20 by occluding and effectively sealing anastomosis site 18. As also indicated above, occlusal balloon 240 can be selectively deflated by drawing its fluid content through port device 150, in which case blood flow from blood vessel 10 invades the interior of graft vessel 20 through anastomosis site 18. Embodiments of inflatable balloons according to the present invention, are made of any elastic biocompatible material, such as rubber, PTFE particularly expanded PTFE (ePTFE), latex, polyurethane, polyethylene teraphthalate (PET), silicone and combinations of these materials. When the embodiment of the inflatable balloon comprises a membrane that is attached to the balloon with an adhesive, gluable balloon material may be used, such as silicone rubber.

When blood flow from blood vessel 10 reaches the interior of graft vessel 20 because occlusal balloon 240 is in a deflated configuration, graft vessel 20 can be punctured by a needle to perform a procedure, for example a hemodialysis, or to deliver a medication. When the dialysis session is finished, occlusal balloon 240 can be inflated again by injecting an appropriate fluid through port device 150 via needle 130 and any remaining blood left in lumen 26 can be drawn out of this space and replaced with a fluid such as saline solution or any other appropriate biocompatible fluid.

Note that balloon 240 is shaped when distended in its inflated configuration such that it does not entirely fill lumen 26. More particularly, balloon 240 may have a chamber portion 246 that defines a chamber 28 within lumen 26 along with access conduit or end 244, port device 150 and graft vessel 20. As shown in FIG. 1, needle 120 may be inserted into chamber 28 for repeated flushing of chamber 28 after balloon 240 has been reinflated upon the completion of a procedure. Embodiments of this invention that are provided with a balloon occluder may be configured in a way such that the access end of the balloon and the port device are separated by a chamber 28 within lumen 26 that is several centimeters long. In some embodiments, however, the inflated balloon can extend up to and be in contact with the port device.

In its inflated configuration as shown in FIG. 1, occlusal balloon 240 is filled with a fluid that causes, or in some embodiments contributorily causes, the expansion within elastic compliance limits of such a balloon to effectively seal the graft vessel at the anastomosis site. The balloon can be repeatedly inflated and deflated within its elastic compliance limits.

Balloon 240 may be an impermeable occlusal balloon that is injected with a fluid that directly causes the inflation of the balloon. Since the fluid cannot diffuse out of the balloon, the balloon is inflated or deflated by removal of the fluid through port device 150. The fluid may be any suitable liquid or gas.

Blood flow stagnation in the region near anastomosis site 18 should be minimized. To this end, occlusal balloon 240 may be so configured as to be able to seal the anastomosis site in a way such that no significant cavity is formed at anastomosis site 18.

Figure 2A:
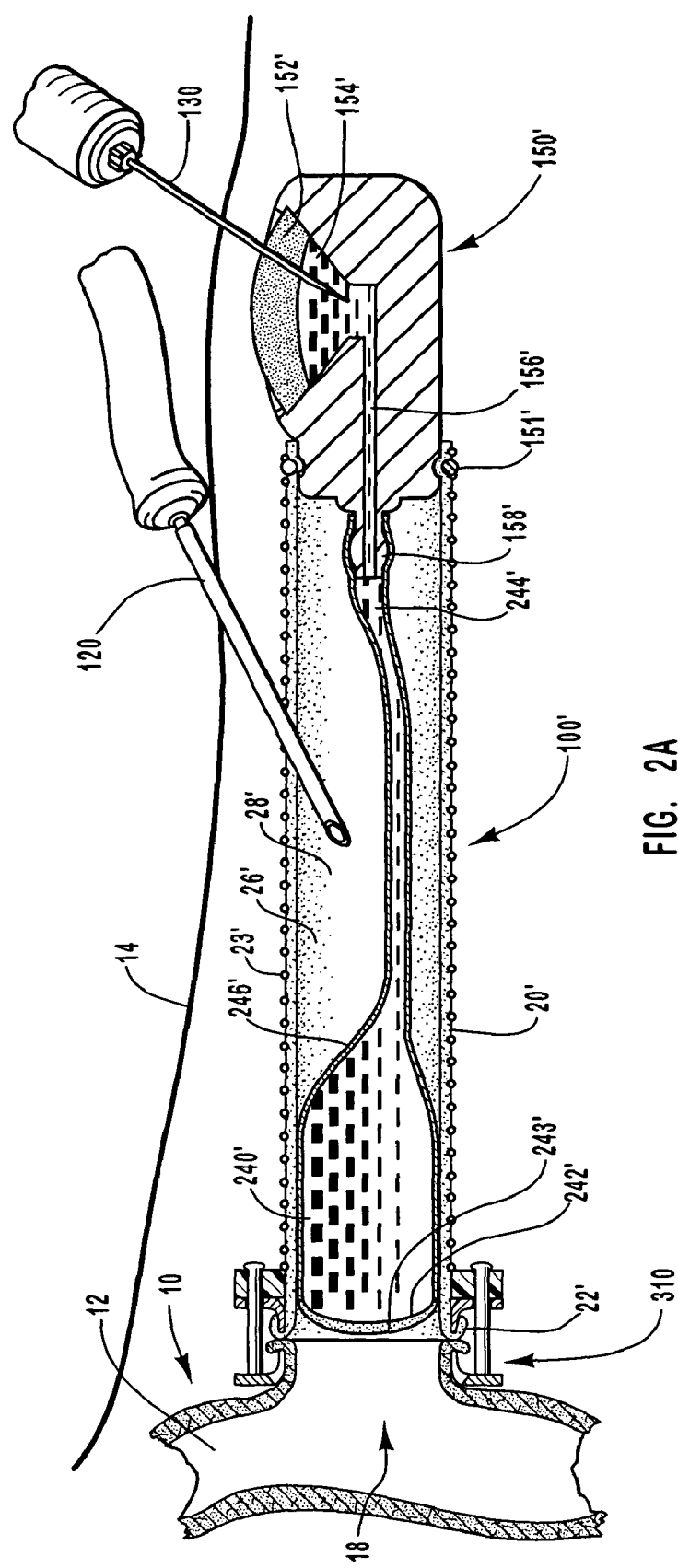
Figure 2B:
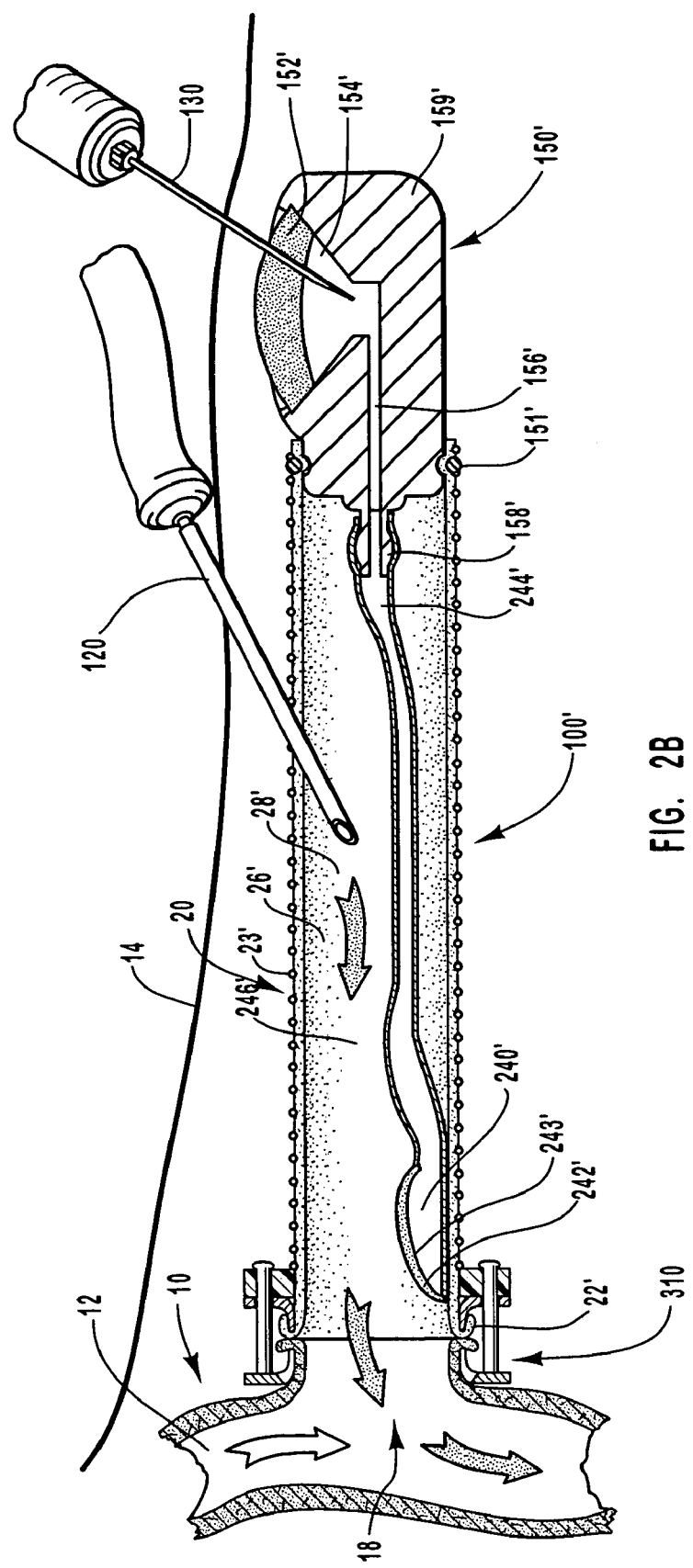

While balloon 240 may be impermeable so that the fluid used to inflate and deflate the balloon remains in the balloon, balloon 240 may also have a permeable or semipermeable region at its delivery end 242. A balloon having such a semipermeable or permeable region at its delivery end allows for fluid transport out of and into the interior of the balloon. As shown in FIGS. 2A–2B, a balloon 240' may also have a delivery end 242' with a membrane 243' that is permeable or semipermeable. Such regions and membranes are examples of semipermeable portions of a balloon that enable the balloon to deliver an anticoagulant locally to the anastomosis site 18. Additionally, a balloon having a semipermeable region may be initially inflated by a liquid injected into the balloon. However, other phenomena, such as osmosis, cause such a balloon to remain in an inflated configuration, as described below.

A balloon having a semipermeable membrane 243' and a balloon having an integral semipermeable region such as balloon 240 may both be utilized to deliver an anticoagulant agent or another physiologically active agent. More particularly, such semipermeable balloons may be designed with an integral semipermeable region or a semipermeable membrane that has a selective porosity. After a liquid is delivered into the interior of the balloon that contains a physiologically active agent—particularly anticoagulants such as heparin at the appropriate dosage—then the porosity of the semipermeable region or membrane permits the anticoagulant to pass out of the balloon and be transported into luminal space 12 of blood vessel 10 at the anastomosis site 18. These features and elements of a vascular access device according to this invention function to provide a selective and controlled exposure, and more specifically, to provide a selective and controlled transport.

The porosity may also be selected to permit aqueous fluid from the bloodstream in blood vessel 10 to migrate through the semipermeable region or semipermeable membrane of the balloon and into the balloon to keep the balloon in a distended configuration by osmosis. So, by properly designing the semipermeable region or membrane, osmotic pressure may be utilized to permit the flow of aqueous fluid from the blood flow in blood vessel 10 into the interior space of occlusal balloon 240. Osmosis can be accomplished by delivering into the interior of occlusal balloon 240 a fluid that contains a preferably biocompatible substance that cannot permeate across the membrane through which heparin or another physiologically active agent is delivered. An example of such substance is albumin. The fluid within balloon 240 thus contributes to providing the adequate conditions for osmosis to take place and hence to the maintenance of balloon 240 in an inflated configuration as heparin, or some other substance, diffuses from the interior of occlusal balloon 240 into the blood flow in blood vessel 10.

In addition to, or instead of, heparin or another anticoagulant, an occlusal balloon having a permeable or semipermeable delivery end such as 240 and 240' can be used to deliver a medication, and in particular a medication for a long-term treatment of a chronic disease. This medication can also be delivered by letting it diffuse across a permeable region at delivery end 242 of occlusal balloon 240 or through a permeable membrane 243' of occlusal balloon 240'. In the exemplary embodiment shown in FIG. 1, heparin and any other substance that diffuses through a semipermeable membrane at delivery end 242 can be periodically supplied to the interior space of occlusal balloon 240 by injection through port device 150. Similarly, port device 150' can be utilized to resupply balloon 240'.

In the practice of hemodialysis and also in the prolonged delivery of medicine for the treatment of a chronic disease, it is very useful to fill the occlusal balloon an aqueous solution that includes a high molecular weight substance such as albumin that cannot diffuse through the pores of the chosen semipermeable region or membrane and at least one physiologically active agent of a smaller molecular weight such as heparin that can diffuse through the pores of the chosen semipermeable region or membrane. In some of the embodiments of this invention, heparin is the physiologically active agent and also the solute whose concentration gradient gives rise to the osmotic pressure that keeps the occlusal balloon inflated. The occlusal balloon holds in these embodiments a relatively large volume of solution so that the concentration of heparin does not decrease too rapidly as a consequence of its diffusion rate across the properly chosen semipermeable region or membrane.

The aqueous solution of albumin and heparin provides the concentration gradient driving the osmotic process which in turn keeps the occlusal balloon in an inflated configuration. Osmosis in this context involves the diffusion of aqueous fluid from the blood in the blood vessel being accessed into the interior of the occlusal balloon through the pores of an appropriately selected semipermeable region or membrane that is in contact with the blood flow at the anastomosis site. Albumin used in this invention is preferably human albumin with a molecular weight of approximately 65000.

Heparin diffuses through the pores of such semipermeable membrane into the blood in the blood vessel which is being accessed, thus preventing the coagulation of blood that might otherwise take place as a consequence of a variety of factors that are associated with the features of the anastomosed structures. The molecular weight of the heparin preferably used in embodiments of the present invention ranges from about 500 to about 18000. Heparin inhibits reactions that lead to the clotting of blood and the formation of fibrin clots both in vitro and in vivo. The clinical pharmacology of heparin is that of a substance that acts at multiple sites in the normal coagulation system. In particular, small amounts of heparin in combination with antithrombin III (heparin cofactor) can inhibit thrombosis by inactivating activated Factor X and inhibiting the conversion of prothrombin to thrombin. Once active thrombosis has developed, larger amounts of heparin can inhibit further coagulation by inactivating thrombin and preventing the conversion of fibrinogen to fibrin. It is reported that heparin also prevents the formation of a stable fibrin clot by inhibiting the activation of the fibrin stabilizing factor.

In choosing the appropriate concentrations of albumin and heparin, however, a variety of determining factors have to be taken into consideration. Heparin and albumin associate to some extent. This association leads to the effective sequestering of heparin that is not available to diffuse into the blood stream. In addition, some of the albumin can be adsorbed on the semipermeable region or membrane, thus decreasing the effective concentration of albumin that influences osmosis.

The concentration of albumin is accordingly determined so that the osmotic pressure is comparable to and slightly greater than the vascular pressure in the blood vessel being accessed. For example, venous pressure is typically in the approximate range of about 5 mmHg to about 15 mmHg, and rarely exceeds 30 mmHg, in which case a venous vascular access according to this invention should preferably provide an albumin solution in the occlusal balloon at an osmotic pressure slightly greater than 30 mmHg, such as in the approximate range of about 35 mmHg to about 45 mmHg.

"Nominal molecular weight pore size portion" including an integral region or an attached membrane in this context characterizes a semipermeable region or membrane whose pore size is such that particles whose molecular weight is less than the given nominal molecular weight are able to diffuse through the pores of the semipermeable region or membrane, whereas substances whose molecular weight is greater than or about equal to the given nominal molecular weight cannot diffuse through the pores. Unless otherwise indicated, molecular weights given herein are expressed in Daltons; albumin concentration units given herein are expressed as a percentage that refers to mass in grams of albumin in 100 ml of solution, and heparin concentration units are expressed as International Units (IU) heparin per ml of solution.

Any material having a molecular weight that is greater than or about equal to the given nominal molecular weight of materials that can diffuse through the pores can be utilized as a nontransportable material or as an osmotic agent. In addition to albumin, another example of such a nontransportable material that has a can be utilized to fill the occlusal balloon is a gel. Such a gel may be a water-soluble gel. The gel may also be salt free or at least substantially free of salts. An example of a suitable water soluble gel that is substantially free of salts is the gel sold as AQUASONIC 7 100 gel by Parker Laboratories, Inc. Another suitable commercially available gel is SURGILUBE7 100 gel sold by E. Fougera & Co. Other examples of water soluble gel materials that can be utilized with water to form a water soluble gel include carboxypolymethylene, polyacrylic copolymers, gums, polyethylene oxides, proteins, and mixtures thereof. As indicated above, the water soluble gel is preferably salt free in order to provide an appropriate osmotic gradient.

An advantage of gels such as the gel sold as AQUASONIC 7 100 gel is that the molecules are larger than albumin which enables their use with balloons having a different range of porosity. More particularly, the pores or passageways in some types of PTFE are too large to retain albumin so gels may be more appropriately utilized with some balloon materials. Balloons formed from PET may have pores or passages that are small enough that albumin can be used.

The ratio of heparin to osmotic agent depends on the type of osmotic agent such as gel or albumin. For example, the ratio of heparin to the osmotic agent may range from about 1:1 to about 10:1. A ratio of about 4:1 for the volume of heparin to the volume of a gel is useful for a water-soluble gel, such as the gel sold as AQUASONIC 7 100 gel. Note that the preferred ratio depends on the porosity of the permeable region or membrane of the balloon. Note also that decreasing the heparin concentration decreases the antithrombogenic effect while increasing the heparin concentration increases the osmotic gradient.

Membranes such as membrane 243' are preferably formed from polyethersulfone and are most preferably the semipermeable material sold as Biomax7 membranes from the Millipore Corp. or Bedford, Mass. This semipermeable membrane is available in several nominal molecular weight pore sizes in the range from about 5000 to about 50000. Preferred membranes for embodiments of this invention are characterized by a pore size in the range from about 30000 to about 50000 nominal molecular weight. Among these types of semipermeable membrane, a more preferred type is a membrane with a nominal molecular weight pore size of about 50000.

In general, preferred membranes for embodiments of this invention are ultrafiltration membrane materials. In addition to the Biomax7 membrane, Millipore provides other membranes such as regenerated cellulose membranes sold as Amicon™ 4M membranes which have a nominal molecular weight pore size of about 1000 to about 100000, and hydrophilic polysulfone membranes sold as Amicon™ Zm membranes which have a nominal molecular weight pore size of about 500 to about 500000.

Generally, semipermeable membrane base materials include polymeric materials such as polytetrafluoroethylene, polysulfone, polyamide, polyacrylonitrile, and cuprophane of the adequate pore size, although the hydrophobicity of some polymers requires the treatment of the base material prior to its use as a semipermeable membrane.

Clinical dialyzer materials that can be used in the context of this invention include a cuprophane material sold as CF 15.11 from Baxter Health Care Corp., Deerfield, Ill.; cellulose acetate material sold as COAK 4000 and saponified cellulose ester sold as SCE from Cordis Corporation of Miami, Fla.; polymethylmethacrylate Filtryzer membranes from Toray Industries of Tokyo, Japan; cuprammonium material sold as Rayon from Terumo Corporation of Tokyo, Japan; and cuprophane material sold as Hemoflow D3 and polysulfone material sold as Hemoflow 60 from Fresenius A.G., Germany.

It has been found useful to condition a polyethersulfone membrane, which may be used in certain embodiments, prior to its use by immersing it in an albumin solution. For example, by immersing it in a 10% albumin aqueous solution for about one week. Once conditioned, the membrane can be repeatedly used as long as it is not allowed to substantially dehydrate.

When the balloon has an integral semipermeable region such as balloon 240, then the balloon may be formed from a single material that is treated to be impermeable with the exception of the region at delivery end 242 that is intended to be permeable or semipermeable. For example, the balloon may be formed from expanded PTFE that is then soaked or coated with a solution that fills the pores or passageways of the PTFE. The solution may, for example, comprise polyurethane, such as TecoFlex7 polyurethane from Thermedics, Inc., soaked in tetrahydrofuran. The solution fills the pores and then the tetrahydrofuran evaporates leaving the polyurethane.

The balloon may also be integrally formed from polyethylene terephthalate (PET) with a semipermeable region at its delivery end. A source of PET that is appropriate for some embodiments is sold by Advanced Polymers of New Hampshire. The semipermeable region of the balloon formed from PET may, for example, be formed by bombarding the region that is desired to be semipermeable, with high energy particles from a linear accelerator and then contacting the region with a solvent to further enlarge the holes made by the high energy particles. Such a process is disclosed by Mark A. Saab in the article entitled "Applications of High-Pressure Balloons in the Medical Device Industry" in Medical Device and Diagnostic Industry, September 2000, at pages 86–97.

As indicated above, although embodiments of balloons serving as occluders according to this invention include a semipermeable region or membrane that allows for transport and is part of the osmosis that keeps the occlusal balloon inflated, other embodiments of the balloon do not include a semipermeable region or membrane. For example, some embodiments of the occlusal balloon are inflated by the injection of a fluid that is kept within the balloon while it is inflated, with no osmosis contributing to its distension. Note that an impermeable membrane such as balloon 240 that does not have a permeable region may be filled with any suitable material. For example, any gel material described above can be utilized as well as albumin. Additional suitable materials are described below in regard to fluid occluder embodiments. These embodiments of impermeable occlusal balloons may be configured so that the exposure to a physiologically active agent of the blood in the vessel being accessed is accomplished by merely subjecting the blood stream to contact with the agent rather than by relying on diffusion across a membrane and subsequent diffusion in the blood stream. The effects of this contact are predominantly in situ or local effects.

When the physiologically active agent is heparin, in situ prevention of clot formation is preferably achieved by subjecting the blood stream to contact with heparin in a heparin immobilizing biocompatible material at the delivery end of the impermeable occlusal balloon. Heparin immobilizing materials include polyvinyl alcohol; surface-modified polymeric biomaterials with poly(ethylene oxide), albumin, and heparin; derivatized dextrins; polymers with hydrophilic spacers; vinyl-pyridine-grafted styrene-butadiene-styrene triblock copolymer; and dimethyl-amino-ethyl-methacrylate-grafted styrene-butadiene-styrene triblock copolymer.

Furthermore, a multifunctional thrombo-resistant coating can be incorporated on the delivery end of an occlusal balloon. Such a coating may include a siloxane surface onto which a plurality of amine functional groups have been bonded. Covalently bonded to the amine functional groups are a plurality of poly(ethylene oxide) chains, such that a single poly(elthylene oxide) chain is bonded to a single amine functional group. A plurality of different bioactive molecules, designed to counteract specific blood-material incompatibility reactions, are covalently bonded to poly (ethylene oxide) chains, such that a single bioactive molecule is coupled to a single poly(ethylene oxide) chain. Methods of manufacturing these materials have been previously described. See, for example, International Patent Applications Nos. PCT/US89/01853 and PCT/US91/02415, which are herein incorporated by reference in their entirety. The resulting siloxane that is so manufactured contains a plurality of different bioactive molecules capable of reacting with blood components which come in proximity to the siloxane surface in order to resist blood-material incompatibility reactions.

In the balloon occluder embodiments of this invention with a semipermeable membrane, the physiologically active agent is effective at the release site, namely in situ. The dosage can be regulated so that the active agent is effective systemically because the active agent circulates with the bloodstream. These sources of physiologically active agents are herein described as permeating sources of physiologically active agents and such sources may be utilized with any of the embodiments disclosed herein. The dose required to achieve the anticoagulant effect locally is much less than a systemically therapeutic dose, thus the long term risk associated with in situ effects is less than the risk associated with full systemic anticoagulation.

When the physiologically active agent is provided by immobilizing it on an impermeable occlusal balloon, the active agent is predominantly effective in situ, at or near the contact site. Such sources of physiologically active agents are herein described as in-situ sources of physiologically active agents. They include embodiments of the delivery end of an occlusal balloon on which the physiologically active agent is attached at the outer surface that is exposed to the blood flow.

In addition, other embodiments of this invention incorporate an impermeable balloon that provides a source of at least one physiologically active agent whose effects are manifested in situ and systemically without transport across a semipermeable membrane. In these embodiments, the physiologically active agent is typically released by a substance that is incorporated on the delivery end of the occlusal balloon that is exposed to the blood flow. These sources of physiologically active agents are herein described as non-permeating sources of physiologically active agents. For example, when the physiologically active agent is an anti-coagulant, nitrogen oxide (NO) releasing polymers can be incorporated on the delivery end of the occlusal balloon so that NO is released into the bloodstream. Examples of NO-releasing polymers include diazeniumdiolates added to plastics such as polyvinylchloride and polyurethane. In this case, diazeniumdiolates include specific compounds such as sodium 1-(N,N-diethylamino)diazen-1-ium-1,2-diolate, disodium 1-[2(S)-carboxylatopyrrolidin-1-yl]diazen-1-ium-1,2-diolate, sodium 1-(piperazin-1-yl)diazen-1-ium-1,2-diolate, and 1-{N-methyl-N-[6-(N-methylammonio)hexyl]amino}diazen-1-ium-1,2-diolate.

The features of each one of the herein described embodiments of the occlusal balloon are not meant to be exclusive of features of other embodiments that can be incorporated in the same occlusal balloon to render a functional combination. For example, an occlusal balloon with a semipermeable membrane can also incorporate a source of a physiologically active agent for predominantly in-situ effects, and/or incorporate a source of a physiologically active agent for in situ and systemic effects of the type described in relation to embodiments of nonpermeable occlusal balloons.

Some embodiments of this invention may be provided with more than one occlusal balloon. When more than one agent is to be provided, the range of molecular weights of such agents may be so broad that a single membrane might not be adequate for the diffusion of the different agents into the blood stream. Even if a single membrane were adequate, conditions to be satisfied regarding the replacement, mixing and compatibility of the agents might require that they be kept in different occlusal balloons. In such an arrangement, for example, a first occlusal balloon may contain an aqueous solution of albumin and heparin. Heparin would be delivered into the bloodstream by diffusion across a semipermeable membrane at delivery end and the balloon would be kept inflated by osmotic pressure due to the diffusion of an aqueous fluid across the same membrane into the interior of the balloon.

A second occlusal balloon may be used within the same access tube that is adjacent to or circumferentially positioned around the first balloon. In such embodiments, the second balloon may contain a solution of one or more physiologically active agents, such as medications, that can be delivered into the bloodstream by diffusion across a semipermeable membrane at the delivery end of that balloon. Thus, if one balloon delivers heparin, then the other balloon may be utilized for slow diffusion of small molecular weight solutes, such as medication that requires parenteral administration, including antibiotics, small peptides, and hormones.

It is understood that elements of any embodiment of the vascular access system according to this invention may be provided with suitable radio-opaque markings so that its location or particular configuration can be externally observed. These markings can be particularly useful when incorporated in the vascular graft or in the occlusal balloon.

Figure 3A:
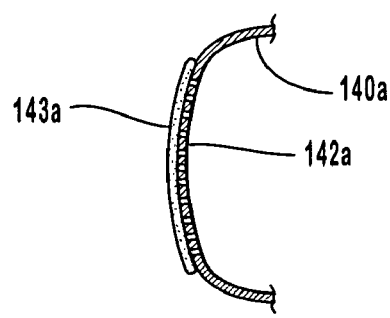

FIG. 3A depicts a cross-sectional view of a balloon 140a that has a portion with holes formed therethrough and a semipermeable membrane 143a laminated thereon. Semipermeable membranes used in different embodiments of this invention can be attached to the delivery end of the occlusal balloon with or without a backing that provides structural support, depending on the type of membrane being used. Also, the occlusal balloon material at the delivery end can in some embodiments provide structural support to the semipermeable membrane or vice versa.

Figure 3B:
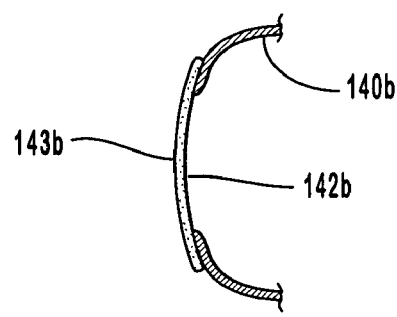
Figure 3C:
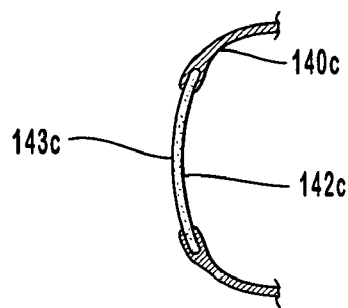
Figure 3D:
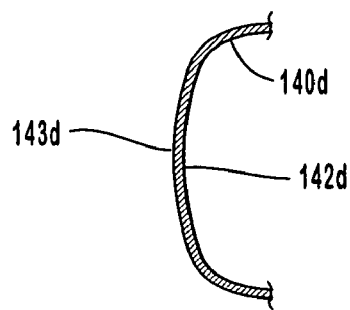

FIGS. 3B and 3C respectively depict cross-sectional views of a semipermeable membrane 143b and 143c attached to an occlusal balloon 140b and 140c, similar to semipermeable membrane 243' shown in FIGS. 2A–2B. Occlusal balloon 140b has a delivery end 142b onto which semipermeable membrane 143b is attached. Occlusal balloon 140c is provided with features that brace the edges of semipermeable membrane 143c. FIG. 3D depicts an occlusal balloon 140d like occlusal balloon 240 that has an integral semipermeable region 143d. In one embodiment, balloon 140d is made of, for example, PTFE that is impermeable to the solvent and solute or solutes in the occlusal balloon, and the delivery end of the balloon is made of porous PTFE that embodies semipermeable region 143d.

In addition to single layer and bi-layer configurations described above for the disposition of the semipermeable membrane at the delivery end of the occlusal balloon, other configurations are also possible. These additional configurations include a tri-layer configuration and configurations in which the semipermeable membrane is sandwiched between two layers of material, one at each side of the membrane, that allow for the passage of fluid from and to the membrane.

Preferably, the shape of the functional portion of the semipermeable membrane used in some embodiments of this invention is generally circular, in which case corresponding features at the delivery end of the occlusal balloon are also generally circular. These shapes, however, are not unique or determinative of the characteristics and functions of the balloon occluder embodiments of this invention, and other geometrical shapes can also be used, particularly when the base materials or manufacturing tools can more efficiently be used with noncircular membranes.

The occlusal balloon of specific embodiments of this invention at its delivery end and the membrane or membranes therein located present a generally curved surface that slightly protrudes out of the occlusal balloon's body. This generally curved surface is preferably convex on the side exposed to the bloodstream of the vessel being accessed. This preferred shape is consistent with the slightly greater pressure within the occlusal balloon relative to the vascular pressure in the blood vessel being accessed by an embodiment of a device according to this invention.

Although a variety of techniques can be relied on to attach a semipermeable membrane to the delivery end of an occlusal balloon as shown in FIG. 3B, a preferred technique comprises the steps of placing a protective material between occlusal balloon delivery end 142b and semipermeable membrane 143b and bonding, preferably with a biocompatible adhesive, a contour of semipermeable membrane 143b to the terminal end of the occlusal balloon. The occlusal balloon, which may be formed from expandable material such as silicone or latex, is subsequently cut, thus obtaining a type of configuration wherein the functional region of the semipermeable membrane is typically surrounded by small non-functional portions bound to the occlusal balloon material by an adhesive.

FIGS. 4A–4B depict an embodiment generally referenced at 100" that has an balloon occluder 240" that extends integrally from an access tube, shown as graft vessel 220 in the figures. One advantage of the configuration shown in FIG. 4A is that chamber 228 can be relatively large. The length of chamber 228 permits device or system 200 to be utilized for a long period of time. Additionally, tube 260 may be configured to be puncture-resistant such that as needle 120 is introduced into lumen 226, or more specifically chamber 228, it does not puncture tube 260. Tube 260 is preferably formed from a nickel/titanium alloy as such alloys are flexible and have memory. However, tube 260 can be formed from any suitable material such as metals and plastics.

Another advantage of apparatus 100" is the ability of balloon 240" to remain in position. More particularly, since occlusal balloon 240" and graft vessel 220 are integral, occlusal balloon 240" cannot migrate out of the graft vessel and into the blood vessel over time as the balloon is repeatedly inflated and deflated and as fluid is flushed through graft vessel 220 over the deflated balloon. When the occlusal balloon and the graft vessel are not integral, it may be necessary in some instances to prevent the occlusal balloon from migrating out of the access tube and into the blood vessel. Such migration can be prevented by deploying an appropriate stent at the anastomosis site with the balloon abutting the side of the stent. An example of an appropriate stent is disclosed in U.S. Pat. No. 5,456,712 issued to Maginot.

The access tubes may be anastomosed to blood vessel 10, or another anatomical vessel, via any known or hereafter developed technology, including via a compression plate apparatus as shown at 310 in FIGS. 2A–2B or 310' in FIGS.

4A–4B. Details regarding the compression plate apparatus are provided in co-pending U.S. patent application Ser. No. 09/737,200, titled "Compression Plate Anastomosis Apparatus and Related Systems," which was filed on Dec. 14, 2000 and in U.S. Pat. No. 6,569,173 titled "Compression Plate Anastomosis Apparatus." Methods, systems and devices for anastomosing a graft vessel to a blood vessel are also disclosed in U.S. Pat. No. 6,248,117 and in U.S. patent application Ser. No. 09/736,839, titled "Intraluminally Directed Anvil Apparatus and Related Methods and Systems," which was filed on Dec. 14, 2000. Each of these applications is hereby expressly incorporated by reference in their entirety.

The present invention, however, does not require a specific anastomosis technique for its implementation. In fact, the access tube of the invention may simply be sutured directly to an anatomical vessel, with or without the help of an anastomosis component. Accordingly, no specific structure is shown for joining the access tube to the vessel in many of the drawings.

Like the other balloons discussed above, balloons that extend integrally from a vessel may be formed such that the balloon is impermeable. Additionally, a balloon that extends integrally from a vessel may be formed by any suitable method and from any appropriate material.

Figure 5:
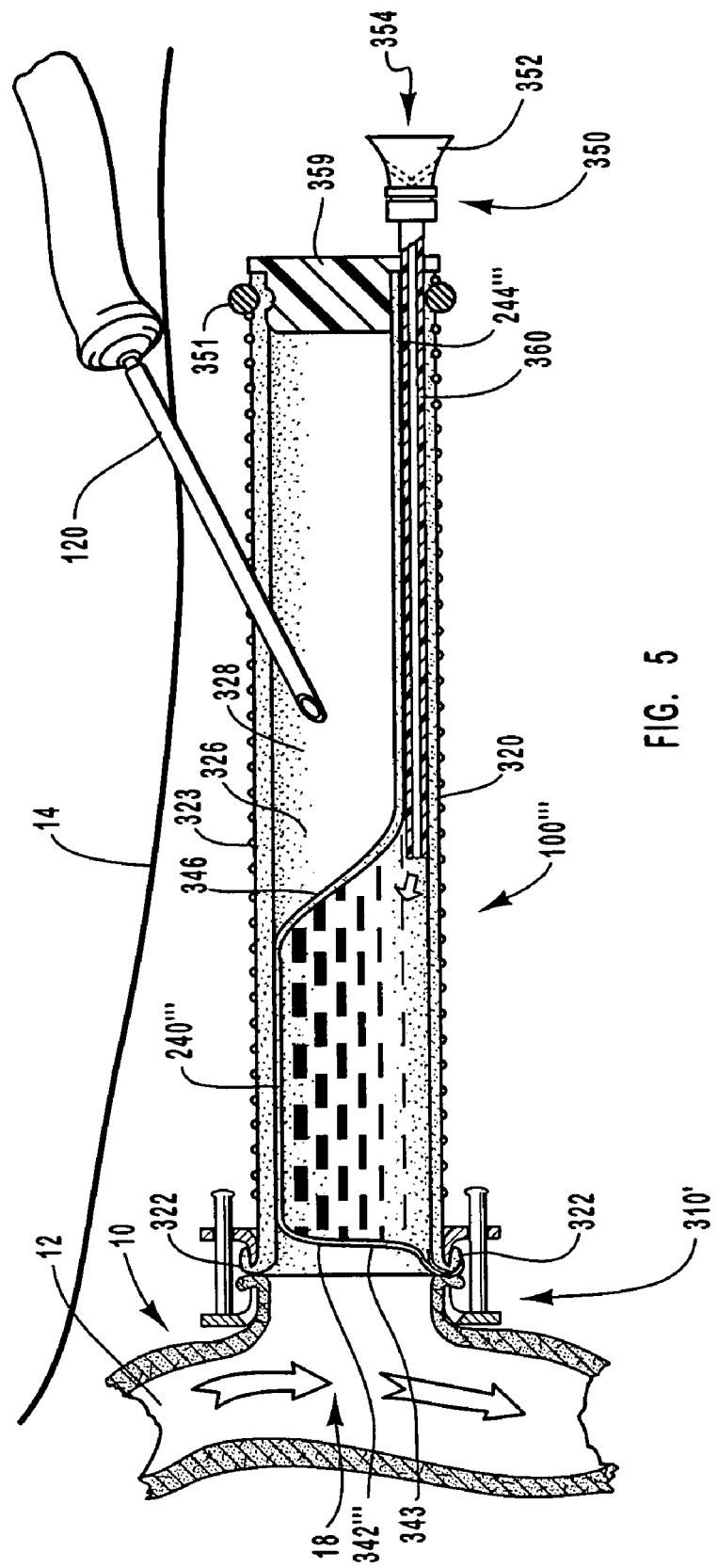
FIG. 5 is a partial cross-sectional view of an embodiment of a vascular access system with a balloon occluder that has a valved coupler port.

FIG. 5 depicts another embodiment at 100'''. Balloon 240''' is coupled via a coupling tube 360 that terminates at a coupler port 350, another embodiment of a port device. Coupler port 350 is adapted to couple with a needle in a manner such that fluid can be delivered into balloon 240''' or drawn from balloon 240'''. Coupler port 350 has a funnel-shaped chamber 354 that is adapted to direct the needle toward a valve 352 shown in dotted lines that can be penetrated by the needle in order to provide fluid communication with balloon 240'''. Coupler port 350 is a self-sealing port. As described in greater detail below with reference to fluid occluder embodiments, a self-sealing access port can comprise any port device used to repeatedly isolate the conduit from external pressure (outside of the vascular system) to allow an attached access tube to contain fluid when the port is not penetrated and provide fluid communication to the conduit when a needle or other access device penetrates into the access port. A coupler may also be rotated by a needle that is uniquely adapted to engage the coupler by rotating the coupler into an open position for fluid communication. A stop 359 is positioned at the end of graft vessel 320 opposite from the anastomosis end. Stop 359 seals the access tube due to the compression of o-ring 351. In another embodiment, the balloon is directly inflated and deflated by puncturing the balloon through the wall of the graft vessel with a small needle. Similarly, the balloon may be in fluid communication with a fluid chamber that extends a certain length within the graft vessel and acts as a port device. Such a fluid chamber may be defined by the same material as the graft vessel. As a further alternative, stop 359 may be replaced with an access port, again preferably self-sealing, which would allow for access to the chamber inside the access tube lumen when the balloon occluder is distended and for access to the vessel lumen when the balloon occluder is contracted. Such an access port may be configured in a manner similar to the port devices previously discussed.

Vascular access via a system according to some of the balloon occluder embodiments of the invention may be created by first performing a vascular anastomosis to attach an access tube to the anatomical vessel that is being accessed. An occlusal balloon may then be placed within the access tube or be pre-assembled in the access tube. The occlusal balloon may be provided with a port device already attached to it, or the port device may be subsequently attached to the occlusal balloon by conventional techniques. Once a vascular access system according to this invention is placed at the access site, the entire system preferably remains subcutaneously placed for its use in procedures such as dialysis, in particular hemodialysis, and drug delivery. Examples of such external treatment methods are provided in greater detail in U.S. Pat. No. 6,595,941 titled Methods for External Treatment of Blood filed on Jan. 11, 2000 and issued on Jul. 22, 2003, which was previously incorporated by reference.

FIG. 6 schematically illustrates an embodiment of a method for externally treating blood according to this invention. In the embodiment shown in FIG. 6, blood is extracted through an extraction vascular access apparatus such as the embodiment of extraction vascular access apparatus 100"a, and delivered through a delivery vascular access apparatus such as the embodiment of delivery vascular access apparatus 100"b. Note that extraction vascular access apparatus 100"a and delivery vascular access apparatus 100"b are both identical to the apparatus shown in FIGS. 4A–4B. Because the vascular access apparatus of this invention permits multiple vascular access, whether any given vascular access apparatus is employed in any specific treatment episode as an extraction or a delivery apparatus is a matter of convenience and choice. In addition, once blood has been extracted through an extraction vascular access apparatus and there is an available delivery vascular access apparatus to return the blood flow to a blood vessel, such extracted blood can be subjected to hemodialysis or to any other blood treatment. Consequently, the term "hemodialysis" in the context of this invention is understood to broadly refer to external treatment of blood, including an actual hemodialysis treatment, and any other treatment of blood that is performed outside a patient's body, and which requires the extraction, treatment and subsequent delivery of the treated blood to the patient. Of course, as previously discussed, the present invention also allows for accesses of anatomical vessels other than blood vessels. Accordingly, the invention can be used for treatment of other body fluids, or for accessing other body fluids for other purposes.

In FIG. 6, blood vessels 10a and 10b represent the blood vessels involved in the treatment process. When blood is extracted from blood vessel 10a, it is subjected to treatment, and it is subsequently returned to blood vessel 10b. Blood vessel 10a is referred to as the extraction blood vessel and blood vessel 10b is referred to as the delivery blood vessel. Although the apparatus, systems and methods of this invention are suitable for the practice of a variety of external treatments of blood, they are particularly suitable for the practice of vein-to-vein hemodialysis. In this case, blood vessels 10a and 10b would represent the vein from which blood is extracted and the vein to which dialyzed blood is injected, respectively.

An embodiment of an apparatus or system according to this invention is attached to each one of blood vessels 10a and 10b as schematically shown in FIG. 6 by embodiments 100"a and 100"b, respectively. These embodiments are anastomosed at sites 222a and 222b, respectively, and they can be embodiments of any of the vascular access devices and systems of this invention and combinations thereof. For the practice of one method according to this invention, these embodiments comprise occlusal balloons 240"a and 240"b, port devices 250a and 250b, and access conduits 244"a and 244"b that respectively contain occluder access tubes 260a and 260b. It should be apparent that the while FIG. 4 depicts the access tubes as graft vessels 222a and 222b, access tubes need not be a graft vessel, nor must they be self-sealing.

The procedure shown in FIG. 6 facilitates vein-to-vein hemodialysis because the number of venous sites that are available for extended periods of time for the practice of hemodialysis is very limited. Furthermore, the practice of vein-to-vein hemodialysis is a desirable dialysis practice because AV (arterio-venous) graft hemodialysis often leads to venous hyperplasia and stenosis.

Depending on the specific treatment to which the blood is subjected externally, the device that provides such treatment is part of the fluid communication between the extraction vascular access apparatus and the delivery vascular access apparatus. In certain treatments, such as irradiation, the blood flow is exposed to the treating effects without actually being in fluid communication with the device that provides such effects. Since the blood flow must interact in some external manner with the device that provides the treatment, it is said that the fluid communication between the extraction vascular access apparatus and the delivery vascular access apparatus encompasses communication with a blood treating device.

Examples of external blood treatments that can be performed with the present invention include plasmapheresis, cytopheresis, hemodialysis, apheresis, hemoperfusion, and hemofiltration.

In some of these treatments, such as plasmapheresis Calso known as plasma separation or plasma exchangeC, whole blood is removed from the body, the bloods cellular components are separated in a blood treatment device, and subsequently reinfused in a saline solution or some other plasma substitute, thus depleting the body's own plasma without depleting its blood cells. In this case, the external treatment of blood is typically performed with a cell separator.

Plasmapheresis is currently widely accepted for the treatment of myasthenia gravis, Lambert-Eaton syndrome, Guillain-Barré syndrome, and chronic demyelinating polyneuropathy. An average course of plasma exchanges is six to ten treatments over two to ten weeks, with some centers performing one plasmapheresis session per week and other centers performing more than one session per week. Patients undergoing plasmapheresis are typically administered blood anticoagulant medications, and the blood treatment device includes a plasmapheresis separator. Plasmapheresis and cytopheresis are specific instances of the more general apheresis, which is the withdrawal of whole blood from the body, separation of one or more components, and return by transfusion of the remaining blood to the donor.

Hemoperfusion is the technique of passing blood extracted from the body through an extracorporeal sorbent column for the purpose of removing harmful substances. In one practice of hemoperfusion, blood is passed through a blood treatment device that comprises a biocompatible hemoperfusion cartridge that contains activated carbon adsorbent coated with an antithrombogenic heparin-hydrogel. This technique permits the removal of a variety of toxins in the blood, and it is used in the treatment of drug overdoses, hepatic failure, encephalopathy, and removal of chelated aluminum from hemodialysis patients.

Hemodialysis is one of the more common forms of dialysis conventionally used. In hemodialysis, a hemodialyzer, or artificial kidney, takes the place of failed kidneys. Patients with chronic kidney or renal failure need dialysis to remove excess urea, fluid, electrolytes, minerals, and other wastes form the blood stream since the kidneys cannot perform this cleansing. In this case, the external treatment of blood is typically performed with a hemodialyzer as a blood treatment device. An ultrafiltration hemodialyzer is a hemodialyzer that uses fluid pressure differentials to typically bring about loss of protein-free fluid from the blood to the bath, as in certain edematous conditions.

With hemofiltration, patients have fluid and waste products removed from the blood at a constant rate, twenty-four hours a day, for as long as necessary, with the aid of a blood treatment device that comprises a hemofiltration cartridge. This technique is typically used on patients for whom hemodialysis is not considered safe, and also to treat conditions such as uremia, acute renal failure, refractory fluid overload, and massive edema.

Embodiments of this invention that are provided with chambers, such as those shown at 228a and 228b in FIG. 6, would in principle permit the puncturing of the corresponding graft vessels prior to the deflation of the corresponding balloons. However, as indicated above, in embodiments of the invention in which the access tube itself is punctured with a needle, the occlusal balloons are preferably deflated prior to the puncturing of the respective access tubes. Similarly, any puncturing device inserted through the walls of the access tubes is preferably removed prior to the distension of the respective occlusal balloons.

As indicated, embodiments 100"a and 100"b can be additionally used to intravenously deliver medication while at least one of them is anastomosed, and this goal can also be achieved after both embodiments 100"a and 100"b have been anastomosed for hemodialysis.

The sequence of steps related to the expansion/contraction of the occlusal balloons, the replacement of any fluid within graft vessels 222a and 222b, and the optional intravenous delivery of medicine can be performed according to the methods of this invention in any desired biocompatible order.

Referring now to FIGS. 7A–7C, yet another embodiment of a balloon serving as the occluder of the invention is disclosed. In this embodiment, indicated generally at 200, the balloon 340 is a toroidal-shaped balloon, which is in fluid communication with a port device 510. As shown in the figure, the port device 510 is attached to a port tube 468, which is attached at its opposite end to an access tube connector 480. Similar to other embodiments of balloon occluders disclosed herein, the balloon 340 can be selectively distended and contracted to allow for access to the body fluid within anatomical vessel 10 by way of access tube 110. A stop 359' may be placed at the end of access tube 110 opposite from the anastomosis end. Of course, access tube 110 can also be formed with a closed end that is integral to its sidewalls so that a stop is not needed.

As shown in FIG. 7A, any of the fluids previously discussed, or any other fluid suitable for distending a balloon occluder, can be inserted into port device 510, which is preferably self-sealing, by using a needle or other similar device. As indicated by the arrows, this fluid flows through port tube 468 and into the toroidal-shaped balloon via access tube connector 480. It is preferable that enough fluid be inserted into balloon 340 such that the body fluid within vessel 10 cannot leak past balloon 340 and into the access tube 110.

When access to the body fluid within vessel 10 is desired, the fluid used to distend balloon 340 can then be withdrawn, leaving the balloon in a contracted state, as shown in FIG. 7B. Once the balloon is in this state, the body fluid in vessel 10 may then be accessed by inserting a second hypodermic needle 120 or similar device into access tube 110, as depicted in FIG. 7C. Of course, another needle may be inserted in the same or a separate access tube to insert the body fluid back into vessel 10. Or, as previously discussed, needle 120 can be used to insert medications or other pharmacological agents into vessel 10.

As an alternative to the embodiment shown in FIGS. 7A–7C, the stop 359' may be replaced with a second port device or access port, as shown in FIG. 9. In such embodiments, the access tube itself need not be self-sealing, as needle 120 can be inserted into the second access port to withdraw and/or insert blood. Such a second port device may be attached to access tube 110 in the same configuration as the port device shown in FIG. 18C.

In FIGS. 8A–8B, the toroidal-shaped balloon occluder embodiment of the device is shown in greater detail. Balloon 340 may be attached to the interior of the conduit of access tube 110 with any suitable adhesive or other manner of attachment at the region of balloon 340 indicated at 344 in FIG. 8B. Balloon 340 may also be integral with other components of the device such as access tube 110. The opposite end of balloon 340, in particular the region indicated at 346, may then be adhesively attached to and/or everted around the anastomosis end 472 of access tube connector 480. When so configured, the region of balloon 340 indicated at 345 may then expand into a toroidal shape, as shown in FIG. 7A, upon introduction of an appropriate fluid into balloon 340, thereby blocking fluid communication between the access tube 110 and the anatomical vessel 10. Accordingly, balloon 340 may simply be a tubular-shaped piece of suitable elastic biocompatible material, such as rubber, silicone, polytetrafluoroethylene (PTFE), particularly expanded PTFE (ePTFE), latex, polyurethane, combinations of these materials, or any other suitable material. Of course, balloon 340 may have any suitable shape and may be integrally formed or attached in any appropriate configuration for occlusion of the anastomosis opening or access tube 110.

Port device 510 is connected with port tube 468 by fitting port tube 468 over port connector 455. The opposite end of port tube 468 is fit within tube fitting 485, which can be attached to or integral with access tube connector 480.

Access tube connector 480 may also be configured to receive an anastomosis device, or a component of an anastomosis device. For example, the embodiment depicted in FIGS. 8A–8B shows anastomosis ring 40, the posts 42 of which fit within slots 482 in access tube connector 480. Anastomosis ring 40 also has tabs 46, which facilitate the anastomosis procedure and are discussed in greater detail later.

FIG. 9 schematically depicts a blood treatment method utilizing a balloon such as a toroidal-shaped balloon occluder tethered to a port device as described above in relation to FIGS. 7A–7C. Blood from extraction blood vessel 10a is extracted from access tube apparatus 200a and is subjected to external treatment of some kind. This blood is subsequently returned to delivery blood vessel 10b by way of access tube apparatus 200b.

Each of the balloons disclosed herein is an example of occluding means for selectively occluding an opening in an anatomical vessel or more particularly balloon means for selectively occluding an opening in an anatomical vessel. Examples of such balloon means according to this invention include: occlusal balloons such as nonpermeable occlusal balloons, occlusal balloons that have an integral permeable region, occlusal balloons with a semipermeable membrane, occlusal balloons with radio-opaque markings, occlusal balloons that are inflated with a liquid, occlusal balloons that are inflated with a gas, occlusal balloons that are configured to operate in conjunction with or in the presence of at least another occlusal balloon, and toroidal-shaped occlusal balloons.

Each embodiment of a means for selectively occluding an opening in a blood vessel functions according to this invention by adopting a variety of configurations such as a distended configuration and a contracted configuration. In particular, the distended configuration can be an inflated configuration, and the contracted configuration can be a collapsed configuration. Preferably, the distended configuration is adopted when an embodiment of a balloon means is filled with a liquid, although the fluid filling some of such embodiments can also be a gas. Blood from the accessed vessel cannot infiltrate into the anastomosed access tube when the embodiment of the balloon means for selectively occluding an opening is in its distended configuration, whereas fluid communication from the interior of the anastomosed access tube into the lumen of the accessed anatomical vessel is allowed in the contracted configuration of the same embodiment. Any of such specific embodiments is manufactured so that it can change from any one of these particular configurations to the other and vice-versa a plurality of times. The number of times which these changes in configuration are experienced by embodiments of the balloon means can be of the order of the number of injections that a blood vessel or other anatomical vessel would typically be subjected to during a long term treatment of a chronic affliction or during dialysis treatment.

Examples are also provided herein of a means for selectively and controllably exposing blood flow to an agent in a vascular access. Means for selectively and controllably exposing blood flow to an agent according to this invention are embodied by means for selectively effectuating transport of an agent in a vascular access, and by means for selectively subjecting blood flow to contact with an agent. Exemplary embodiments of each one of these means are enumerated in turn below.

Means for selectively effectuating transport of an agent in a vascular access or at an anastomosis site according to this invention is embodied by permeating sources of physiologically active agents or other agents. These permeating sources are more specifically embodied by sources such as a semipermeable membrane attached to an occlusal balloon or a semipermeable region of an occlusal balloon. Occlusal balloons having an integral semipermeable region or an attached semipermeable membrane may be generically referred to as occlusal balloons having a semipermeable portion. Such semipermeable portions are exemplified by semipermeable membrane 243' shown in FIGS. 2A–2B and 143a–c shown in FIGS. 3A–3C or a plurality of semipermeable membranes, such as semipermeable membranes in any of a mono-layer, bi-layer, tri- or generally multi-layer and sandwiched configurations.

Each embodiment of a means for selectively and controllably exposing blood flow to an agent in a vascular access is integrally formed in or attached to the delivery end of an embodiment of a balloon means according to this invention. The means for selectively and controllably exposing blood flow to an agent in a vascular access functions according to the present invention by exposing the blood flow at the anastomosis site to at least one physiologically active agent, such as a substance that will prevent the formation of blood clots. Means for selectively and controllably subjecting blood flow to contact with an agent according to this invention is embodied by in-situ sources of physiologically active agents and by nonpermeating sources of physiologically active agents.

Many examples are also provided herein of a means for selectively providing access to a balloon means or other means for selectively occluding an opening in a blood vessel. Examples of means for selectively providing access to a balloon means or other means for selectively occluding an opening in a blood vessel include: port devices such as a port device with one self-sealing access cavity, such as port device 150 shown in FIG. 1, 150' shown in FIGS. 2A–2C, port device 250 shown in FIGS. 4A–4B, a port device with a plurality of self-sealing access cavities, port 354 shown in FIG. 5, port device 510 shown in FIGS. 7A–7C, and a port device that includes ports for providing conduits to operate probes, sampling devices, imaging devices, etc. Any of these port devices, or any other such devices suitable as a port, can be used as an access port to access the body fluid in an anatomical vessel by way of an anastomosed access tube. Each embodiment of the means for selectively providing access is provided with at least one self-sealing cavity or valve for selectively allowing fluid communication with means for selectively occluding an opening in a blood vessel.

Each embodiment of the means for selectively providing access to a balloon means or other means for selectively occluding an opening facilitates the external introduction into or the extraction from a specific embodiment of the means for selectively occluding an opening of fluid therein contained. The fluid communication between an occluding means and the means for selectively providing access to an occluding means enables subcutaneous placement.

The anastomosed access tube of this invention may provide physical support to a particular embodiment of the means for selectively occluding an opening and to a particular embodiment of the means for selectively providing access to a means for selectively occluding an opening. In preferred embodiments, this support is provided by a housing such that the anastomosed access tube contains in its interior an embodiment of a means for selectively occluding an opening.

FIGS. 10–15 illustrate various other embodiments of the present invention utilizing removable plug occluders. In these embodiments, the access tubes have an access end opposite from the anastomosis end. It is preferable in these embodiments that the access end be configured to extend percutaneously and be extracorporeally accessible. Each of the plugs disclosed herein with reference to FIGS. 10–15 is an example of occluding means for selectively occluding an opening in an anatomical vessel or more particularly plug means for selectively occluding an opening in an anatomical vessel.

FIG. 10 shows two separate access tubes anastomosed to the sidewalls of two separate target blood vessels, identified at 10a and 10b in the figure. As with the other embodiments, the anastomosis of the access tubes to the vessels can be done by any suitable methodology, including suturing, stapling, welding, clamping, use of adhesives, anastomosis rings and/or plates, or any other anastomosis technology currently known in the art or hereafter invented. However, in the embodiment depicted in FIG. 10, an anastomosis ring is used, which is attachable to the access tube device, in combination with another similar ring attached to, or integrally formed with, the access tube. The method for deploying this embodiment involves the use of an external anastomosis operator, which is discussed in detail in co-pending application Ser. No. 10/351,172, titled "Apparatus and Methods for Occluding an Access Tube Anastomosed to Sidewall of an Anatomical Vessel", which was filed on Jan. 23, 2003, the disclosure of which is hereby expressly incorporated by reference. The anastomosis ring is discussed in greater detail later in relation to the access tubes.

Regardless of the methodology used to attach the access tube to the target vessel, however, it is preferable that the access tube not extend significantly into the target vessel lumen so as to disrupt the flow of blood or other body fluid in the vessel lumen. Accordingly, as the term is used in this context, an access tube can extend into a target vessel without extending "significantly" therein if the flow of body fluid in the access-tube region is not disrupted to the degree that it would cause complications. The accompanying figures depict embodiments of the invention with access tubes that do not extend at all into the target vessel lumen. Note, however, that the access tubes of other embodiments may extend slightly into the target vessel lumen and still be considered to not extend significantly therein. While an access tube in accordance with the invention may still extend slightly into the target vessel lumen, it should not extend into the lumen to a degree such that the cross-sectional area of the lumen near the access tube is decreased significantly. Moreover, the access tubes of some embodiments may not be flush with the remainder of the target vessel wall, and yet are still able to avoid extending significantly into the target vessel lumen. Some embodiments of the device may sit recessed from adjacent portions of the target vessel so as to stretch the target vessel somewhat. Other embodiments may be configured such that the device is offset or recessed from the stream of body fluid in the lumen, as shown in several of the accompanying figures. While not depicted, it is possible that some other embodiments may sit against the target vessel so as to deform the target vessel lumen radially inward. In other words, the device may deform the target vessel by compressing the vessel from the outside while still avoiding extending into the target vessel. The device, however, should not deform the target vessel lumen to the extent that that complications arise due to constriction of the vessel lumen.

The first access tube apparatus, or extraction access tube apparatus 300a, extends from first target blood vessel 10a percutaneously—or through an incision 15 in the patient's skin—such that the access end of the first access tube is extracorporeally accessible at a first access location. Likewise, the second access tube apparatus, or insertion access tube apparatus 300b, extends from second target blood vessel 10b percutaneously such that the access end of the second access tube is also extracorporeally accessible at a second access location.

When access to the blood or other body fluid in the target vessel is not needed, and as best seen in subsequent figures, a removable plug occluder 90 having an occlusion end 92 blocks fluid communication between each of the blood vessels and the access tube conduits. In this way, when access to the blood is desired for treatment or any other reason, one need only remove the plug occluders from the access tube conduits to gain access.

The extracorporeally accessible ends of the access tubes may be sutured or otherwise affixed to the patient's skin. As illustrated by FIG. 10, embodiments of the removable plug embodiment of the present invention may be configured to be sufficiently flexible so as to allow for convenient safe-keeping of the device between uses. In such embodiments, affixing the device to the patient's skin serves to mitigate interference with the patient's everyday activities caused by the device. For instance, this feature would minimize disturbances caused by the patient's clothing with the device. In addition, it would serve a safety function, helping to prevent the device from being pulled off of the target vessel.

As should be apparent, the present invention allows for enormous flexibility in the placement positions of the access tubes. While the embodiment shown in FIG. 10 has the extraction access tube apparatus 300a anastomosed to the jugular vein in the patient's neck and the insertion access tube apparatus 300b anastomosed to the subclavian vein, countless variations are possible. To illustrate, each of the access tubes could be anastomosed to any of the various other veins and/or arteries of the body, such as those in the arms, legs, shoulders, neck, or elsewhere.

Moreover, the access tubes of the invention need not even be attached to separate vessels. FIG. 12 shows another embodiment of the occludable access tube apparatus wherein the extraction access tube apparatus and the insertion access tube apparatus are anastomosed to the same vessel 10 at separate locations, one downstream from the other. It should now be apparent that the precise location and type of vessel to which the device may be anastomosed may vary considerably.

In FIG. 11A, each of the two access tube apparatus is shown at its anastomosis site with its respective plug occluder 90 in an occluding position within its respective access tube conduit 70a and 70b. The access ends 60 of the devices are seen extending through the patient's skin 30. At the occlusion ends 92 of the occluders 90 is a plug 53, which serves to seal the access tube conduit 70 from the target vessel lumen. Plug 53 typically comprises a face 89, one or more sidewalls 88, and a top surface 87, as best seen in FIG. 13A.

As can be seen FIG. 11A, the only non-native material exposed to blood flow in the vessels comprises an exposed portion 93 of the plug 53 at the occlusion end 92 of each occluder 90. The precise surface area termed herein as exposed portion 93 will vary depending on the precise configuration of the system. Typically, however, exposed portion 93 will comprise face 89 and in some instances a portion (preferably small) of the plug sidewalls 88. "Non-native" materials, as the term is used herein, are those materials that have been introduced into the patient as part of the disclosed procedures—i.e., they are foreign materials that were not already present in the patient before introducing the access tube apparatus. Because either the entire occluder 90 or at least plug 53 at the occlusion end 92 of each occluder is replaceable, the only non-native surface area exposed to the blood stream is replaceable. This aspect of the invention helps to minimize infection, thrombosis, and other complications at the anastomosis site.

Moreover, to further reduce the incidence and likelihood of such complications, the face 89 of plug 53, or the entire plug 53, including sidewalls 88 and top surface 87, may be coated with pharmacological agents, including, but not limited to, antibacterial agents to prevent infection, anti-thrombotic agents to prevent thrombosis formation, and/or antiproliferative agents to prevent neo-intimal hyperplasia or other potential problems. The embodiment depicted in FIG. 11A has such a coating 99 on the face 89 and also on the sidewalls 88. A typical agent used for these coatings is an anticoagulant such as heparin or modified heparin compounds such as Duraflow II produced by Edwards Life Sciences. Antibacterial agents that have been shown to provide an effective short-term infection barrier when applied as a coating include chlorhexadine and silver sulfadiazine. Drug-eluting coatings containing antiproliferative agents, such as paclitaxel, have been shown to be beneficial in preventing restenosis due to neo-intimal hyperplasia. However, any pharmacological substance known to those skilled in the art now or hereafter could be used as a coating.

As an alternative, some agents or substances could be integrally formed with, or otherwise incorporated into, plug 53 or a portion thereof. Applying a coating 99 on the face 89 and sidewalls 88 of the plug 53 ensures that the only surface area exposed to blood flow in the target vessels—or exposed portion 93—is not only replaceable, but also coated with agents designed to minimize the complications discussed herein. As should be apparent, any of these coatings, including antithrombotic, antiproliferative, antimicrobial coatings can be considered means for preventing complications at the anastomosis site.

Additionally, as shown by the embodiment of the access tube apparatus depicted in FIG. 14 at 300', such coatings may extend to the interior wall 72 of the access tube conduit 70. Interior wall coatings 73 may, like other disclosed coatings, comprise pharmacological and/or antibacterial agents or, alternatively, they may comprise a lubricant or other material used to facilitate sliding the occluder 90 in and out of the access tube conduit 70. In addition, any of the various coatings discussed may be applied to other portions of occluder 90. For instance, in an embodiment in which the interior wall 72 of the access tube conduit 70 is coated, the exterior wall of the stem 94 of the occluder 90 may also be coated with similar pharmacological and/or antibacterial agents. Again, it is possible for any of the agents discussed to be integrally formed with, rather than coated upon, any of the access tube portions discussed.

FIG. 11B shows a close-up of the interface between a removable plug embodiment of an access tube apparatus and the target blood vessel. As indicated by the figure, plug face 89 is preferably approximately flush with the native vessel wall such that it alone comprises exposed portion 93. However, it will typically be the case that a relatively small portion of plug sidewall 88 will also comprise exposed portion 93. Still, it is desirable to provide a relatively smooth surface exposed to blood flow that is approximately flush with the vessel walls in order to reduce turbulence and other flow disturbances in the blood flow. Minimizing such disturbances is a significant factor in reducing thrombosis at the anastomosis site. Accordingly, it is preferable that when the occluder 90 is in its occluding position—i.e., it is fully inserted into the access tube lumen—plug 53 extends as far as possible through the access tube lumen but not so far that it extends significantly into the blood vessel lumen and disrupts the blood flow therein. However, due to the replaceable nature of the occluder, and in part to the optional pharmacological coatings on the exposed portion 93, the plug face 89 does not necessarily need to be flush with the vessel wall. In other words, because other aspects of the invention serve to control potential complications at the anastomosis site, embodiments wherein plug 53 extends into the vessel lumen or wherein the plug face 89 sits recessed or extended from the vessel wall are within the scope of the present invention.

In FIG. 11C the access tubes are shown with their occluders removed to allow for vascular access for blood treatment. As the arrows in the figure indicate, blood flows from blood vessel 10a into the access tube conduit 70a of occludable extraction access tube apparatus 300a and is drawn to a blood treatment device. After the blood has been treated, it is inserted into blood vessel 10b via the access tube conduit 70b of occludable insertion access tube apparatus 300b. Typically, and as shown in FIG. 11C, the access ends 60a and 60b of the devices are adapted to be fitted with corresponding access couplings 64a and 64b during blood treatment, which are adapted to be fitted on their opposing ends to a blood treatment device.

Referring now to FIG. 12, the extraction access tube apparatus 300a is anastomosed to blood vessel 10, and the insertion access tube apparatus 300b is anastomosed to the same blood vessel 10 at a downstream location. Otherwise, the embodiment shown in FIG. 12 is identical to that shown in FIG. 11C. Again, as indicated by the arrows, blood from blood vessel 10 is drawn through access tube conduit 70a and into a blood treatment device, after which it is re-inserted into blood vessel 10 through access tube conduit 70b.

FIGS. 13A–13B provide a more detailed depiction of the plug occluder embodiment of the access tube apparatus of the present invention shown in FIGS. 10–12, but with its occluder 90 withdrawn from the access tube conduit 70. Access tube 110 has an anastomosis end 80 opposite from an access end 60. A conduit 70 extends from the anastomosis end 80 to the access end 60. The access tube 110 and conduit 70 therein can be of any cross-sectional shape and size.

The access tubes of the present invention should have an anastomosis end that is adapted for attachment to the sidewall of a vessel. An access tube has an anastomosis end adapted for attachment to the sidewall of a vessel if it is suitable for attachment there. An anastomosis component, such as an anastomosis ring, plates, etc., can facilitate the attachment, or the access tube can have preformed holes at the anastomosis end for suturing. The foregoing components and any others available to one of skill in the art are all examples of means for facilitating anastomosis of an access tube to a vessel. Another example of an access tube with an anastomosis end adapted for attachment to the sidewall of a vessel is an access tube that is soft enough to be punctured by standard suturing procedures, such as a graft vessel. The portion of the access tube defining the conduit 70 is typically made of a flexible and blood-compatible material, such as polyurethane or silicone. However, it could be made of any other blood-compatible material.

Although not necessary, using a flexible material to form the portion of access tube 110 defining the conduit 70 may be desirable for a number of reasons. As discussed earlier, providing a flexible access tube allows the percutaneous portion of the tube to be flexed and pressed against the skin, perhaps even affixed to the skin, when not in use. This contributes to the inconspicuousness of the device and for that reason alone may be desirable from a patient's perspective. It also may assist in keeping the percutaneous portion of the device from being pulled or otherwise disturbed by the patient and his surroundings while conducting everyday activities, and further may prevent or at least mitigate injury to the patient when the device is inadvertently bumped against external objects.

If desired, the access tube may also be formed from more than one material. For instance, the portion of the access tube that is to remain in a subcutaneous position may be made of a more rigid material, while the portion that is to remain in an extracorporeally accessible position may be made of a more flexible material. In such an embodiment, cuff 75 (discussed later) could serve as the interface between the subcutaneous material and the percutaneous material. Or, to achieve a similar configuration, the subcutaneous portion could have a greater wall thickness than the portion that is to remain extracorporeally accessible.

When made from a flexible material, the access tube can be positioned such that it protrudes from the skin at a location remote from the anastomosis site. In such embodiments, the access tube is inserted into the skin at a desired location and then routed underneath the skin to a desired target vessel. This allows the access end 60 of the access tube to be positioned at a safe and comfortable location as desired.

Conduit 70 of the access tube may also be tapered such that it has a circumference at the anastomosis end that is smaller than the circumference of the conduit at the control end. Such a configuration may assist in making a fluid-tight seal at the anastomosis site, particularly for plug occluder embodiments of the invention.

The access end 60 of the access tube 110 has a cap base 61 for engaging an access cap 63 of the occluder 90. The cap base may comprise any configuration suitable for engaging a portion of the occluder 90—preferably an access cap 63—to keep the occluder 90 within the access tube conduit 70 and prevent the occluder 90 from being inadvertently withdrawn. To achieve this, cap base 61 may be configured to allow for a snap-fit, threaded, friction-fit or other suitable junction between it and the access cap 63. As shown in FIG. 13A, one embodiment utilizes threads 62 to threadably engage access cap 63.

As shown in FIGS. 13A–13B, the anastomosis end 80 of the access tube is configured to be attached to an access tube anastomosis ring 85, which is adapted to cooperate with a target vessel anastomosis ring 40. Access tube anastomosis ring 85 is an example of a component of an anastomosis device that is attached to the access tube. The access tube anastomosis ring 85 may also be configured to be integral with the access tube. Any anastomosis components known to those of skill in the art that can be used to join vessels together with an access tube are within the scope of the present invention. For example, an anastomosis component at the end of the access tube may have holes that have been preformed to facilitate suturing the access tube to a target vessel. Alternatively, as previously discussed, an anastomosis component need not be a part of the device at all. The access tube may simply be sutured directly to the target vessel wall, or be attached thereto by any other suitable method.

The target vessel anastomosis ring 40 preferably has posts 42 that are insertable into post slots 82, which are formed in access tube anastomosis ring 85. Preferably, the posts 42 fit inside the post slots 82 such that they are frictionally retained by the post slots 82. Accordingly, once the everted target vessel wall has been placed onto target vessel anastomosis ring 40, as discussed in greater detail later, the anastomosis end 80 of the access tube can be drawn closer to the anastomosis site and its position there can be frictionally maintained by driving the posts 42 further into the slots 82. Various other mechanisms can be used to hold the rings together, such as those disclosed in U.S. patent application Ser. No. 09/736,937 titled Locking Compression Plate Apparatus, which was filed on Dec. 14, 2000, the disclosure of which is expressly incorporated herein by reference.

As indicated above, the access tube anastomosis ring 85 containing the slots 82 can be integrally formed with access tube 110 or it can be attached to access tube 110 by using any suitable attachment device and/or methodology, including any of various mechanical or medical bonding techniques. The access tube anastomosis ring 85 can be made of a variety of flexible, blood-compatible materials, such as polyurethane and the like. However, for reasons discussed below, access tube anastomosis ring 85 will typically be made of a less flexible material than that used to form the portion of access tube 110 defining the conduit 70.

Also, the target vessel anastomosis ring 40 preferably has holding tabs 46 extending towards the access tube or away from the target blood vessel. As discussed in greater detail later, the holding tabs 46 facilitate holding the perimeter of an opening in the target vessel wall in an everted position. Moreover, these holding tabs may be adapted to interdigitate to some degree with access tube holding tabs 86, which may be attached to or preferably integrally formed with the access tube anastomosis ring 85. Target vessel anastomosis ring 40 is an example of a second means for facilitating anastomosis of an access tube to a vessel through cooperation with a first means for facilitating anastomosis. Of course, access tube anastomosis ring 85 may alternatively be the second means for facilitating anastomosis of an access tube to a vessel through cooperation with a first means for facilitating anastomosis, in which case target vessel anastomosis ring 40 may be the first means.

Access tube holding tabs 86, along with a portion of the interior surface 72 of access tube conduit 70, may optionally be covered with a covering 84, as shown in FIG. 13A, and as shown separated from access tube holding tabs 86 in FIG. 13B. This covering may be made of a porous expanded polytetrafluoroethylene (ePTFE) or a material with similar properties, but could also be made from a variety of other materials. Still, any such material will typically be porous and allow for in-growth of biological tissue. In addition to providing a base for tissue in-growth, such a covering provides some cushion for forming a liquid-tight seal at the anastomosis end, and moreover allows the anvil apparatus (discussed later) to center itself more easily on access tube anastomosis ring 85.

A portion of the access tube may be covered with a bio-compatible cuff 75, as best seen in FIG. 11A. The cuff 75 is typically placed on the access tube such that it is located just under the patient's skin 30. When so positioned, fibrous tissue can grow into the cuff 75 such that it integrates with the patient's body and serves as a mechanical anchor to the access tube. Cuff 75 could alternatively be placed at the skin layer 30. Cuff 75 also serves as a transcutaneous infection barrier. In a preferred embodiment, the cuff 75 is made from a polyester felt, but any suitable bio-compatible material could be used.

Fitting within the conduit 70 of the access tube is a plug occluder 90. Occluder 90 is best seen in FIG. 13A, which shows it removed from the access tube conduit 70. Occluder 90 has an occlusion end 92 opposite from a control end 96. The main components of occluder 90 include a plug 53 at occlusion end 92, an access cap 63 at control end 96, and a stem 94 extending from plug 53 to access cap 63. As seen from the figures, stem 94 has a smaller diameter than plug 53.

As shown in FIG. 13A, plug 53 comprises a face 89, one or more sidewalls 88, and a top surface 87. Plug 53 serves to form a seal at anastomosis end 80 of the access tube 110. In addition, plug 53 serves to seat the occluder 90 within the access tube conduit 70 in its proper occluding position, and further plug 53 serves to form an internal seal used to allow fluids to be introduced into the conduit 70 from the access end, as discussed later. Face 89 will typically be flat, but can also have various different shapes. For instance, face 89 could be concave or convex.

The various portions of plug occluder 90 can be made from a variety of suitable materials. The following are illustrative examples of suitable materials, but should not be considered limiting.

Plug 53 can be made of materials such as polyvinylchloride, polyurethane, silicone, or any other suitable blood-compatible material. It may also consist of a substrate made of such a material that is coated with one or more pharmacological agents, such as heparin or heparin-based antimicrobial or antiproliferative agents. For example, in one embodiment the occlusion end 92 is made using a polyvinylchloride substrate coated with a polyurethane mixture having a heparin-based pharmacological agent incorporated therein. As further alternatives, the agents could be integrally formed with the substrate, and/or a polymer could be added to the coating to control the rate of elution.

Stem 94 can be made of similar materials such as polyurethane, or it can be made of any other suitable material such as other plastics or metals. The access cap 63, along with the cap base 61 of the access tube can be made of any blood-compatible material. In one embodiment, the access cap 63 and mating cap base 61 are made of acrylonitrile butadiene styrene (ABS).

As best seen in FIG. 13E, a flushing conduit 91 may run down the center of stem 94. The flushing conduit 91 extends from one or more pores 56 to an opening or port 55 at the cap end 96 of the occluder to provide fluid communication between port 55 and pore(s) 56. The port 55 may be selectively blocked at the cap end 96 with a flushing cap 50, which is threadably engagable with the port end 55 of the flushing conduit 91. Of course, flushing cap 50 need not be threaded. Any suitable configuration for keeping flushing cap 50 in place may be used. Like other parts of the device, the flushing cap 50 may be made of a variety of plastics or other suitable materials. The function of the flushing conduit 91 and related aspects of the present invention are discussed in greater detail later.

If the portion of the access tube defining the conduit 70 is flexible, as previously discussed, part of plug 53 of the occluder 90 can be slightly larger in diameter than the diameter of the interior wall 72 of the access tube conduit 70. In such an embodiment, the access tube conduit 70 bulges slightly as this portion of plug 53 passes therethrough. This creates a seal between the access tube conduit and the vessel lumen. For instance, a sealing lip 72 can be formed in plug 53 of the occluder 90, as seen in FIG. 11B. The sealing lip 72 is a narrow circumferential ridge that causes the access tube conduit 70 to bulge out when the occluder 90 is inside the conduit 70, thereby providing a tight seal against the interior wall 72. The seal caused by sealing lip 72 prevents fluid introduced through the flushing conduit 91 from leaking past plug 53 and into the target vessel lumen. This seal also acts as an additional barrier to prevent the blood or other body fluid from entering the access tube conduit 70.

Moreover, sealing lip 72 may be used to seat the plug 53 in its occluding position. In other words, it can be used as a ledge to engage another portion of the access tube device in order to seat the plug 53 in a desired occluding position by preventing it from going past that position. There are a variety of options for engaging the sealing lip 72. For example, covering 84 may be used to engage sealing lip 72. Alternatively, access tube 110 or access tube anastomosis ring 85 can be formed with a ledge 81, as also shown in FIG. 11B, which is configured to engage sealing lip 72.

Plug 53 may also have one or more tapered portions. The plug embodiment depicted in FIG. 11B has a first tapered portion 51 extending from the distal end of stem 94 to sealing portion 54. In this embodiment, the portion of plug 53 extending beyond access tube anastomosis ring 85 is also tapered. This tapered portion 52 is tapered in order to facilitate seating the occluder against the everted target vessel tissue and also to help prevent damage to the vessel tissue which might otherwise be caused during the process of seating the plug in its occluding position.

It should be understood that many variations of the shape of the plug 53 are within the scope of the present invention. For instance, plug 53 may have fewer or more tapered portions, or it need not be tapered at all. An example of an additional taper would be a seating tapered portion. A seating tapered portion may be used to position plug 53 at its proper occluding position. It could be used to seat plug 53 onto the end of covering 84. Alternatively, such a seating tapered portion could seat itself onto a protrusion or mating tapered portion formed in access tube anastomosis ring 85, as discussed above.

Because access tube anastomosis ring 85 is typically made of a less flexible material than that of the portion of access tube 110 defining the conduit 70, sealing portion 54 of plug 53 is prevented from extending into access tube anastomosis ring 85. Again, this feature, along with tapered portion 57 extending from sealing portion 54, facilitate positioning and seating the occluder in its occluding position and prevent it from extending too far into the target vessel.

It should be understood that the shape of the occluder does not limit the scope of the present invention. While the embodiment discussed thus far utilizes a stemmed occluder wherein only the plug 53 of the occlusion end 92 fits tightly within the access tube conduit 70, countless other variations on the shape and size of the occluder and access tube are possible. To illustrate one such possible variation, refer to FIG. 14. FIG. 14 shows a variation 300' of the plug occluder embodiment of the access tube device having a uniformly-shaped plug occluder. In other words, when the occluder is inside the access tube conduit 70, the occluder fits tightly against the interior wall 72 of the access tube conduit along the entire length of the portion of the occluder that fits within the access tube conduit 70.

It should also be understood that various other embodiments within the scope of the present invention are possible. For instance, two separate access tubes need not be used. Instead, blood can be extracted from and inserted into the same access tube, either simultaneously in a dual-lumen access tube, or intermittently. In addition, only one access tube would be needed for other uses, such as withdrawing particularized amounts of blood for testing, inserting medications or other pharmacological agents into a patient's blood stream, etc.

Moreover, as previously discussed, the access tube of the present invention can comprise any of the various known or hereafter known tubular devices, such as graft vessels, catheters, etc. For example, FIG. 15 shows a graft vessel employed as the access tube of the present invention. Although not shown in the figure, the access end of the graft vessel access tube can be fitted with an access cap such as disclosed herein, or it can be fitted with any other such cap that serves the same purposes, such as stop 359' shown in FIGS. 7A–7C in relation to another embodiment. It should be apparent that each of these are but examples, and that many additional variations are possible, each of which remains within the scope of the invention.

As discussed above, access end 60 of access tube 110 may have threads 62 to engage with access cap 63. Threads 62 may also be used to engage an access coupling 64, as shown in FIGS. 11C and 12. As discussed earlier, the cap base need not include threads. Any configuration designed to secure the access cap 63 of the occluder 90 to the access tube is within the scope of the invention.

When the access cap 63 of this embodiment is engaged with the access end 60 of the access tube 110, making a seal between the occlusion end 92 of the occluder 90 and the interior wall 72 of the access tube conduit 70 creates a chamber 71, which is best seen in FIGS. 13D–13E. This chamber is defined by the interior wall 72 of the conduit 70, the exterior wall of the stem 94 of the occluder 90, the occlusion end 92 or plug 53 of the occluder 90, and the access cap 63 of the occluder 90. The advantages achieved by providing a chamber 71 are discussed below.

During treatment, the conduit of the access tube is exposed to blood from the vessel, and may also be exposed to bacteria or other harmful materials from the environment around the access end 60. Such materials may have a tendency to accumulate on the interior wall 72 of the conduit 70. To eliminate or at least ameliorate such problems, a preferred embodiment of the plug occluder embodiment of the present invention allows for a fluid 78—preferably an antibacterial fluid—to be introduced into the chamber 71 to flush out and/or sanitize the access tube conduit 70. As shown in FIG. 13E, such a fluid 78 may be introduced at the access end of the access tube via a port 55 at the cap end 96 of the occluder 90. Typically, access cap 63 is disengaged from access end 60 of access tube 110 during the flushing, so as to allow the flushing fluid to exit chamber 71.

The port 55 is covered with a flushing cap 50 when not in use. The flushing cap 50 may be engaged to port 55 by any suitable manner of attachment, including threads, snap-fit, friction-fit, etc. As shown in FIG. 13E, one embodiment provides for a threaded engagement between the flushing cap 50 and port 55. Once removed, the flushing cap 50 reveals a flushing conduit 91 defined by the stem 94 of the occluder 90. The flushing conduit 91 opens at one or more pores 56. Pore 56 allows the fluid to enter the chamber 71 to flush and/or sanitize the access tube. Flushing fluid 78 may be flushed through chamber 71 and then out of access end 60 or it may be left in chamber 71 between treatments.

One method for anastomosing any of the access tube apparatus to the sidewall of a blood vessel is carried out by using an external anastomosis operator, which is discussed in great detail in Applications which have been previously incorporated by reference. Briefly stated, the anastomosis operator functions to make an incision or access hole in the sidewall of a target vessel at an anastomosis site and anastomose the access tube of the present invention to the target vessel at the access hole. Anvil apparatus 200, as shown in FIGS. 16A–16D, facilitates making the opening in the target vessel wall 10 through use with the operator (the front portion of the operator is shown in FIGS. 16A–16D). Anvil apparatus 200 may be intraluminally directed within the vessel to the anastomosis site or it may be externally positioned into the lumen at the anastomosis site.

More detailed information regarding methods for intraluminally directing an anvil apparatus is provided in U.S. patent application Ser. No. 09/736,839 titled "Intraluminally Directed Anvil Apparatus and Related Methods and Systems" and filed on Dec. 14, 2000, which is hereby expressly incorporated by reference. Also, more detailed information regarding methods for externally positioning an anvil apparatus is provided in U.S. patent application Ser. No. 10/003, 956 titled "Externally Positioned Anvil Apparatus for Cutting Anastomosis" and filed on Oct. 31, 2001, which is also hereby incorporated by reference.

As seen sequentially in FIGS. 16A–16F, a cutter 400 engages anvil 210 of anvil apparatus 200, thereby forming an opening in the target vessel wall. Anvil apparatus 200, used in connection with the operator, also facilitates everting the vessel tissue defining the opening over the holding tabs 46 of the target vessel anastomosis ring 40. The operator then is used to draw the posts 42 of the target vessel anastomosis ring into the post slots 82 of the access tube anastomosis ring 85, which completes the anastomosis procedure. Of course, after the anastomosis procedure has been completed, the occluder 90 is inserted into the access tube conduit 70 to maintain blood flow control at the anastomosis site.

FIG. 16A depicts anvil 210 being pulled into the target vessel anastomosis ring 40 and against the intima or interior wall of the target vessel 10. Also shown is cutter 400 extending through access tube 110 and approaching distended target vessel 10 on anvil 210.

FIG. 16B depicts the formation of a target vessel opening in the wall of the target vessel 10. This opening is formed by pulling the anvil 210 towards cutter 400 such that cutter 400 engages the vessel wall. As shown in FIG. 16C, cutter 400 also engages anvil 210 so as to ensure a clean cut of the vessel wall. After the cut has been made, the portion of the target vessel wall that now defines the opening rests on the side or landing of anvil 210. This landing aids in everting the tissue that is to be anastomosed as a section of the tissue is held between the landing and holding tabs 46 with a length of tissue resting on the landing that is sufficient to be everted onto holding tabs 46.

As shown in FIG. 16D, access tube anastomosis ring 85 is then brought together with target vessel anastomosis ring 40. In doing so, holding tabs 46 with the everted tissue held thereon are approximated with holding tabs 86 on the access tube anastomosis ring 85. This will typically allow the tissue to contact the optional covering 84 on holding tabs 86. Note that holding tabs 46 and 86 may be circumferentially offset from each other such that the tabs are approximated with each other with tabs 46 directed towards spaces between tabs 86 in an interdigitated configuration. Once the anastomosis is completed, cutter 400 and anvil 210 are drawn through the access tube conduit 70 and out of access tube 110, such that conduit 70 is open as shown in FIG. 16E. Finally, as shown in FIG. 16F, the occluder 90 is inserted into access tube conduit 70 to block fluid communication between the target vessel 10 and the conduit 70.

FIGS. 17–19C illustrate yet another embodiment of the present invention. This embodiment utilizes fluid as the occluder and is typically positioned subcutaneously. An end of access tube 110 opposite from an anastomosis end may be adapted to be fit with either an access cap or an access port device. The embodiment depicted in the accompanying figures is shown fitted with a self-sealing access port 150. Fitting within the access tube at the access end is a fluid occluder, identified generally at 490. As explained in greater detail herein, fluids available for use as a fluid occluder range from viscous fluids, such as gels or hydrogels, to less viscous fluids, such as saline solutions. More information regarding these embodiments is provided in U.S. patent application Ser. No. 10/624,711, titled "Apparatus and Methods for Fluid Occlusion of an Access Tube Anastomosed to an Anatomical Vessel" and filed on Jul. 21, 2003, the disclosure of which is hereby incorporated by specific reference.

FIG. 17 shows two separate fluid occluder embodiments of the access tube devices anastomosed to the sidewalls of two separate target blood vessels, identified at 10a and 10b in the figure. Again, the anastomosis of the access tubes to the vessels can be done by any suitable methodology, including suturing, stapling, welding, clamping, use of adhesives, anastomosis rings and/or plates, or any other anastomosis technology currently known in the art or hereafter developed. However, in the embodiment depicted in the accompanying figures, an anastomosis ring is shown which is adapted to cooperate with a similar ring attached to, or integrally formed with, the access tube.

The first access tube apparatus, or extraction access tube apparatus 500a, is attached to first target blood vessel 10a and extends to a desired subcutaneous location such that its access port is positioned just below the skin. Likewise, the second access tube apparatus, or insertion access tube apparatus 500b, extends from second target blood vessel 10b such that its access port is also positioned just below the skin. As should be apparent to one of skill in the art, the access ports may be configured to allow for suturing or other manner of attachment for securing it to the patient's tissue.

Also, while the accompanying figures show the access tube devices positioned subcutaneously, this aspect of the invention should not be considered limiting. In other words, the devices could easily be positioned such that the access tubes extend percutaneously and are extracorporeally accessible. In such embodiments, it may be preferable to replace the access ports with access caps, such as those disclosed previously with reference to other embodiments of the invention.

When access to the blood is not needed, and as best seen in subsequent figures beginning with FIG. 18A, a fluid is inserted into the access tube conduit to be used as a fluid occluder 490. The fluid occluder 490 blocks fluid communication between each of the vessels and the access tube conduits. In this way, when access to the blood or other body fluid inside the target vessel is desired for treatment or any other reason, one need only remove the fluid serving as a fluid occluder from the access tube conduits to gain access.

In FIG. 18A, each of the two access tube devices is shown at its anastomosis site with a fluid occluder 490 filling its respective access tube conduit. The access ends 60 of the devices are fitted with a self-sealing access port 150, to be described in greater detail later. While the embodiments disclosed in the accompanying figures include access ports, it should be apparent that many variations are possible, some of which do not utilize access ports. For instance, it may be desirable in certain circumstances to replace the access port with an access cap, which may be configured to allow for a snap-fit, threaded, friction-fit or other suitable junction with the access tube. In particular, such a configuration may be desirable for embodiments wherein the access tubes extend percutaneously and are extracorporeally accessible.

Access port 150 may be penetrated by a hypodermic needle 120 or any other medical instrument that can be used to inject and/or withdraw fluid. Such medical instruments may be used to insert the fluid occluder 490 into the access tube conduit 70, as shown in FIG. 18A, withdraw the fluid occluder 490 when vascular access is needed, and to withdraw blood or other body fluids for treatment, as shown in FIG. 18C. Of course, the fluid occluder may be inserted into the access tube conduit by any available methodology.

For instance, for embodiments in which the access end of the access tube is extracorporeally accessible, and in which the access port is replaced with an access cap, the access cap may simply be removed and the fluid occluder inserted by any method available to one of skill in the art. It may also be useful in such embodiments to provide for a pinch valve or other valve to help control the flow of the fluid occluder while the access end of the access tube is open. Alternatively, a device may be employed that periodically and incrementally pushes fluid occluder out of the access tube and into the vessel. Fluid occluder may then be re-inserted into the access tube at certain intervals to maintain the barrier between the body fluid and the access tube.

Because the access port 150 is self-sealing, the access end 60 of the access tube is sealed off as soon as the instrument used to insert the fluid occluder 90 has been withdrawn. A self-sealing access port can comprise any port device used to repeatedly isolate the conduit from external pressure (outside of the vascular system) to allow an attached access tube to contain fluid when the port is not penetrated and provide fluid communication to the conduit when a needle or other access device penetrates into the access port. A port may be self-sealing by virtue of having a penetrable septum or barrier that seals around a needle during access and seals shut upon withdrawal of the needle. Alternatively, a port may be self-sealing by virtue of having a valve structure performing the above-stated functions. One example of a self-sealing access port employing a valve structure is disclosed in U.S. Pat. No. 6,007,516 issued to Burbank et al., the disclosure of which is hereby incorporated by reference in its entirety.

Because this end of the access tube remains closed during the time in between vascular accesses, a vacuum is created at the access end of the access tube conduit. In other words, the enclosed conduit holds the fluid occluder in place. As soon as any fluid occluder leaks out of the access tube, a vacuum is created by the void. This vacuum helps keep the fluid occluder 90 inside the access tube conduit 70.

FIG. 18B shows a close-up of the interface between the access tube apparatus and the target vessel. FIG. 18B shows a sufficient amount of fluid occluder 90 inserted into the access tube conduit such that the interface between the fluid occluder 90 and the body fluid inside vessel 10 is approximately flush with the native vessel wall. At this interface, the surface tension of the fluid occluder helps prevent body fluid from entering the access tube conduit, and vice-versa. However, it is understood that there will typically be some intermixing between the body fluid and the fluid occluder 490 at the interface. Accordingly, the present invention can function without rigidly maintaining the barrier between the body fluid and the fluid occluder 90. It is understood and expected that some of the fluid serving as fluid occluder 490 will enter the patient's bloodstream or other vascular system and likewise some of the patient's blood or other body fluid will enter into the access tube and intermix with the fluid occluder.

A variety of fluids may be suitable for use as a fluid occluder. Such fluids may range in viscosity from near water to near solid. Viscous fluids, such as gels or hydrogels and the like may be used. One or more polymers may also comprise the fluid occluder. Additionally, the fluid occluder may be a combination of gels and/or polymers.

One type of suitable polymer may have a propensity for high biocompatibility as well as modulated biodegradability. Another desirable characteristic of polymers used as fluid occluders or incorporated with fluid occluders is small molecular weight. For example, the molecular weight may be sufficiently small such that the polymer is exerted from the kidneys without accumulation toxicity becoming a problem. Polymers with a molecular weight of less than about 50,000 typically avoid such accumulation toxicity.

One group of polymers considered to possess desired properties for use in fluid occluders is polylactide (PLA). The properties of PLA may be modulated by copolymerization of lactide with other monomers including glycolide. PLA also has a molecular weight of approximately 10,000 and thus will not accumulate in the bloodstream when the device is used in connection with blood vessels.

Another polymer considered to have a desirable molecular weight is polyethylene glycol (PEG). PEG is a non-toxic water soluble polymer which resists recognition by the immune system and exhibits rapid clearance from the body. Because of these properties, fluid occluders prepared from PEG are useful fluid occluders. PEG may also transfer its properties to another molecule when it is covalently bound to that molecule and thus may be used in combination with other polymers or substances to produce a suitable biocompatible occluding fluid. Variants of PEG include poly(ethylene glycol) monomethacrylate (PEGMA) and poly(ethylene glycol) dimethacrylate (PEGDMA). PEG, PEGMA, and PEGDMA can be obtained commercially from such firms as Shearwater Polymers of Huntsville, Ala. and Polysciences Inc. of Warrington, Pa.

Additional examples of fluids potentially available for use as a fluid occluder include hydrogels such as Surgilube® gel, a registered trademark of E. Fougera & Co., a division of Altana, Inc. of Melville, N.Y. containing Chlorhexidine Gluconate and Hypan SA100H produced by Hymedic International, Inc. of Dayton, N.J. Still other examples of substances potentially useful in fluid occluders include polyesters, poly(orthoesters), polyanhydrides, polyamino acid, polyalkyl cyanoacrylates, polyphophazenes, copolymers of (PLA/PGA), and aspirate or Poly(ethylene oxide) PEO.

Less viscous fluids may also be used, such as saline solutions and the like. Depending upon the substance used, the fluid occluder may also expand when in contact with water. In such embodiments, the occluding fluid will continually expand such that the layer of fluid occluder adjacent to the body fluid will erode out into the stream of fluid in the anatomical vessel. This provides a continually renewing surface and a mechanism to keep the interface between the body fluid and the fluid occluder from retracting back into the access tube.

Each of the foregoing are examples of fluid occluding means for occluding an access tube means. Obviously, the type of fluid used to occlude the access tube should not be considered as limiting the scope of the invention.

In order to reduce the likelihood of infection, thrombosis, and other complications, the fluid occluder 490 may have pharmacological agents incorporated therein. Such agents include, but are not limited to, antibacterial agents to prevent infection, antithrombotic agents to prevent thrombosis formation, and/or antiproliferative agents to prevent neo-intimal hyperplasia or other potential problems. One or more of these agents can also be used as a coating on the interior wall 72 of the access tube conduit 70. Antibacterial agents that have been shown to provide an effective short-term infection barrier when applied as a coating include chlorhexadine and silver sulfadiazine. Drug-eluting coatings containing antiproliferative agents, such as Paclitaxel, have been shown to be beneficial in preventing restenosis due to neo-intimal hyperplasia. However, any pharmacological substance known to those skilled in the art now or hereafter could be used as a coating and/or incorporated into the fluid occluder 490.

When access to the vessel is desired, the fluid may then be withdrawn from the access tube conduit 70. This may be accomplished in any number of ways. For instance, for embodiments including an access port, the fluid may be withdrawn with a hypodermic needle 120 via the port. Then, vascular access may be obtained by again inserting a needle or other suitable medical device into the access port.

In FIG. 18C the access tubes are shown with needles 120 inserted into their access ports 150 and with their fluid occluders removed to allow for vascular access for blood treatment. As the arrows in the figure indicate, blood flows from blood vessel 10a into the access tube conduit 70 of occludable extraction access tube apparatus 500*a* and is drawn to a blood treatment device such as a blood dialysis pump with a needle or other extraction device. As indicated above, because the invention is suitable for use in providing access to body fluids other than blood, the treatment device can be any device capable of performing treatment on any such body fluid accessed by the methods and apparatus of the invention. Of course, for other uses of the invention, a treatment device need not even be used. For instance, access to a body fluid may be needed for obtaining samples of the fluid, or for inserting medications or other substances into the vascular system. However, when a treatment device is used, as shown in FIG. 18C, after the blood has been treated it is inserted into access tube conduit 70 of occludable insertion access tube apparatus 500*b* via another needle 120 or other insertion device. The blood then re-enters the patient's bloodstream through blood vessel 10*b*.

Once access to the vascular system of the target vessel is no longer needed, needles 120 are re-inserted into the self-sealing access ports 150 of the two access tube devices to re-insert the fluid to be used as the fluid occluder 490. Once the fluid has filled the access tube conduits such that the blood/occluding-fluid interface is near the native vessel wall, as shown in FIGS. 18A–18B, the needles can be withdrawn until further treatment is needed.

FIG. 19A provides a more detailed depiction of a fluid occluder embodiment of the access tube apparatus of the present invention. Access tube 110 has an anastomosis end 80 opposite from an end adapted to be fit with a port device 150. A conduit 70 extends from the anastomosis end 80 to the opposite end. The access tube 110 and conduit 70 therein can be of any cross-sectional shape and size. As stated previously, the terms "access tube" is meant to encompass any of various known or hereafter known suitable devices, including graft vessels, catheters, and the like.

Like the plug occluder embodiment, one or more anastomosis components may be used to facilitate the attachment of the access tube to the target vessel.

In the embodiment shown in FIG. 19A, the end of access tube 110 opposite from the anastomosis end 80 is configured to engage an access port 150. The access tube may be joined with the access port by any configuration suitable for engaging a portion of the access port 150. To achieve this, the access tube 110 may be configured to allow for a snap-fit, threaded, friction-fit or other suitable junction between it and the access port 150.

The access port 150 may optionally have suturing holes 153 for facilitating attachment of the port to the patient's tissue. These holes are but one example of a manner by which the access port 150 and/or the access tube device itself may be secured to tissue.

As discussed above, the end of access tube 110 opposite from the anastomosis end 80 may have threads to engage with an access cap and/or access port 150. However, the access tube need not include threads. Any configuration designed to secure the access port 150 and/or access cap to the access tube is within the scope of the invention.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A method for providing repeated access to a body fluid in an anatomical, native vessel, comprising:
    providing an occludable access tube having an anastomosis end;
    anastomosing the access tube at its anastomosis end to the sidewall of the anatomical vessel, without sutures, for fluid communication between the anatomical, native vessel and the access tube;
    occluding the access tube with an occluder at its anastomosis end to prevent the body fluid in the anatomical, native vessel from entering the access tube;
    opening the access tube by selectively moving the occluder so that the occludable access tube is no longer occluded to provide fluid communication between the anatomical, native vessel and the access tube;
    enabling fluid communication between the access tube and a device; and
    re-occluding the access tube.

2. The method of claim 1, further comprising reoccluding the access tube with an occluder at its anastomosis end to prevent the body fluid from entering the access tube.

3. The method of claim 1, wherein the body fluid is blood.

4. The method of claim 3, further comprising providing fluid communication between the access tube and a blood treatment device.

5. The method of claim 4, further comprising providing fluid communication between the blood treatment device and a second access tube anastomosed to a blood vessel.

6. The method of claim 1, wherein the access tube has an access end opposite from the anastomosis end and wherein the access tube extends percutaneously with the access end being extracorporeally positioned.

7. The method of claim 6, wherein the occluder comprises a removable plug occluder.

8. The method of claim 1, wherein the entire access tube is positioned subcutaneously.

9. The method of claim 1, further comprising a self-sealing access port in fluid communication with the access tube.

10. The method of claim 1, further comprising a self-sealing port device in fluid communication with the occluder.

11. The method of claim 1, wherein the occluder comprises a fluid.

12. The method of claim 1, wherein the occluder comprises a balloon.

13. The method of claim 12, wherein the balloon is toroidal shaped.

14. The method of claim 1, wherein the end of the access tube opposite from the anastomosis end is closed.

15. The method of claim 1, wherein the access tube has an anastomosis component at the anastomosis end.

16. The method of claim 15, wherein the anastomosis component is an anastomosis ring.

17. The method of claim 1, further comprising the step of exposing the body fluid to a pharmacological agent via the occluder.

18. An apparatus for facilitating repeated access to a body fluid in an anatomical, native vessel, comprising:
    an access tube having an anastomosis end, wherein the anastomosis end is configured for sutureless attachment of the anastomosis end of the access tube to the sidewall of an anatomical, native vessel to enable fluid communication between the anatomical, native vessel and the access tube; and an occluder configured to fit within the access tube at the anastomosis end of the access tube to block fluid communication between the anatomical, native vessel and the access tube, wherein the occluder can be selectively moved to allow for fluid communication between the anatomical, native vessel and the access tube to be re-established.

19. The apparatus of claim 18, further comprising an anastomosis component at the anastomosis end of the access tube to facilitate anastomosis of the access tube to the sidewall of the anatomical, native vessel.

20. The apparatus of claim 19, wherein the anastomosis component is an anastomosis ring.

21. The apparatus of claim 18, wherein the access tube has an access end opposite from the anastomosis end, and wherein the access tube is configured to extend percutaneously with the access end being extracorporeally positioned.

22. The apparatus of claim 18, wherein the entire access tube is positioned subcutaneously.

23. The apparatus of claim 18, further comprising a self-sealing access port in fluid communication with the access tube.

24. The apparatus of claim 23, wherein the self-sealing access port is disposed at the end of the access tube opposite from the anastomosis end.

25. The apparatus of claim 18, further comprising a self-sealing port device in fluid communication with the occluder.

26. The apparatus of claim 25, wherein the self-sealing port device is disposed at the end of the access tube opposite from the anastomosis end.

27. The apparatus of claim 18, wherein the occluder comprises a fluid.

28. The apparatus of claim 18, wherein the occluder comprises a balloon.

29. The apparatus of claim 28, wherein the balloon is toroidal shaped.

30. The apparatus of claim 18, wherein the occluder includes a pharmacological agent.

31. An apparatus for facilitating repeated access to a body fluid in an anatomical, native vessel, comprising:

access tube means for accessing an anastomosed vessel, wherein the access tube means has an anastomosis end configured for sutureless attachment of the anastomosis end of the access tube to the sidewall of an anatomical, native vessel to enable fluid communication between the anatomical, native vessel and the access tube means; and occluding means for selectively occluding an opening in an anatomical, native vessel, wherein the occluding means is configured to fit within the access tube means at the anastomosis end of the access tube to block fluid communication between the anatomical, native vessel and the access tube means, wherein the occluding means can be selectively moved to allow for fluid communication between the anatomical, natively vessel and the access tube means to be re-established.

* * * * *

UNITED STATES PATENT AND TRADEMARK OFFICE
CERTIFICATE OF CORRECTION

PATENT NO. : 7,118,546 B2
APPLICATION NO. : 10/624315
DATED : October 10, 2006
INVENTOR(S) : Blatter It is certified that error appears in the above-identified patent and that said Letters Patent is hereby corrected as shown below:

Drawing sheets 17 and 27 have been replaced with the attached replacement sheets.

Column 5, line 67, "... cover according to ..." change to --... cover 152 according to ...--

Column 8, line 39, "... the occlusal balloon an aqueous ..." change to --... the occlusal balloon with an aqueous ...--

Column 9, line 57, "... that has a can be ..." change to --... that can be ...--

Column 10, line 26, "... Millipore Corp. or Bedford, Mass." change to --... Millipore Corp. of Bedford, Mass.--; line 32, "... membrane," change to --... membranes,--

Column 14, line 32, "... membrane is ..." change to --... membrane $143b$ is ...--

Column 17, line 1, "... that the while ..." change to --... that while ...--

Column 19, line 9, "... access tube itself ..." change to --... access tube 110 itself ...--

Column 27, line 19, "interior surface 72 ..." change to --interior surface 72 (best seen in FIG. 13D) ...--; line 57, "further plug 53 ..." change to --plug 53 further ...--

Column 28, lines 39, 41-42, 45, 50, 55-56, 59, "... sealing lip 72 ..." change to --... sealing lip 74 ...--; line 63, "sealing portion 54." change to --sidewalls 88.--

Column 29, lines 16, 19, "... sealing portion 54 ..." change to --... sidewalls 88 ...--

Column 30, line 9, "... conduit of the access tube ..." change to --... conduit 70 of the access tube 110 ...--; line 25, "... may be engaged to port 55 ..." change to --... may engage port 55 ...--

UNITED STATES PATENT AND TRADEMARK OFFICE
CERTIFICATE OF CORRECTION

PATENT NO.         : 7,118,546 B2
APPLICATION NO. : 10/624315
DATED                : October 10, 2006
INVENTOR(S)      : Blatter It is certified that error appears in the above-identified patent and that said Letters Patent is hereby corrected as shown below:

Column 33, lines 28, 29-30, ". . . fluid occluder 90 . . ." change to --. . . fluid occluder 490 . . .--

Column 34, line 5, ". . . covalently bound" change to --. . . covalently bonded--

Column 38, line 28, claim 31, ". . . natively . . ." change to --. . . native . . .--

Signed and Sealed this

Fourth Day of November, 2008

JON W. DUDAS
*Director of the United States Patent and Trademark Office*